United States Patent
Gray et al.

(10) Patent No.: US 11,827,636 B2
(45) Date of Patent: Nov. 28, 2023

(54) DEGRADATION OF CYCLIN-DEPENDENT KINASE 8 (CDK8) BY CONJUGATION OF CDK8 INHIBITORS WITH E3 LIGASE LIGAND AND METHODS OF USE

(71) Applicant: DANA-FARBER CANCER INSTITUTE, INC., Boston, MA (US)

(72) Inventors: Nathanael S. Gray, Boston, MA (US); Tinghu Zhang, Brookline, MA (US); Calla M. Olson, Brookline, MA (US); Yanke Liang, Brookline, MA (US); Nicholas Kwiatkowski, Auburn, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 105 days.

(21) Appl. No.: 17/561,032

(22) Filed: Dec. 23, 2021

(65) Prior Publication Data

US 2022/0112191 A1    Apr. 14, 2022

Related U.S. Application Data

(63) Continuation of application No. 17/083,940, filed on Oct. 29, 2020, now Pat. No. 11,247,991, which is a continuation of application No. 16/094,105, filed as application No. PCT/US2017/028948 on Apr. 21, 2017, now Pat. No. 10,865,205.

(60) Provisional application No. 62/326,584, filed on Apr. 22, 2016.

(51) Int. Cl.
| | |
|---|---|
| *C07D 471/04* | (2006.01) |
| *C07D 471/10* | (2006.01) |
| *A61K 47/18* | (2017.01) |
| *A61K 47/54* | (2017.01) |
| *A61P 35/00* | (2006.01) |

(52) U.S. Cl.
CPC ............ *C07D 471/04* (2013.01); *A61K 47/18* (2013.01); *A61K 47/545* (2017.08); *C07D 471/10* (2013.01); *A61P 35/00* (2018.01)

(58) Field of Classification Search
CPC .... C07D 471/04; C07D 471/10; A61K 47/18; A61K 47/54; A61P 35/00
See application file for complete search history.

(56) References Cited

U.S. PATENT DOCUMENTS

2015/0246913 A1    9/2015    Gray et al.

FOREIGN PATENT DOCUMENTS

| EP | 2985285 A1 | 2/2016 |
|---|---|---|
| WO | 2015160845 A2 | 10/2015 |

OTHER PUBLICATIONS

Bondeson; et al., "Catalytic in vivo protein knockdown by small-molecule PROTACs," Nature Chemical Biology, vol. 11, No. 8, Jun. 10, 2015 (Jun. 10, 2015), pp. 611-617.
Bulatov, et al., "Targeting Cullin-Ring E3 Ubiquitin Ligases for Drug Discovery: Structure, Assembly and Small-Molecule Modulation", Biochem. J., 2015, vol. 467, No. 3, pp. 365-386.
Dale, et al., "A Selective Chemical Probe for Exploring the Role of CDK8 and CDK19 in Human Disease," Nat. Chem. Biol., 2015, vol. 11, pp. 973-980.
Huang, et al., "Drugging the Undruggables: Exploring the Ubiquitin System for Drug Development", Cell Res., 2016, vol. 26, No. 4, pp. 484-498.
Lai, et al., "Modular PROTAC Design for the Degradation of Oncogenic BCR-ABL," Angew. Chem. Int. Ed., 2016, vol. 65, No. 2, pp. 807-810.

(Continued)

*Primary Examiner* — Bruck Kifle
(74) *Attorney, Agent, or Firm* — BURNS & LEVINSON, LLP; Daniel W. Clarke; Shawn P. Foley

(57) ABSTRACT

The present application provides bifunctional compounds of Formula (Ia) or (Ib):

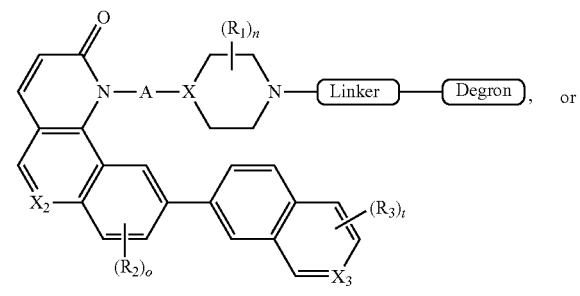

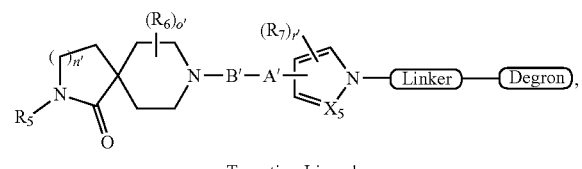

or a pharmaceutically acceptable salt, hydrate, solvate, prodrug, stereoisomer, or tautomer thereof, which act as protein degradation inducing moieties for cyclin-dependent kinase 8 (CDK8). The present application also relates to methods for the targeted degradation of CDK8 through the use of the bifunctional compounds that link a ubiquitin ligase-binding moiety to a ligand that is capable of binding to CDK8 which can be utilized in the treatment of disorders modulated by CDK8.

16 Claims, 4 Drawing Sheets

(56) References Cited

OTHER PUBLICATIONS

Liu, et al., "Discovery of 1-(4-(4-propionylpiperazin-l-yl)-3-(trifluoro methyl) phenyl)-9 (quinolin-3-yl) benzo [h][1, 6] naphthyridin-2 (1H)-one as a highly potent, selective mammalian target of rapamycin (mTOR) inhibitor for the treatment of cancer," J. Med. Chem., 2010, vol. 53, No. 19, pp. 7146-7155.

Lu, et al., "Hijacking the E3 Ubiquitin Ligase Cereblon to Efficiently Target BRD4", Chem. Biol., 2015, vol. 22, No. 6, pp. 755-763.

Mallinger, et al., "2, 8-Disubstituted-1, 6-Naphthyridines and 4, 6-Disubstituted-isoquinolines with Potent, Selective Affinity for CDK8/19," ACS Med. Chem. Lett., 2016, vol. 7, No. 6, pp. 573-578.

Mallinger, et al., "Discovery of Potent, Selective, and Orally Bioavailable Small-Molecule Modulators of the Mediator Complex-Associated Kinases CDK8 and CDK19," J. Med. Chem., 2016, vol. 59, No. 3, pp. 1078-1101.

Zengerle, et al., "Selective Small Molecule Induced Degradation of the BET Bromodomain Protein BRD4", ACS Chem. Biol., 2015, vol. 10, No. 8, pp. 1770-1777.

DEGRADATION OF CYCLIN-DEPENDENT KINASE 8 (CDK8) BY CONJUGATION OF CDK8 INHIBITORS WITH E3 LIGASE LIGAND AND METHODS OF USE

RELATED APPLICATION

This application is a continuation of U.S. application Ser. No. 17/083,940, filed on Oct. 29, 2020, which is a continuation of U.S. application Ser. No. 16/094,105, filed on Oct. 16, 2018 (now U.S. Pat. No. 10,865,205), which is a U.S. National Phase application, filed under U.S.C. § 371, of International Application No. PCT/US2017/028948, filed on Apr. 21, 2017, which claims priority to, and the benefit of, U.S. Application No. 62/326,584, filed on Apr. 22, 2016, the entire contents of each of which are incorporated herein by reference.

GOVERNMENT SUPPORT

This invention was made with government support under grant number R01 CA179483 awarded by The National Institutes of Health. The government has certain rights in the invention.

BACKGROUND

Ubiquitin-Proteasome Pathway (UPP) is a critical pathway that regulates proteins and degrades misfolded or abnormal proteins. UPP is central to multiple cellular processes, and if defective or imbalanced, leads to pathogenesis of a variety of diseases. The covalent attachment of ubiquitin to specific protein substrates is achieved through the action of E3 ubiquitin ligases. These ligases comprise over 500 different proteins and are categorized into multiple classes defined by the structural element of their E3 functional activity. For example, cereblon (CRBN) interacts with damaged DNA binding protein 1 and forms an E3 ubiquitin ligase complex with Cullin 4 in which the proteins recognized by CRBN are ubiquitinated and degraded by proteasomes. Various immunomodulatory drugs (IMiDs), e.g. thalidomide and lenalidomide, binds to CRBN and modulates CRBN's role in the ubiquitination and degradation of protein factors involved in maintaining regular cellular function.

Bifunctional compounds composed of a target protein-binding moiety and an E3 ubiquitin ligase-binding moiety have been shown to induce proteasome-mediated degradation of selected proteins. These drug-like molecules offer the possibility of temporal control over protein expression, and could be useful as biochemical reagents for the treatment of diseases.

Cyclin-dependent kinase is a kinase family integrating multiple signaling pathways to control either cell cycle or gene transcription. CDK1, 2, 4 and 6 are the critical enzymes that drive cell cycle transition. For example, CDK1 is a key determinant of mitotic progression, CDK2 regulates DNA replication in S phase, and CDK4/6 drives the cell cycle from G0 or G1 to S phase by phosphorylation on Rb protein to activate expression of genes involved in cell cycle control. CDK7, 9 and 12 are known enzymes that regulate the transcription instead of directly promoting cell cycles. CDK7 is the enzymatic component of TFIIH complex which is responsible for regulating transcription initiation, and CDK9 and CDK12 regulate transcription elongation and processing.

Deregulation of CDKs has been shown to have a significant impact on the cell state and is frequently identified as oncogenic. Numerous selective or pan-CDK small molecule inhibitors have been identified, however, most of the known inhibitors have failed in clinic trials due to the lack of high systemic drug concentration. More recently, the development of a CDK7 covalent inhibitor, THZ1, has demonstrated that irreversible binders are superior to reversible CDK binders.

Alternative strategies to inhibit cyclin-dependent kinases, such as CDK8, are needed. At present, suitable compounds with alternative mechanisms of action targeting CDK8 are not available. The present application addresses the need.

SUMMARY

The present application relates to novel bifunctional compounds, which function to recruit targeted proteins to E3 ubiquitin ligase for degradation, and methods of preparation and uses thereof. The bifunctional compound is of Formula X:

$$TL-L-D \qquad (X),$$

wherein:
the Targeting Ligand (TL) is capable of binding to a targeted protein, such as a cyclin-dependent kinase (e.g., CDK8);
the Linker (L) is a group that covalently binds to the Targeting Ligand and the Degron; and
the Degron (D) is capable of binding to a ubiquitin ligase, such as an E3 ubiquitin ligase (e.g., cereblon).

The present application also relates to targeted degradation of proteins through the use of bifunctional compounds, including bifunctional compounds that link an E3 ubiquitin ligase-binding moiety to a ligand that binds the targeted proteins.

The present application also relates to a bifunctional compound of Formula Ia or Ib:

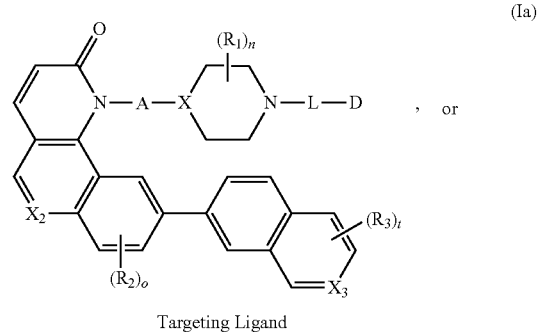

Targeting Ligand

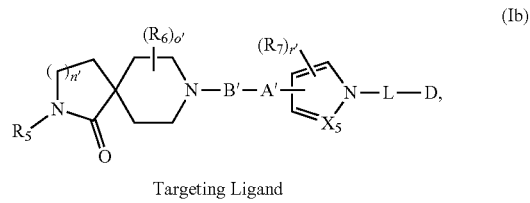

Targeting Ligand or an enantiomer, diastereomer, stereoisomer, or pharmaceutically acceptable salt thereof,
wherein:
$R_1$, $R_2$, $R_3$, $R_5$, $R_6$, $R_7$, A, A', B', X, $X_2$, $X_3$, $X_5$, n, n', o, o', t and r' are each as defined herein;

the Linker is a group that covalently binds to

in Formula (Ia) or

in Formula (Ib) and the Degron;
the Degron is capable of binding to a ubiquitin ligase, such as an E3 ubiquitin ligase (e.g., cereblon); and
the Targeting Ligand is capable of binding to a targeted protein, such as CDK8.

The present application further relates to a Degron of Formula D1:

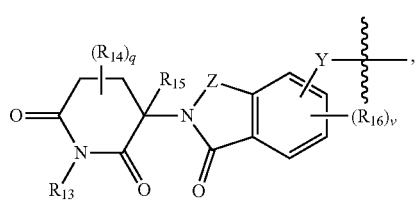

or an enantiomer, diastereomer, or stereoisomer thereof, wherein Y, Z, $R_{13}$, $R_{14}$, $R_{15}$, $R_{16}$, v, and q are each as defined herein.

The present application further relates to a Linker of Formula L0:

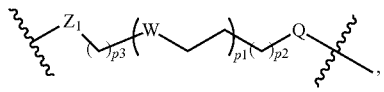

or an enantiomer, diastereomer, or stereoisomer thereof, wherein p1, p2, p3, W, Q, and $Z_1$ are each as defined herein, the Linker is covalently bonded to a Degron via the

next to Q, and covalently bonded to a Targeting Ligand via the

next to $Z_1$.

The present application also relates to a pharmaceutical composition comprising a therapeutically effective amount of a bifunctional compound of the application, or an enantiomer, diastereomer, stereoisomer, or pharmaceutically acceptable salt thereof, and a pharmaceutically acceptable carrier.

Another aspect of the present application relates to a method of inhibiting a kinase (e.g., CDK8). The method comprises administering to a subject in need thereof an effective amount of a bifunctional compound of the application, or a pharmaceutically acceptable salt, hydrate, solvate, prodrug, stereoisomer, or tautomer thereof, or a pharmaceutical composition of the application.

Another aspect of the present application relates to a method of modulating (e.g., decreasing) the amount of a kinase (e.g., CDK8). The method comprises administering to a subject in need thereof a therapeutically effective amount of a bifunctional compound of the application, or a pharmaceutically acceptable salt, hydrate, solvate, prodrug, stereoisomer, or tautomer thereof, or a pharmaceutical composition of the application.

Another aspect of the present application relates to a method of treating or preventing a disease (e.g., a disease in which CDK8 plays a role). The method comprises administering to a subject in need thereof an effective amount of a bifunctional compound of the application, or a pharmaceutically acceptable salt, hydrate, solvate, prodrug, stereoisomer, or tautomer thereof, or a pharmaceutical composition of the application. In one aspect, the disease is a kinase (e.g., CDK8) mediated disorder. In one aspect, the disease is a proliferative disease (e.g., a proliferative disease in which CDK8 plays a role).

Another aspect of the present application relates to a method of treating or preventing cancer in a subject, wherein the cancer cell comprises an activated CDK8 or wherein the subject is identified as being in need of CDK8 inhibition for the treatment or prevention of cancer. The method comprises administering to the subject an effective amount of a bifunctional compound of the application, or a pharmaceutically acceptable salt, hydrate, solvate, prodrug, stereoisomer, or tautomer thereof, or a pharmaceutical composition of the application.

Another aspect of the present application relates to a kit comprising a bifunctional compound capable of inhibiting CDK8 activity, selected from a bifunctional compound of the application, or a pharmaceutically acceptable salt, hydrate, solvate, prodrug, stereoisomer, or tautomer thereof.

Another aspect of the present application relates to a kit comprising a bifunctional compound capable of modulating (e.g., decreasing) the amount of CDK8, selected from a bifunctional compound of the application, or a pharmaceutically acceptable salt, hydrate, solvate, prodrug, stereoisomer, or tautomer thereof.

Another aspect of the present application relates to a bifunctional compound of the application, or a pharmaceutically acceptable salt, hydrate, solvate, prodrug, stereoisomer, or tautomer thereof, or a pharmaceutical composition of the application, for use in the manufacture of a medicament for inhibiting a kinase (e.g., CDK8) or for modulating (e.g., decreasing) the amount of a kinase (e.g., CDK8).

Another aspect of the present application relates to a bifunctional compound of the application, or a pharmaceutically acceptable salt, hydrate, solvate, prodrug, stereoisomer, or tautomer thereof, or a pharmaceutical composition of the application, for use in the manufacture of a medicament for treating or preventing a disease (e.g., a disease in which CDK8 plays a role). In one aspect, the disease is a kinase (e.g., CDK8) mediated disorder. In one aspect, the disease is a proliferative disease (e.g., a proliferative disease in which CDK8 plays a role).

Another aspect of the present application relates to a bifunctional compound of the application, or a pharmaceutically acceptable salt, hydrate, solvate, prodrug, stereoisomer, or tautomer thereof, or a pharmaceutical composition of the application, for use in the manufacture of a medicament for treating or preventing cancer in a subject, wherein the cancer cell comprises an activated CDK8 or wherein the subject is identified as being in need of CDK8 inhibition for the treatment or prevention of cancer.

Another aspect of the present application relates to a bifunctional compound of the application, or a pharmaceutically acceptable salt, hydrate, solvate, prodrug, stereoisomer, or tautomer thereof, or a pharmaceutical composition of the application, for use in inhibiting a kinase (e.g., CDK8) or modulating (e.g., decreasing) the amount of a kinase (e.g., CDK8).

Another aspect of the present application relates to a bifunctional compound of the application, or a pharmaceutically acceptable salt, hydrate, solvate, prodrug, stereoisomer, or tautomer thereof, or a pharmaceutical composition of the application, for use in treating or preventing a disease (e.g., a disease in which CDK8 plays a role). In one aspect, the disease is a kinase (e.g., CDK8) mediated disorder. In one aspect, the disease is a proliferative disease (e.g., a proliferative disease in which CDK8 plays a role).

Another aspect of the present application relates to a bifunctional compound of the application, or a pharmaceutically acceptable salt, hydrate, solvate, prodrug, stereoisomer, or tautomer thereof, or a pharmaceutical composition of the application, for use in treating or preventing cancer in a subject, wherein the cancer cell comprises an activated CDK8 or wherein the subject is identified as being in need of CDK8 inhibition for the treatment or prevention of cancer.

The present application provides inhibitors of CDK8 that are therapeutic agents in the treatment or prevention of diseases such as cancer and metastasis.

The present application further provides compounds and compositions with an improved efficacy and/or safety profile relative to known CDK8 inhibitors. The present application also provides agents with novel mechanisms of action toward CDK8 kinases in the treatment of various types of diseases including cancer and metastasis.

The compounds and methods of the present application address unmet needs in the treatment of diseases or disorders in which pathogenic or oncogenic endogenous proteins (e.g., CDK8) play a role, such as cancer.

The details of the disclosure are set forth in the accompanying description below. Although methods and materials similar or equivalent to those described herein can be used in the practice or testing of the present application, illustrative methods and materials are now described. In the case of conflict, the present specification, including definitions, will control. In addition, the materials, methods, and examples are illustrative only and are not intended to be limiting. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

The contents of all references (including literature references, issued patents, published patent applications, and co-pending patent applications) cited throughout this application are hereby expressly incorporated herein in their entireties by reference. The references cited herein are not admitted to be prior art to the application.

DETAILED DESCRIPTION

Compounds of the Application

Figure 1A:
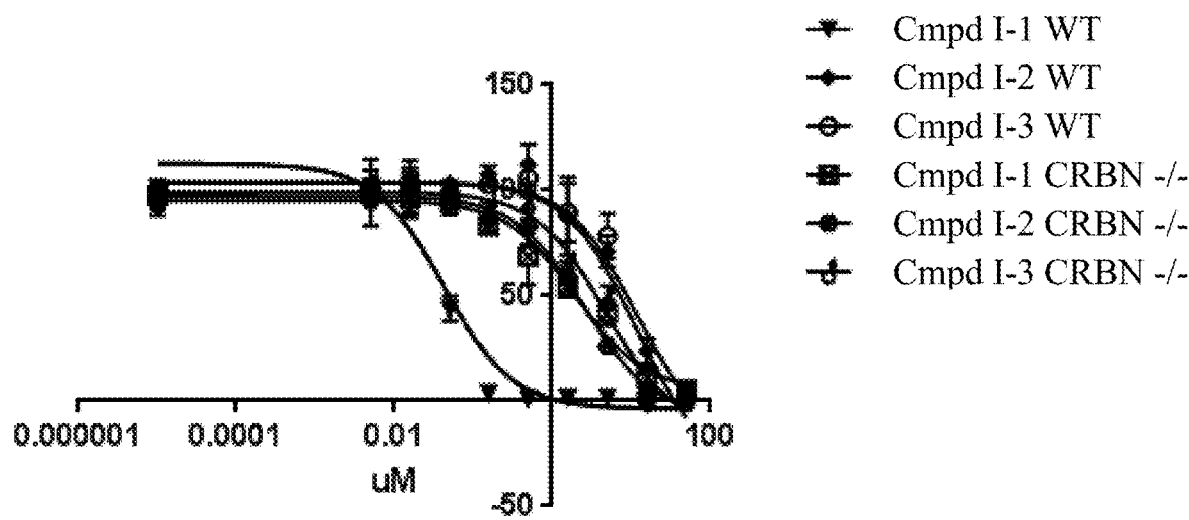
FIG. 1A is a graph showing anti-proliferative effects of Compound I-1, Compound I-2, and Compound I-3 in wild-type (WT) or cereblon knockout (CRBN−/−) cells at various concentrations. Antiproliferative effects were assessed 72 hours after treatment.

The present application relates to bifunctional compounds having utility as modulators of ubiquitination and proteosomal degradation of targeted proteins, especially compounds comprising a moiety capable of binding to a polypeptide or a protein that is degraded and/or otherwise inhibited by the bifunctional compounds of the present application. In particular, the present application is directed to compounds which contain a moiety, e.g., a small molecule moiety (i.e., having a molecular weight of below 2,000, 1,000, 500, or 200 Daltons), such as a thalidomide-like moiety, which is capable of binding to an E3 ubiquitin ligase, such as cereblon, and a ligand that is capable of binding to a target protein, in such a way that the target protein is placed in proximity to the ubiquitin ligase to effect degradation (and/or inhibition) of that protein.

In one embodiment, the present application provides a bifunctional compound of Formula X:

TL-L-D       (X), wherein:
- the Targeting Ligand (TL) is capable of binding to a targeted protein, such as CDK8;
- the Linker (L) is a group that covalently binds to the Targeting Ligand and the Degron; and
- the Degron (D) is capable of binding to a ubiquitin ligase, such as an E3 ubiquitin ligase (e.g., cereblon).

In one embodiment, the present application provides a compound of Formula Ia:

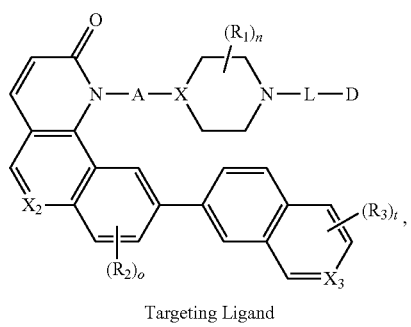

(Ia)

Targeting Ligand or an enantiomer, diastereomer, stereoisomer, or pharmaceutically acceptable salt thereof,
wherein:
- $R_1$, $R_2$, $R_3$, A, X, $X_2$, $X_3$, n, o, and t are each as defined herein;
- the Linker is a group that covalently binds to

and the Degron;
- the Degron is capable of binding to a ubiquitin ligase, such as an E3 ubiquitin ligase (e.g., cereblon); and
- the Targeting Ligand is capable of binding to a targeted protein, such as CDK8.

In one embodiment, the present application provides a compound of Formula Ib:

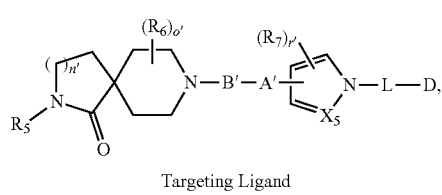

(Ib)

Targeting Ligand or an enantiomer, diastereomer, stereoisomer, or pharmaceutically acceptable salt thereof,
wherein:
- $R_5$, $R_6$, $R_7$, A', B', $X_5$, n', o', and r' are each as defined herein;

the Linker is a group that covalently binds to

and the Degron;
- the Degron is capable of binding to a ubiquitin ligase, such as an E3 ubiquitin ligase (e.g., cereblon); and
- the Targeting Ligand is capable of binding to a targeted protein, such as CDK8.

The present application further relates to a Degron of Formula D1:

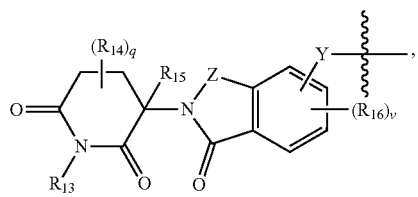

(D1)

or an enantiomer, diastereomer, or stereoisomer thereof, wherein Y, Z, $R_{13}$, $R_{14}$, $R_{15}$, $R_{16}$, q, and v are each as defined herein.

The present application further relates to a Linker of Formula L0:

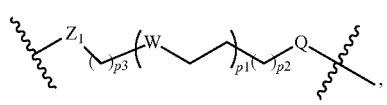

(L0)

or an enantiomer, diastereomer, or stereoisomer thereof, wherein p1, p2, p3, W, Q, and $Z_1$ are each as defined herein, the Linker is covalently bonded to a Degron via the

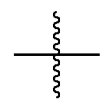

next to Q, and covalently bonded to the Targeting Ligand via the

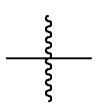

next to $Z_1$.

Targeting Ligand

Targeting Ligand (TL) (or target protein moiety or target protein ligand or ligand) is a small molecule which is capable of binding to a target protein of interest, such CDK8.

In one embodiment, a Targeting Ligand is a compound of Formula TL-I:

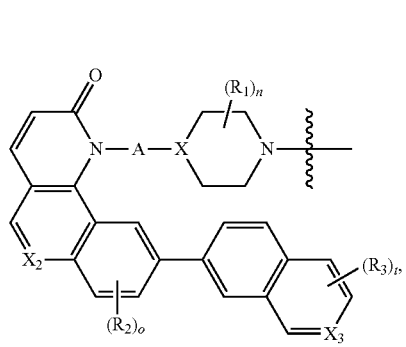

(TL-I)

or an enantiomer, diastereomer, stereoisomer, or pharmaceutically acceptable salt thereof,
wherein:

A is

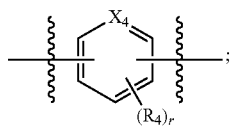

;

X is N or CH;
$X_2$ is N or CH;
$X_3$ is N or CH;
$X_4$ is N or CH;
each $R_1$ is independently $(C_1-C_4)$ alkyl or $(C_1-C_4)$ haloalkyl;
each $R_2$ is independently $(C_1-C_4)$ alkyl, $(C_1-C_4)$ haloalkyl, $(C_1-C_4)$ alkoxy, $(C_1-C_4)$ haloalkoxy, halogen, OH, or $NH_2$;
each $R_3$ is independently $(C_1-C_4)$ alkyl, $(C_1-C_4)$ haloalkyl, $(C_1-C_4)$ alkoxy, $(C_1-C_4)$ haloalkoxy, halogen, OH, or $NH_2$;
each $R_4$ is independently $(C_1-C_4)$ alkyl, $(C_1-C_4)$ haloalkyl, $(C_1-C_4)$ alkoxy, $(C_1-C_4)$ haloalkoxy, halogen, OH, or $NH_2$; and
t, n, o, and r are each independently 0, 1, 2, or 3;

wherein the Targeting Ligand is bonded to the Linker via the

next to

In some embodiments, A is

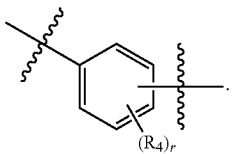

.

In other embodiments, A is

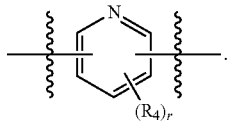

.

In other embodiments, A is

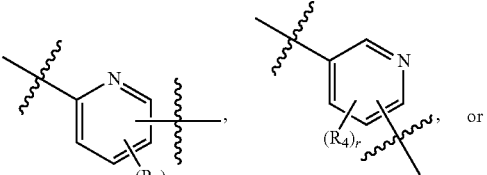

, or

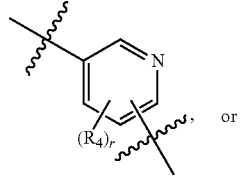

.

In other embodiments, A is

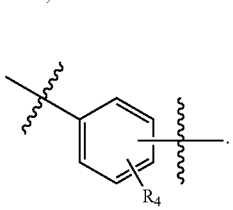

.

In some embodiments, X is N. In other embodiments, X is CH.

In some embodiments, each $R_1$ is independently methyl, ethyl, propyl, or i-propyl. In other embodiments, each $R_1$ is independently is methyl or ethyl. In other embodiments, each $R_1$ is independently is methyl. In other embodiments, each $R_1$ is independently is $(C_1-C_4)$ haloalkyl (e.g., $CF_3$, $CHF_2$, $CH_2CF_3$, or $CF_2CF_3$).

In some embodiments, each $R_2$ is independently $(C_1-C_3)$ alkyl, $(C_1-C_3)$ haloalkyl, $(C_1-C_3)$ alkoxy, $(C_1-C_3)$ haloalkoxy, halogen, OH, or $NH_2$. In other embodiments, each $R_2$ is independently $(C_1-C_3)$ alkyl, $(C_1-C_3)$ haloalkyl, halogen, OH, or $NH_2$. In other embodiments, each $R_2$ is independently halogen, OH, or $NH_2$. In other embodiments, each $R_2$ is independently $(C_1-C_3)$ alkyl or $(C_1-C_3)$ haloalkyl. In other embodiments, each $R_2$ is independently $(C_1-C_3)$ alkyl, $(C_1-C_3)$ haloalkyl, $(C_1-C_3)$ alkoxy, or $(C_1-C_3)$ haloalkoxy. In other embodiments, each $R_2$ is independently $(C_1-C_3)$ alkyl or halogen.

In some embodiments, each $R_3$ is independently ($C_1$-$C_3$) alkyl, ($C_1$-$C_3$) haloalkyl, ($C_1$-$C_3$) alkoxy, ($C_1$-$C_3$) haloalkoxy, halogen, OH, or $NH_2$. In other embodiments, each $R_3$ is independently ($C_1$-$C_3$) alkyl, ($C_1$-$C_3$) haloalkyl, halogen, OH, or $NH_2$. In other embodiments, each $R_3$ is independently halogen, OH, or $NH_2$. In other embodiments, each $R_3$ is independently ($C_1$-$C_3$) alkyl or ($C_1$-$C_3$) haloalkyl. In other embodiments, each $R_3$ is independently ($C_1$-$C_3$) alkyl, ($C_1$-$C_3$) haloalkyl, ($C_1$-$C_3$) alkoxy, or ($C_1$-$C_3$) haloalkoxy. In other embodiments, each $R_3$ is independently ($C_1$-$C_3$) alkyl or halogen.

In some embodiments, each $R_4$ is independently ($C_1$-$C_3$) alkyl, ($C_1$-$C_3$) haloalkyl, ($C_1$-$C_3$) alkoxy, ($C_1$-$C_3$) haloalkoxy, halogen, OH, or $NH_2$. In other embodiments, each $R_4$ is independently ($C_1$-$C_3$) alkyl, ($C_1$-$C_3$) haloalkyl, halogen, OH, or $NH_2$. In other embodiments, each $R_4$ is independently halogen, OH, or $NH_2$. In other embodiments, each $R_4$ is independently ($C_1$-$C_3$) alkyl or ($C_1$-$C_3$) haloalkyl. In other embodiments, each $R_4$ is independently ($C_1$-$C_3$) alkyl, ($C_1$-$C_3$) haloalkyl, ($C_1$-$C_3$) alkoxy, or ($C_1$-$C_3$) haloalkoxy. In other embodiments, each $R_4$ is independently ($C_1$-$C_3$) alkyl or halogen. In other embodiments, each $R_4$ is independently methyl, ethyl, propyl, trifluoromethyl, or difluoromethyl. In other embodiments, each $R_4$ is independently trifluoromethyl or difluoromethyl. In other embodiments, at least one $R_4$ is trifluoromethyl.

In some embodiments, t is 0. In other embodiments, t is 1. In other embodiments, t is 2. In other embodiments, t is 3. In other embodiments, t is 0 or 1. In other embodiments, t is 1 or 2. In other embodiments, t is 0, 1 or 2. In other embodiments, t is 1, 2 or 3.

In some embodiments, n is 0. In other embodiments, n is 1. In other embodiments, n is 2. In other embodiments, n is 3. In other embodiments, n is 0 or 1. In other embodiments, n is 1 or 2. In other embodiments, n is 0, 1 or 2. In other embodiments, n is 1, 2 or 3.

In some embodiments, o is 0. In other embodiments, o is 1. In other embodiments, o is 2. In other embodiments, o is 3. In other embodiments, o is 0 or 1. In other embodiments, o is 1 or 2. In other embodiments, o is 0, 1 or 2. In other embodiments, o is 1, 2 or 3.

In some embodiments, r is 0. In other embodiments, r is 1. In other embodiments, r is 2. In other embodiments, r is 3. In other embodiments, r is 0 or 1. In other embodiments, r is 1 or 2. In other embodiments, r is 0, 1 or 2. In other embodiments, r is 1, 2 or 3.

Any of the groups described herein for any of A, X, $X_2$, $X_3$, $X_4$, $R_1$, $R_2$, $R_3$, $R_4$, n, o, r, and t can be combined with any of the groups described herein for one or more of the remainder of A, X, $X_2$, $X_3$, $X_4$, $R_1$, $R_2$, $R_3$, $R_4$, n, o, r, and t, and may further be combined with any of the groups described herein for the Linker.

For a Targeting Ligand of Formula TL-I:

(1) In one embodiment, X is N and A is

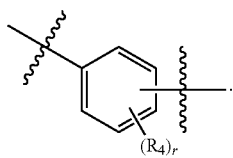

(2) In one embodiment, X is N and A is

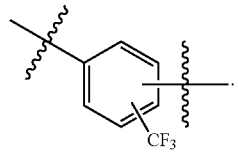

(3) In one embodiment, X is N and $X_2$ is N.
(4) In one embodiment, X is N and $X_3$ is N.
(5) In one embodiment, X is N, $X_2$ is N, and $X_3$ is N.
(6) In one embodiment, X is N, $X_2$ is N, $X_3$ is N, and A is

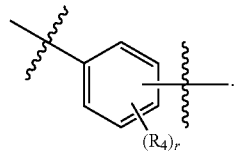

(7) In one embodiment, X is N, $X_2$ is N, $X_3$ is N, and A is

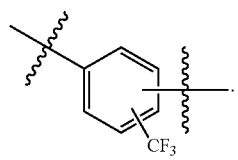

(8) In one embodiment, X is N, $X_2$ is N, $X_3$ is N, A is

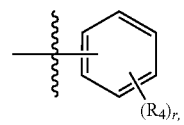

and o is 0.
(9) In one embodiment, X is N, $X_2$ is N, $X_3$ is N, A is

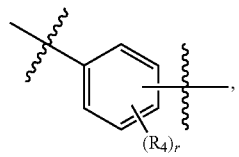

and n is 0.
(10) In one embodiment, X is N, $X_2$ is N, $X_3$ is N, A is

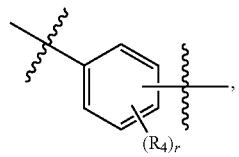

and t is 0.

(11) In one embodiment, X is N, $X_2$ is N, $X_3$ is N, A is

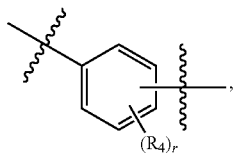

and r is 1.

(12) In one embodiment, X is N, $X_2$ is N, $X_3$ is N, A is

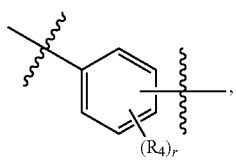

o is 0, and n is 0.

(13) In one embodiment, X is N, $X_2$ is N, $X_3$ is N, A is

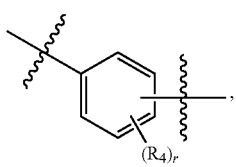

is 0, n is 0, and t is 0.

(14) In one embodiment, X is N, $X_2$ is N, $X_3$ is N, A is

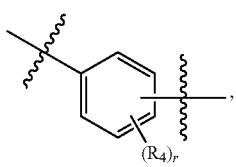

is 0, n is 0, t is 0, and r is 1.

(15) In one embodiment, X is N, $X_2$ is N, $X_3$ is N, r is 1, and $R_4$ is ($C_1$-$C_4$) haloalkyl.

(16) In one embodiment, X is N, $X_2$ is N, $X_3$ is N, r is 1, and $R_4$ is $CF_3$.

In one embodiment, the compound of Formula TL-I is of Formula IL-Ia or TL-Ib:

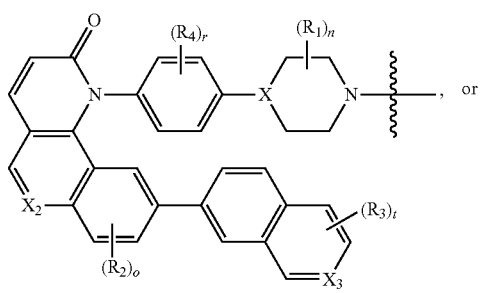

wherein X, $X_2$, $X_3$, $R_1$, $R_2$, $R_3$, $R_4$, n, o, t, and r are each as defined above in Formula TL-I.

For a Targeting Ligand of Formula TL-Ia or TL-Ib:

(1) In one embodiment, X is N and $X_2$ is N.

(2) In one embodiment, X is N and $X_3$ is N.

(3) In one embodiment, X is N, $X_2$ is N, and $X_3$ is N.

(4) In one embodiment, X is N, $X_2$ is N, $X_3$ is N, and o is 0.

(5) In one embodiment, X is N, $X_2$ is N, $X_3$ is N, and n is 0.

(6) In one embodiment, X is N, $X_2$ is N, $X_3$ is N, and t is 0.

(7) In one embodiment, X is N, $X_2$ is N, $X_3$ is N, and r is 1.

(8) In one embodiment, X is N, $X_2$ is N, $X_3$ is N, o is 0, and n is 0.

(9) In one embodiment, X is N, $X_2$ is N, $X_3$ is N, o is 0, n is 0, and t is 0.

(10) In one embodiment, X is N, $X_2$ is N, $X_3$ is N, o is 0, n is 0, t is 0, and r is 1.

(11) In one embodiment, X is N, $X_2$ is N, $X_3$ is N, r is 1, and $R_4$ is ($C_1$-$C_4$) haloalkyl.

(12) In one embodiment, X is N, $X_2$ is N, $X_3$ is N, r is 1, and $R_4$ is $CF_3$.

X, $X_2$, $X_3$, $R_1$, $R_2$, $R_3$, $R_4$, n, o, t, and r can each be selected from any of the groups and combined as described above in Formula TL-I.

In another embodiment, the compound of Formula TL-I is of Formula TL-Ic or TL-Id:

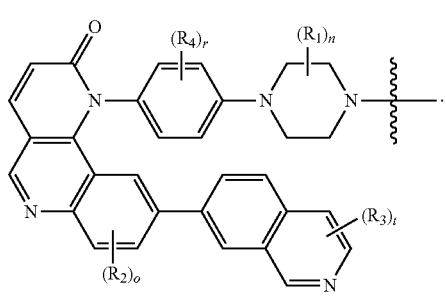

(TL-Id)

wherein X, $R_1$, $R_2$, $R_3$, $R_4$, n, o, t, and r are each as defined above in Formula TL-I.

For a Targeting Ligand of Formula TL-Ic or TL-Id:
(1) In one embodiment, X is N and o is 0.
(2) In one embodiment, X is N and n is 0.
(3) In one embodiment, X is N and t is 0.
(4) In one embodiment, X is N and r is 1.
(5) In one embodiment, X is N, o is 0, and n is 0.
(6) In one embodiment, X is N, o is 0, n is 0, and t is 0.
(7) In one embodiment, X is N, o is 0, n is 0, t is 0, and r is 1.
(8) In one embodiment, X is N, r is 1, and $R_4$ is $(C_1\text{-}C_4)$ haloalkyl.
(9) In one embodiment, X is N, r is 1, and $R_4$ is $CF_3$.

X, $R_2$, $R_3$, $R_4$, n, o, t, and r can each be selected from any of the groups and combined as described above in Formula TL-I.

In another embodiment, the compound of Formula TL-I is of Formula TL-Ie or IL-If:

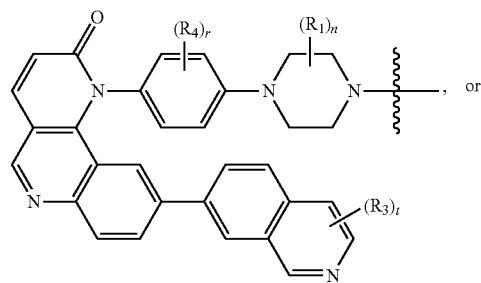

(TL-Ie)

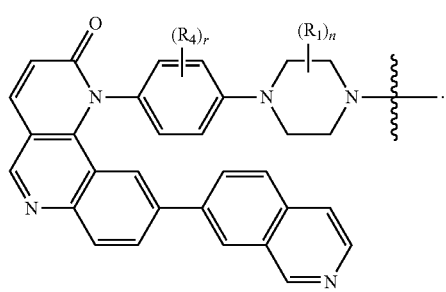

(TL-If)

wherein $R_1$, $R_3$, $R_4$, n, t, and r are each as defined above in Formula TL-I.

For a Targeting Ligand of Formula TL-Ie or TL-If:
(1) In one embodiment, n is 0.
(2) In one embodiment, t is 0.
(3) In one embodiment, r is 1.
(4) In one embodiment, n is 0 and t is 0.
(5) In one embodiment, n is 0, t is 0, and r is 1.

(6) In one embodiment, r is 1 and $R_4$ is $(C_1\text{-}C_4)$ haloalkyl.
(7) In one embodiment, r is 1 and $R_4$ is $CF_3$.

$R_1$, $R_3$, $R_4$, n, t, and r can each be selected from any of the groups and combined as described above in Formula TL-I.

In one embodiment, a Targeting Ligand is a compound of Formula TL-II:

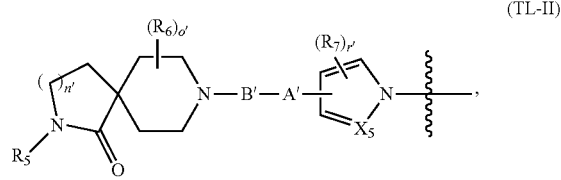

(TL-II)

or an enantiomer, diastereomer, stereoisomer, or pharmaceutically acceptable salt thereof,
wherein:
A' is

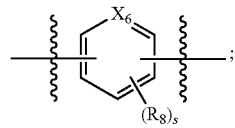

B' is

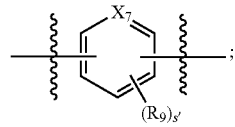

$X_5$ is N or CH;
$X_6$ is N or CH;
$X_7$ is N or CH;
$R_5$ is H or $(C_1\text{-}C_4)$ alkyl;
each $R_6$ is independently $(C_1\text{-}C_4)$ alkyl or $(C_1\text{-}C_4)$ haloalkyl;
each $R_7$ is independently $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, or halogen;
each $R_8$ is independently $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, halogen, OH, or $NH_2$;
each $R_9$ is independently $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, halogen, OH, or $NH_2$;
n' is 1 or 2;
r' is 0, 1, or 2; and
o', s, and s' are each independently 0, 1, 2, or 3;
wherein the Targeting Ligand is bonded to the Linker via the

next to

In some embodiments, A' is

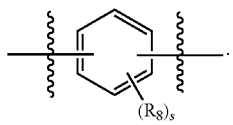

In other embodiments, A' is

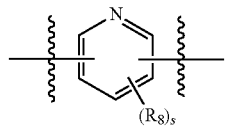

In some embodiments, B' is

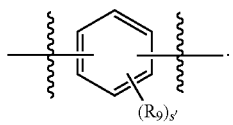

In other embodiments, B' is

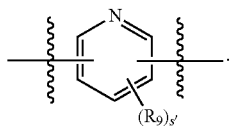

In some embodiments, $X_5$ is N. In other embodiments, $X_5$ is CH.

In some embodiments, $X_6$ is N. In other embodiments, $X_6$ is CH.

In some embodiments, $X_7$ is N. In other embodiments, $X_7$ is CH.

In some embodiments, $R_5$ is H or $(C_1-C_3)$ alkyl. In other embodiments, $R_5$ is H or methyl, ethyl, propyl, or i-propyl. In other embodiments, $R_5$ is H, methyl, or ethyl. In other embodiments, $R_5$ is H or methyl. In other embodiments, $R_5$ is H.

In some embodiments, each $R_6$ is independently $(C_1-C_3)$ alkyl or $(C_1-C_3)$ haloalkyl. In other embodiments, each $R_6$ is independently $(C_1-C_3)$ alkyl. In other embodiments, each $R_6$ is independently $(C_1-C_3)$ haloalkyl. In other embodiments, each $R_6$ is independently $(C_1-C_2)$ alkyl or $(C_1-C_2)$ haloalkyl.

In some embodiments, each $R_7$ is independently $(C_1-C_3)$ alkyl, $(C_1-C_3)$ haloalkyl, $(C_1-C_3)$ alkoxy, $(C_1-C_3)$ haloalkoxy, or halogen. In other embodiments, each $R_7$ is independently $(C_1-C_3)$ alkyl or $(C_1-C_3)$ haloalkyl. In other embodiments, each $R_7$ is independently $(C_1-C_3)$ alkyl, $(C_1-C_3)$ haloalkyl, or halogen. In other embodiments, each $R_7$ is independently $(C_1-C_3)$ alkyl. In other embodiments, each $R_7$ is independently halogen. In other embodiments, each $R_7$ is independently $(C_1-C_3)$ alkyl, $(C_1-C_3)$ haloalkyl, $(C_1-C_3)$ alkoxy, or $(C_1-C_3)$ haloalkoxy. In other embodiments, each $R_7$ is $(C_1-C_3)$ alkoxy, $(C_1-C_3)$ haloalkoxy, or halogen.

In some embodiments, each $R_8$ is independently $(C_1-C_3)$ alkyl, $(C_1-C_3)$ haloalkyl, $(C_1-C_3)$ alkoxy, $(C_1-C_3)$ haloalkoxy, halogen, OH, or $NH_2$. In other embodiments, each $R_8$ is independently halogen, OH, or $NH_2$. In other embodiments, each $R_8$ is independently $(C_1-C_3)$ alkyl, $(C_1-C_3)$ haloalkyl, $(C_1-C_3)$ alkoxy, $(C_1-C_3)$ haloalkoxy, or halogen. In other embodiments, each $R_8$ is independently $(C_1-C_3)$ alkyl, $(C_1-C_3)$ haloalkyl, $(C_1-C_3)$ alkoxy, or $(C_1-C_3)$ haloalkoxy. In other embodiments, each $R_8$ is independently $(C_1-C_3)$ alkyl or $(C_1-C_3)$ haloalkyl. In other embodiments, each $R_8$ is independently $(C_1-C_3)$ alkoxy or $(C_1-C_3)$ haloalkoxy. In other embodiments, each $R_8$ is independently halogen.

In some embodiments, each $R_9$ is independently $(C_1-C_3)$ alkyl, $(C_1-C_3)$ haloalkyl, $(C_1-C_3)$ alkoxy, $(C_1-C_3)$ haloalkoxy, halogen, OH, or $NH_2$. In other embodiments, each $R_9$ is independently halogen, OH, or $NH_2$. In other embodiments, each $R_9$ is independently $(C_1-C_3)$ alkyl, $(C_1-C_3)$ haloalkyl, $(C_1-C_3)$ alkoxy, $(C_1-C_3)$ haloalkoxy, or halogen. In other embodiments, each $R_9$ is independently $(C_1-C_3)$ alkyl, $(C_1-C_3)$ haloalkyl, $(C_1-C_3)$ alkoxy, or $(C_1-C_3)$ haloalkoxy. In other embodiments, each $R_9$ is independently $(C_1-C_3)$ alkyl or $(C_1-C_3)$ haloalkyl. In other embodiments, each $R_9$ is independently $(C_1-C_3)$ alkoxy or $(C_1-C_3)$ haloalkoxy. In other embodiments, each $R_9$ is independently halogen. In other embodiments, at least one $R_9$ is Cl.

In some embodiments, o' is 0. In other embodiments, o' is 1. In other embodiments, o' is 2. In other embodiments, o' is 3. In other embodiments, o' is 0 or 1. In other embodiments, o' is 1 or 2. In other embodiments, o' is 0, 1 or 2. In other embodiments, o' is 1, 2, or 3.

In some embodiments, s is 0. In other embodiments, s is 1. In other embodiments, s is 2. In other embodiments, s is 3. In other embodiments, s is 0 or 1. In other embodiments, s is 1 or 2. In other embodiments, s is 0, 1 or 2. In other embodiments, s is 1, 2, or 3.

In some embodiments, s' is 0. In other embodiments, s' is 1. In other embodiments, s' is 2. In other embodiments, s' is 3. In other embodiments, s' is 0 or 1. In other embodiments, s' is 1 or 2. In other embodiments, s' is 0, 1 or 2. In other embodiments, s' is 1, 2, or 3.

In some embodiments, r' is 0. In other embodiments, r' is 1. In other embodiments, r' is 2. In other embodiments, r' is 0 or 1. In other embodiments, r' is 1 or 2.

In other embodiments, n' is 1. In other embodiments, n' is 2.

Any of the groups described herein for any of A', B', $X_5$, $X_6$, $X_7$, $R_5$, $R_6$, $R_7$, $R_8$, $R_9$, n', o', r', s, and s' can be combined with any of the groups described herein for one or more of the remainder of A', B', $X_5$, $X_6$, $X_7$, $R_5$, $R_6$, $R_7$, $R_8$, $R_9$, n', o', r', s, and s', and may further be combined with any of the groups described herein for the Linker.

For a Targeting Ligand of Formula TL-II:
(1) In one embodiment, $X_5$ is N and A' is

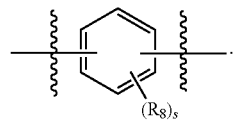

(2) In one embodiment, $X_5$ is N and B' is

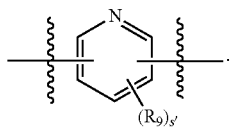

(3) In one embodiment, $X_5$ is N, A' is

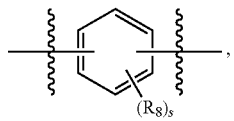

and $R_5$ is H.

(4) In one embodiment, $X_5$ is N, B' is

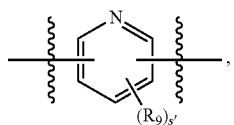

and $R_5$ is H.

(5) In one embodiment, $X_5$ is N, A' is

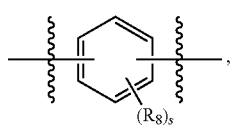

and B' is

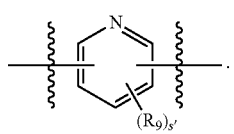

(6) In one embodiment, $X_5$ is N, A' is

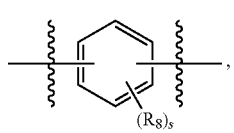

B' is

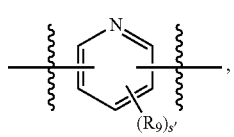

and $R_5$ is H.

(7) In one embodiment, $X_5$ is N and n' is 1.
(8) In one embodiment, $X_5$ is N and o' is 0.
(9) In one embodiment, $X_5$ is N and r' is 0.
(10) In one embodiment, $X_5$ is N, n' is 1, and o' is 0.
(11) In one embodiment, $X_5$ is N, n' is 1, and r' is 0.
(12) In one embodiment, $X_5$ is N, n' is 1, o' is 0, and r' is 0.
(13) In one embodiment, $X_5$ is N, n' is 1, o' is 0, r' is 0, and s is 0.
(14) In one embodiment, $X_5$ is N, A' is

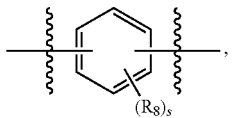

B' is

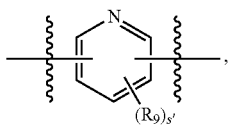

$R_5$ is H, and $R_9$ is halogen.

(15) In one embodiment, $X_5$ is N, A' is

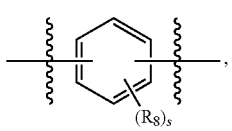

B' is

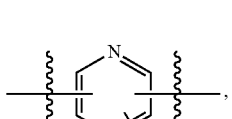

$R_5$ is H, $R_9$ is halogen, and n' is 1.

(16) In one embodiment, $X_5$ is N, A' is

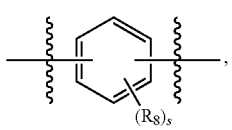

B' is

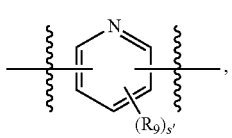

$R_5$ is H, $R_9$ is halogen, n' is 1, and o' is 0.

(17) In one embodiment, $X_5$ is N, A' is

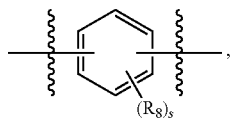

B' is

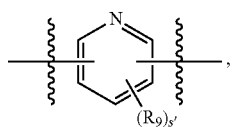

$R_5$ is H, $R_9$ is halogen, n' is 1, o' is 0, and r' is 0.
(18) In one embodiment, $X_5$ is N, A' is

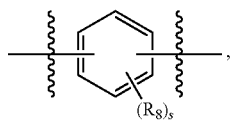

B' is

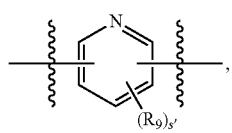

$R_5$ is H, and n' is 1.
(19) In one embodiment, $X_5$ is N, A' is

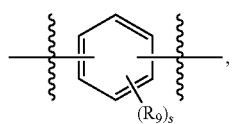

B' is

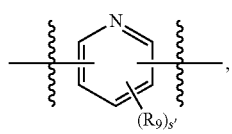

$R_5$ is H, n' is 1, and o' is 0.
(20) In one embodiment, $X_5$ is N, A' is

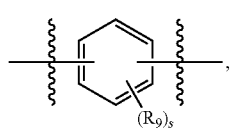

B' is

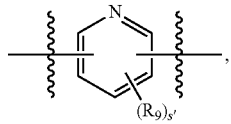

$R_5$ is H, n' is 1, o' is 0, and r' is 0.

In one embodiment, the compound of Formula TL-II is of Formula TL-IIa or TL-IIb:

(TL-IIa)

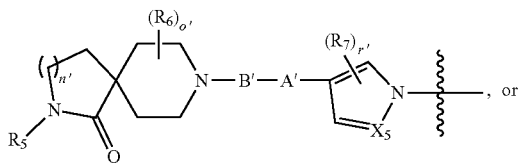

, or (TL-IIb)

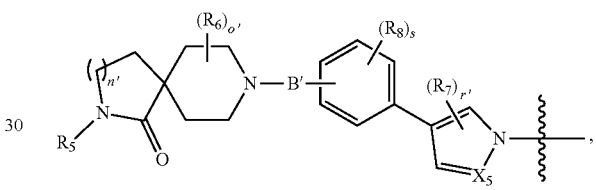

wherein A', B', $X_5$, $R_5$, $R_6$, $R_7$, n', o', and r' are each as defined above in Formula TL-II.

For a Targeting Ligand of Formula TL-IIa or TL-IIb:
(1) In one embodiment, $X_5$ is N and A' is

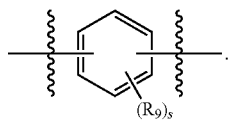

(2) In one embodiment, $X_5$ is N and B' is

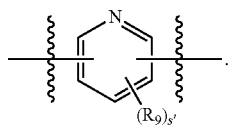

(3) In one embodiment, $X_5$ is N, A' is

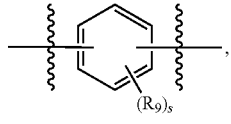

and $R_5$ is H.

(4) In one embodiment, $X_5$ is N, B' is

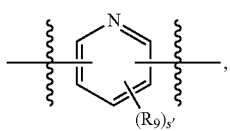

and $R_5$ is H.

(5)

(6) In one embodiment, $X_5$ is N, A' is

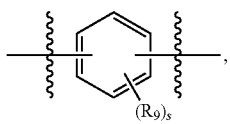

and B' is

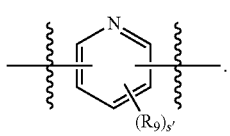

(7) In one embodiment, $X_5$ is N, A' is

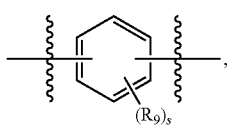

B' is

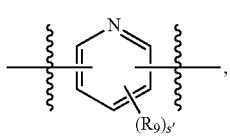

and $R_5$ is H.

(8) In one embodiment, $X_5$ is N and n' is 1.
(9) In one embodiment, $X_5$ is N and o' is 0.
(10) In one embodiment, $X_5$ is N and r' is 0.
(11) In one embodiment, $X_5$ is N, n' is 1, and o' is 0.
(12) In one embodiment, $X_5$ is N, n' is 1, and r' is 0.
(13) In one embodiment, $X_5$ is N, n' is 1, o' is 0, and r' is 0.
(14) In one embodiment, $X_5$ is N, n' is 1, o' is 0, r' is 0, and s is 0.
(15) In one embodiment, $X_5$ is N, A' is

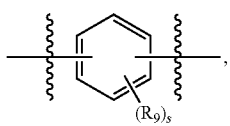

B' is

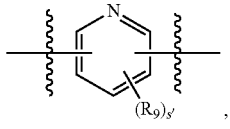

$R_5$ is H, and $R_9$ is halogen.

(16) In one embodiment, $X_5$ is N, A' is

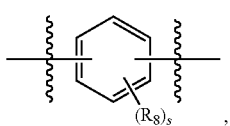

B' is

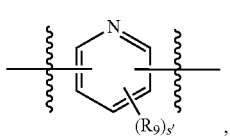

$R_5$ is H, $R_9$ is halogen, and n' is 1.

(17) In one embodiment, $X_5$ is N, A' is

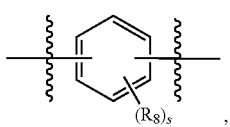

B' is

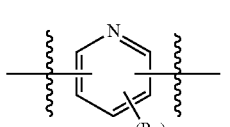

$R_5$ is H, $R_9$ is halogen, n' is 1, and o' is 0.

(18) In one embodiment, $X_5$ is N, A' is

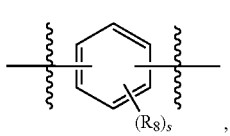

B' is

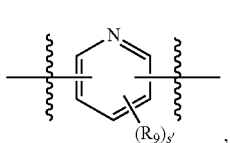

$R_5$ is H, $R_9$ is halogen, n' is 1, o' is 0, and r' is 0.

(19) In one embodiment, $X_5$ is N, A' is

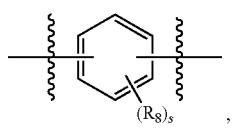

B' is

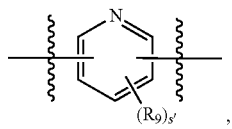

$R_5$ is H, and n' is 1.

(20) In one embodiment, $X_5$ is N, A' is

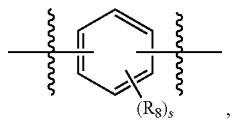

B' is

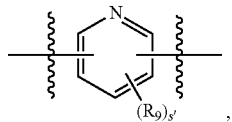

$R_5$ is H, n' is 1, and o' is 0.

(21) In one embodiment, $X_5$ is N, A' is

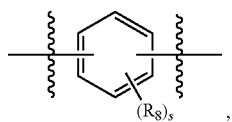

B' is

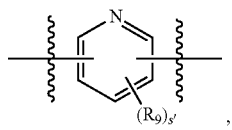

$R_5$ is H, n' is 1, o' is 0, and r' is 0.

In one embodiment, the compound of Formula TL-II is of Formula TL-IIc or TL-IId:

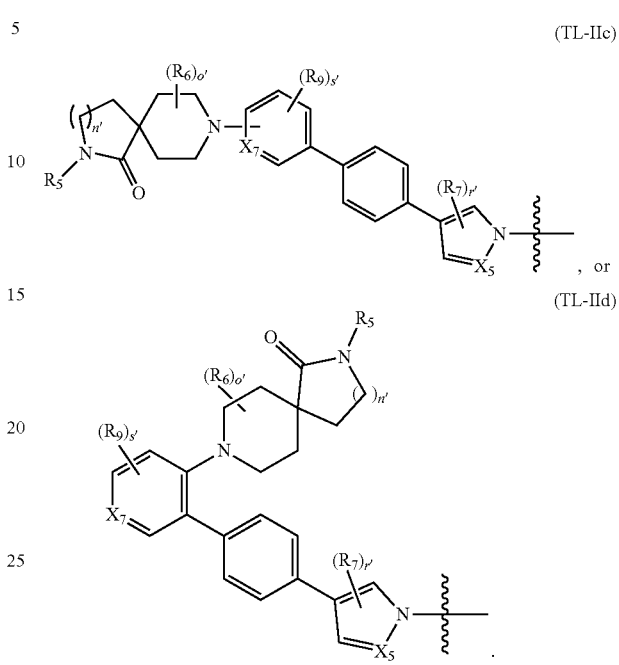

wherein $X_5$, $X_7$, $R_5$, $R_6$, $R_7$, $R_9$, n', o', r', and s' are each as defined above in Formula TL-II.

For a Targeting Ligand of Formula TL-IIc or TL-IId:

(1) In one embodiment, $X_5$ is N.
(2) In one embodiment, $X_5$ is N and $R_5$ is H.
(3) In one embodiment, $X_5$ is N and n' is 1.
(4) In one embodiment, $X_5$ is N and o' is 0.
(5) In one embodiment, $X_5$ is N and r' is 0.
(6) In one embodiment, $X_5$ is N, n' is 1, and o' is 0.
(7) In one embodiment, $X_5$ is N, n' is 1, and r' is 0.
(8) In one embodiment, $X_5$ is N, n' is 1, o' is 0, and r' is 0.
(9) In one embodiment, $X_5$ is N, n' is 1, o' is 0, r' is 0, and s is 0.
(10) In one embodiment, $X_5$ is N, $R_5$ is H, and $R_9$ is halogen.
(11) In one embodiment, $X_5$ is N, $R_5$ is H, $R_9$ is halogen, and n' is 1.
(12) In one embodiment, $X_5$ is N, $R_5$ is H, $R_9$ is halogen, n' is 1, and o' is 0.
(13) In one embodiment, $X_5$ is N, $R_5$ is H, $R_9$ is halogen, n' is 1, o' is 0, and r' is 0.
(14) In one embodiment, $X_5$ is N, $R_5$ is H, and n' is 1.
(15) In one embodiment, $X_5$ is N, $R_5$ is H, n' is 1, and o' is 0.
(16) In one embodiment, $X_5$ is N, $R_5$ is H, n' is 1, o' is 0, and r' is 0.
(17) In one embodiment, $X_5$ is N, $R_5$ is H, n' is 1, o' is 0, r' is 0, and s' is 1.

In one embodiment, the compound of Formula TL-II is of Formula TL-IIc or TL-IId:

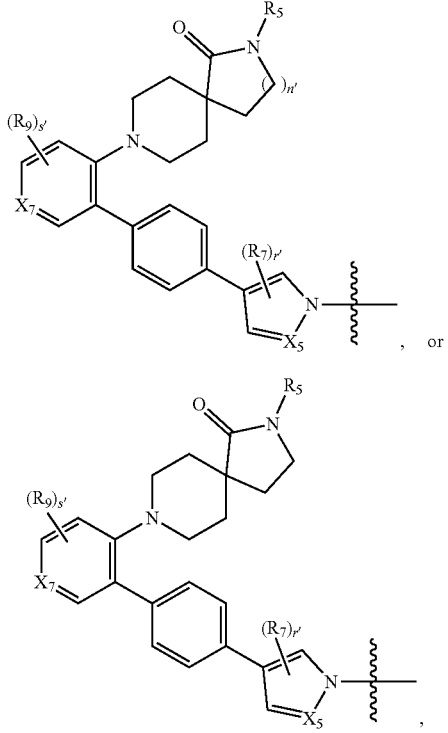

(TL-IIe)

(TL-IIf)

wherein $X_5$, $R_5$, $R_7$, $R_9$, n', r', and s' are each as defined above in Formula TL-II.

For a Targeting Ligand of Formula TL-IIe or TL-IIf:
(1) In one embodiment, $X_5$ is N.
(2) In one embodiment, $X_5$ is N and $R_5$ is H.
(3) In one embodiment, $X_5$ is N and n' is 1.
(4) In one embodiment, $X_5$ is N and s' is 1.
(5) In one embodiment, $X_5$ is N and r' is 0.
(6) In one embodiment, $X_5$ is N, n' is 1, and s' is 1.
(7) In one embodiment, $X_5$ is N, n' is 1, and r' is 0.
(8) In one embodiment, $X_5$ is N, n' is 1, s' is 1, and r' is 0.
(9) In one embodiment, $X_5$ is N, $R_5$ is H, and $R_9$ is halogen.
(10) In one embodiment, $X_5$ is N, $R_5$ is H, $R_9$ is halogen, and n' is 1.
(11) In one embodiment, $X_5$ is N, $R_5$ is H, $R_9$ is halogen, n' is 1, and r' is 0.
(12) In one embodiment, $X_5$ is N, $R_5$ is H, $R_9$ is halogen, n' is 1, r' is 0, and s' is 1.
(13) In one embodiment, $X_5$ is N, $R_5$ is H, and n' is 1.
(14) In one embodiment, $X_5$ is N, $R_5$ is H, n' is 1, and r' is 0.
(15) In one embodiment, $X_5$ is N, $R_5$ is H, n' is 1, r' is 0, and s' is 1.

Degron

The Degron serves to link a targeted protein, through a Linker and a Targeting Ligand, to a ubiquitin ligase for proteosomal degradation. In one embodiment, the Degron is capable of binding to a ubiquitin ligase, such as an E3 ubiquitin ligase. In one embodiment, the Degron is capable of binding to cereblon.

In one embodiment, the Degron is of Formula D1:

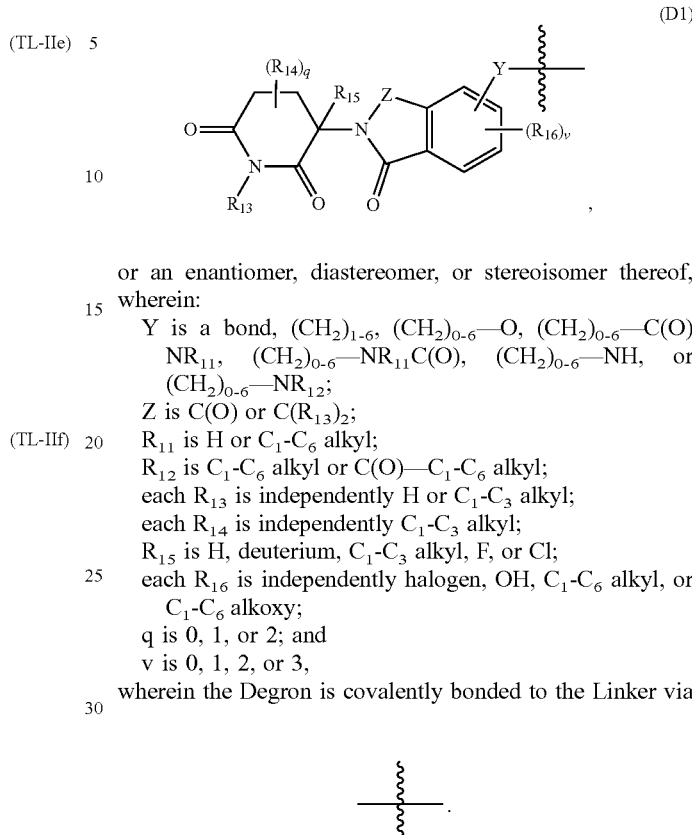

(D1)

or an enantiomer, diastereomer, or stereoisomer thereof, wherein:
Y is a bond, $(CH_2)_{1-6}$, $(CH_2)_{0-6}$—O, $(CH_2)_{0-6}$—C(O)NR$_{11}$, $(CH_2)_{0-6}$—NR$_{11}$C(O), $(CH_2)_{0-6}$—NH, or $(CH_2)_{0-6}$—NR$_{12}$;
Z is C(O) or C(R$_{13}$)$_2$;
R$_{11}$ is H or $C_1$-$C_6$ alkyl;
R$_{12}$ is $C_1$-$C_6$ alkyl or C(O)—$C_1$-$C_6$ alkyl;
each R$_{13}$ is independently H or $C_1$-$C_3$ alkyl;
each R$_{14}$ is independently $C_1$-$C_3$ alkyl;
R$_{15}$ is H, deuterium, $C_1$-$C_3$ alkyl, F, or Cl;
each R$_{16}$ is independently halogen, OH, $C_1$-$C_6$ alkyl, or $C_1$-$C_6$ alkoxy;
q is 0, 1, or 2; and
v is 0, 1, 2, or 3,
wherein the Degron is covalently bonded to the Linker via

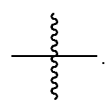

.

In one embodiment, Z is C(O).
In one embodiment, Z is C(R$_{13}$)$_2$; and each R$_{13}$ is H. In one embodiment, X is C(R$_{13}$)$_2$; and one of R$_{13}$ is H, and the other is $C_1$-$C_3$ alkyl selected from methyl, ethyl, and propyl.
In one embodiment, Z is C(R$_{13}$)$_2$; and each R$_{13}$ is independently selected from methyl, ethyl, and propyl.
In one embodiment, Y is a bond.
In one embodiment, Y is a bond, O, or NH.
In one embodiment, Y is $(CH_2)_1$, $(CH_2)_2$, $(CH_2)_3$, $(CH_2)_4$, $(CH_2)_5$, or $(CH_2)_6$. In one embodiment, Y is $(CH_2)_1$, $(CH_2)_2$, or $(CH_2)_3$. In one embodiment, Y is $(CH_2)_1$ or $(CH_2)_2$.
In one embodiment, Y is O, CH$_2$—O, $(CH_2)_2$—O, $(CH_2)_3$—O, $(CH_2)_4$—O, $(CH_2)_5$—O, or $(CH_2)_6$—O. In one embodiment, Y is O, CH$_2$—O, $(CH_2)_2$—O, or $(CH_2)_3$—O. In one embodiment, Y is O or CH$_2$—O. In one embodiment, Y is O.
In one embodiment, Y is C(O)NR$_{11}$, CH$_2$—C(O)NR$_{11}$, $(CH_2)_2$—C(O)NR$_{11}$, $(CH_2)_3$—C(O)NR$_{11}$, $(CH_2)_4$—C(O)NR$_{11}$, $(CH_2)_5$—C(O)NR$_{11}$, or $(CH_2)_6$—C(O)NR$_{11}$. In one embodiment, Y is C(O)NR$_{11}$, CH$_2$—C(O)NR$_{11}$, $(CH_2)_2$—C(O)NR$_{11}$, or $(CH_2)_3$—C(O)NR$_{11}$. In one embodiment, Y is C(O)NR$_{11}$ or CH$_2$—C(O)NR$_{11}$. In one embodiment, Y is C(O)NR$_{11}$.
In one embodiment, Y is NR$_{11}$C(O), CH$_2$—NR$_{11}$C(O), $(CH_2)_2$—NR$_{11}$C(O), $(CH_2)_3$—NR$_{11}$C(O), $(CH_2)_4$—NR$_{11}$C(O), $(CH_2)_5$—NR$_{11}$C(O), or $(CH_2)_6$—NR$_{11}$C(O). In one embodiment, Y is NR$_{11}$C(O), CH$_2$—NR$_{11}$C(O), $(CH_2)_2$—NR$_{11}$C(O), or $(CH_2)_3$—NR$_{11}$C(O). In one embodiment, Y is NR$_{11}$C(O) or CH$_2$—NR$_{11}$C(O). In one embodiment, Y is NR$_{11}$C(O).

In one embodiment, $R_{11}$ is H. In one embodiment, $R_{11}$ is selected from methyl, ethyl, propyl, butyl, i-butyl, t-butyl, pentyl, i-pentyl, and hexyl. In one embodiment, $R_{11}$ is $C_1$-$C_3$ alkyl selected from methyl, ethyl, and propyl.

In one embodiment, Y is NH, $CH_2$—NH, $(CH_2)_2$—NH, $(CH_2)_3$—NH, $(CH_2)_4$—NH, $(CH_2)_5$—NH, or $(CH_2)_6$—NH. In one embodiment, Y is NH, $CH_2$—NH, $(CH_2)_2$—NH, or $(CH_2)_3$—NH. In one embodiment, Y is NH or $CH_2$—NH. In one embodiment, Y is NH.

In one embodiment, Y is $NR_{12}$, $CH_2$—$NR_{12}$, $(CH_2)_2$—$NR_{12}$, $(CH_2)_3$—$NR_{12}$, $(CH_2)_4$—$NR_{12}$, $(CH_2)_5$—$NR_{12}$, or $(CH_2)_6$—$NR_{12}$. In one embodiment, Y is $NR_{12}$, $CH_2$—$NR_{12}$, $(CH_2)_2$—$NR_{12}$, or $(CH_2)_3$—$NR_{12}$. In one embodiment, Y is $NR_{12}$ or $CH_2$—$NR_{12}$. In one embodiment, Y is $NR_{12}$.

In one embodiment, $R_{12}$ is selected from methyl, ethyl, propyl, butyl, i-butyl, t-butyl, pentyl, i-pentyl, and hexyl. In one embodiment, $R_{12}$ is $C_1$-$C_3$ alkyl selected from methyl, ethyl, and propyl.

In one embodiment, $R_{12}$ is selected from C(O)-methyl, C(O)-ethyl, C(O)-propyl, C(O)-butyl, C(O)-i-butyl, C(O)-t-butyl, C(O)-pentyl, C(O)-i-pentyl, and C(O)-hexyl. In one embodiment, $R_{12}$ is C(O)—$C_1$-$C_3$ alkyl selected from C(O)-methyl, C(O)-ethyl, and C(O)-propyl.

In one embodiment, $R_{13}$ is H.

In one embodiment, $R_{13}$ is $C_1$-$C_3$ alkyl selected from methyl, ethyl, and propyl. In one embodiment, $R_{13}$ is methyl.

In one embodiment, q is 0.
In one embodiment, q is 1.
In one embodiment, q is 2.
In one embodiment, each $R_{14}$ is independently $C_1$-$C_3$ alkyl selected from methyl, ethyl, and propyl.
In one embodiment, v is 0.
In one embodiment, v is 1.
In one embodiment, v is 2.
In one embodiment, v is 3.

In one embodiment, each $R_{16}$ is independently selected from halogen (e.g., F, Cl, Br, and I), OH, $C_1$-$C_6$ alkyl (e.g., methyl, ethyl, propyl, butyl, i-butyl, t-butyl, pentyl, i-pentyl, and hexyl), and $C_1$-$C_6$ alkoxy (e.g., methoxy, ethoxy, propoxy, butoxy, i-butoxy, t-butoxy, and pentoxy). In a further embodiment, each $R_{16}$ is independently selected from F, Cl, OH, methyl, ethyl, propyl, butyl, i-butyl, t-butyl, methoxy, and ethoxy.

In one embodiment, $R_{15}$ is H, deuterium, or $C_1$-$C_3$ alkyl. In another embodiment, $R_{15}$ is H or $C_1$-$C_3$ alkyl. In a further embodiment, $R_{15}$ is in the (S) or (R) configuration. In a further embodiment, $R_{15}$ is in the (S) configuration. In one embodiment, the compound comprises a racemic mixture of (S)—$R_{15}$ and (R)—$R_{15}$.

In one embodiment, $R_{15}$ is H.
In one embodiment, $R_{15}$ is deuterium.
In one embodiment, $R_{15}$ is $C_1$-$C_3$ alkyl selected from methyl, ethyl, and propyl. In one embodiment, $R_{15}$ is methyl.

In one embodiment, $R_{15}$ is F or Cl. In a further embodiment, $R_{15}$ is in the (S) or (R) configuration. In a further embodiment, $R_{15}$ is in the (R) configuration. In one embodiment, the compound comprises a racemic mixture of (S)—$R_{15}$ and (R)—$R_{15}$. In one embodiment, $R_{15}$ is F.

Any of the groups described herein for any of Y, Z, $R_{11}$, $R_{12}$, $R_{13}$, $R_{14}$, $R_{15}$, $R_{16}$, q and v can be combined with any of the groups described herein for one or more of the remainder of Y, Z, $R_{11}$, $R_{12}$, $R_{13}$, $R_{14}$, $R_{15}$, $R_{16}$, q and v, and may further be combined with any of the groups described herein for the Linker.

For a Degron of Formula D1:
(1) In one embodiment, Z is C(O) and Y is a bond.
(2) In one embodiment, Z is C(O) and Y is NH.
(3) In one embodiment, Z is C(O) and Y is $(CH_2)_{0-6}$—O. In a further embodiment, Y is O.
(4) In one embodiment, Z is C(O); Y is a bond; and q and v are each 0.
(5) In one embodiment, Z is C(O); Y is NH; and q and v are each 0.
(6) In one embodiment, Z is C(O); Y is $(CH_2)_{0-6}$—O; and q and v are each 0. In a further embodiment, Y is O.
(7) In one embodiment, Z is C(O); Y is a bond; and $R_{13}$ is H.
(8) In one embodiment, Z is C(O); Y is a bond; and $R_{15}$ is H.
(9) In one embodiment, Z is C(O); Y is NH; and $R_{13}$ is H.
(10) In one embodiment, Z is C(O); Y is NH; and $R_{15}$ is H.
(11) In one embodiment, Z is C(O); Y is a bond; $R_{13}$ is H; and $R_{15}$ is H.
(12) In one embodiment, Z is C(O); Y is NH; $R_{13}$ is H; and $R_{15}$ is H.
(13) In one embodiment, Z is C(O); Y is $(CH_2)_{0-6}$—O; and $R_{13}$ is H. In a further embodiment, Y is O.
(14) In one embodiment, Z is C(O); Y is $(CH_2)_{0-6}$—O; and $R_{15}$ is H. In a further embodiment, Y is O.
(15) In one embodiment, Z is C(O); Y is $(CH_2)_{0-6}$—O; $R_{13}$ is H; and $R_{15}$ is H. In a further embodiment, Y is O.
(16) In one embodiment, q and v are each 0; and Y, Z, $R_{13}$, $R_{15}$, and $R_{16}$ are each as defined in any of (1)-(3) and (7)-(15).

In one embodiment, the Degron is of Formula D1a or D1b:

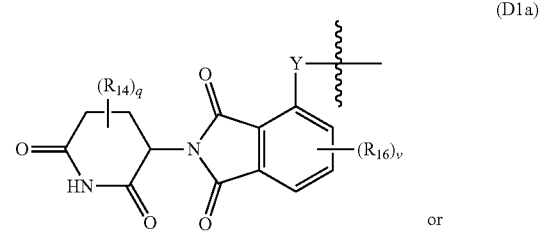

(D1a)

or

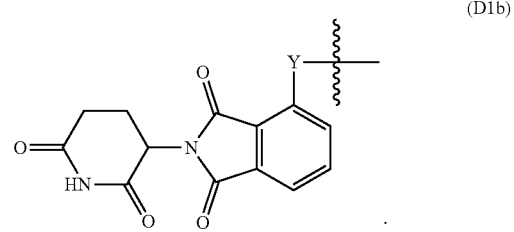

(D1b)

or an enantiomer, diastereomer, or stereoisomer thereof, wherein Y, $R_{14}$, $R_{16}$, q, and v are each as defined above in Formula D1, and can be selected from any moieties or combinations thereof described above.

In one embodiment, Y is a bond, O, or NH. In one embodiment, Y is a bond. In one embodiment, Y is O. In one embodiment, Y is NH.

In one embodiment, the Degron is of Formula D2:

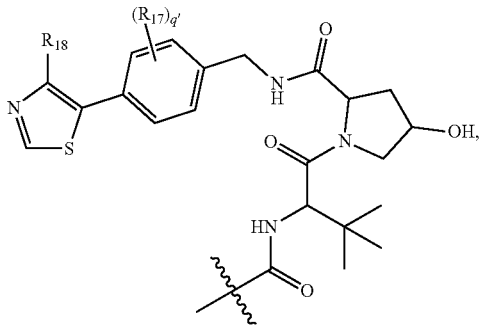

(D2)

or an enantiomer, diastereomer, or stereoisomer thereof, wherein:

each $R_{17}$ is independently $C_1$-$C_3$ alkyl;

q' is 0, 1, 2, 3 or 4; and $R_{18}$ is H or $C_1$-$C_3$ alkyl, wherein the Degron is covalently bonded to another moiety (e.g., a compound, or a Linker) via

In one embodiment, q' is 0.

In one embodiment, q' is 1.

In one embodiment, q' is 2.

In one embodiment, q' is 3.

In one embodiment, each $R_{17}$ is independently $C_1$-$C_3$ alkyl selected from methyl, ethyl, and propyl.

In one embodiment, Rig is methyl, ethyl, or propyl. In one embodiment, $R_{18}$ is methyl.

In one embodiment, the Degron is of Formula D2a or D2b:

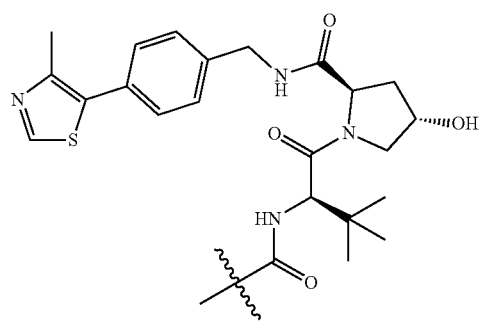

(D2a)

or

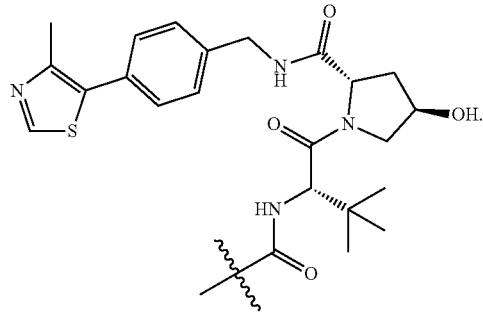

(D2b)

Linker

The Linker is a bond or a carbon chain that serves to link a Targeting Ligand with a Degron. In one embodiment, the carbon chain optionally comprises one, two, three, or more heteroatoms selected from N, O, and S. In one embodiment, the carbon chain comprises only saturated chain carbon atoms. In one embodiment, the carbon chain optionally comprises two or more unsaturated chain carbon atoms (e.g., C=C or C≡C). In one embodiment, one or more chain carbon atoms in the carbon chain are optionally substituted with one or more substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl$)_2$, CN, $C_3$-$C_8$ cycloalkyl, heterocyclyl, phenyl, and heteroaryl).

In one embodiment, the Linker comprises at least 5 chain atoms (e.g., C, O, N, and S). In one embodiment, the Linker comprises less than 25 chain atoms (e.g., C, O, N, and S). In one embodiment, the Linker comprises less than 20 chain atoms (e.g., C, O, N, and S). In one embodiment, the Linker comprises 4, 5, 6, 7, 8, 9, 10, 11, 12, 13, 14, 15, 16, 17, 18, 19, 20, 21, 22, 23, or 24 chain atoms (e.g., C, O, N, and S). In one embodiment, the Linker comprises 5, 6, 7, 8, 9, 10, 11, 12, 13, 14, 15, 16, 17, 18, 19, 20, 21, 22, 23, or 24 chain atoms (e.g., C, O, N, and S). In one embodiment, the Linker comprises 5, 7, 9, 11, 13, 15, 17, or 19 chain atoms (e.g., C, O, N, and S). In one embodiment, the Linker comprises 5, 7, 9, or 11 chain atoms (e.g., C, O, N, and S). In one embodiment, the Linker comprises 11, 13, 15, 17, or 19 chain atoms (e.g., C, O, N, and S). In one embodiment, the Linker comprises 11, 13, 15, 17, 19, 21, or 23 chain atoms (e.g., C, O, N, and S). In one embodiment, the Linker comprises 6, 8, 10, 12, 14, 16, 18, 20, 22, or 24 chain atoms (e.g., C, O, N, and S). In one embodiment, the Linker comprises 6, 8, 10, 12, 14, 16, 18, or 20 chain atoms (e.g., C, O, N, and S). In one embodiment, the Linker comprises 6, 8, 10, or 12 chain atoms (e.g., C, O, N, and S). In one embodiment, the Linker comprises 12, 14, 16, 18, or 20 chain atoms (e.g., C, O, N, and S).

In one embodiment, the Linker comprises from 11 to 19 chain atoms (e.g., C, O, N, and S).

In one embodiment, the Linker is a carbon chain optionally substituted with non-bulky substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl$)_2$, and CN). In one embodiment, the non-bulky substitution is located on the chain carbon atom proximal to the Degron (i.e., the carbon atom is separated from the carbon atom to which the Degron is bonded by at least 3, 4, or 5 chain atoms in the Linker). In one embodiment, the non-bulky substitution is located on the chain carbon atom proximal to the Targeting Ligand (i.e., the carbon atom is separated from the carbon atom to which the Degron is bonded by at least 3, 4, or 5 chain atoms in the Linker).

In one embodiment, the Linker is of Formula L0:

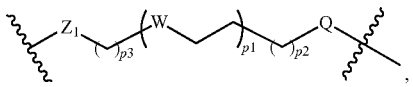

(L0)

or an enantiomer, diastereomer, or stereoisomer thereof, wherein
p1 is an integer selected from 0 to 12;
p2 is an integer selected from 0 to 12;
p3 is an integer selected from 1 to 6;
each W is independently absent, $CH_2$, O, S, NH, or $NR_{19}$;
$Z_1$ is absent, C(O), $(CH_2)_jC(O)NH$, $CH_2$, O, NH, or $NR_{19}$;
each $R_{19}$ is independently $C_1$-$C_3$ alkyl;
j is 1, 2, or 3; and
Q is absent or $NHC(O)CH_2$,
wherein the Linker is covalently bonded to a Degron via

the next to Q, and covalently bonded to a Targeting Ligand via the

In one embodiment, the total number of chain atoms in the Linker is less than 30. In a further embodiment, the total number of chain atoms in the Linker is less than 20.

For a Linker of Formula L0:
In one embodiment, p1 is an integer selected from 0 to 10.
In one embodiment, p1 is an integer selected from 1 to 10.
In one embodiment, p1 is selected from 1, 2, 3, 4, 5, and 6.
In one embodiment, p1 is 0, 1, 3, or 5.
In one embodiment, p1 is 0, 1, 2, or 3.
In one embodiment, p1 is 0.
In one embodiment, p1 is 1.
In one embodiment, p1 is 3.
In one embodiment, p1 is 5.
In one embodiment, p2 is an integer selected from 0 to 10.
In one embodiment, p2 is selected from 0, 1, 2, 3, 4, 5, and 6.
In one embodiment, p2 is 0, 1, 2, or 3.
In one embodiment, p2 is 0.
In one embodiment, p2 is 1.
In one embodiment, p3 is an integer selected from 1 to 5.
In one embodiment, p3 is 2, 3, 4, or 5.
In one embodiment, p3 is 0, 1, 2, or 3.
In one embodiment, p3 is 0.
In one embodiment, p3 is 1.
In one embodiment, p3 is 2.
In one embodiment, at least one W is $CH_2$.
In one embodiment, at least one W is O.
In one embodiment, at least one W is S.
In one embodiment, at least one W is NH.
In one embodiment, at least one W is $NR_{19}$; and each $R_{19}$ is independently $C_1$-$C_3$ alkyl selected from methyl, ethyl, and propyl.
In one embodiment, each W is O.
In one embodiment, j is 1, 2, or 3.
In one embodiment, j is 1.
In one embodiment, j is 2.
In one embodiment, j is 3.
In one embodiment, j is 2 or 3.
In one embodiment, j is 1 or 2.
In one embodiment, Q is absent.
In one embodiment, Q is $NHC(O)CH_2$.
In one embodiment, $Z_1$ is absent.
In one embodiment, $Z_1$ is $CH_2$.
In one embodiment, $Z_1$ is O.
In one embodiment, $Z_1$ is C(O).
In one embodiment, $Z_1$ is $(CH_2)_jC(O)NH$.
In one embodiment, $Z_1$ is $NR_{19}$; and $R_{19}$ is $C_1$-$C_3$ alkyl selected from methyl, ethyl, and propyl.
In one embodiment, $Z_1$ is part of the Targeting Ligand that is bonded to the Linker, namely, $Z_1$ is formed from reacting a functional group of the Targeting Ligand with the Linker.
In one embodiment, p1 is 1, 2, 3, or 4. In one embodiment, p1 is 1. In one embodiment, p1 is 2. In one embodiment, p1 is 3. In one embodiment, p1 is 4.
In one embodiment, p1 is 1 and $Z_1$ is absent.
In one embodiment, p1 is 1, $Z_1$ is absent, and W is $CH_2$.
In one embodiment, p1 is 1, $Z_1$ is absent, and p3 is 1.
In one embodiment, p1 is 1, $Z_1$ is absent, and p3 is 2.
In one embodiment, p1 is 1, $Z_1$ is absent, and p2 is 0.
In one embodiment, p1 is 1, $Z_1$ is absent, p3 is 2, and p2 is 0.
In one embodiment, p1 is 1, $Z_1$ is absent, p3 is 2, p2 is 0, and each W is O.
In one embodiment, p1 is 1, $Z_1$ is absent, p3 is 2, p2 is 0, each W is O, and Q is absent.
In one embodiment, p1 is 3 and $Z_1$ is absent.
In one embodiment, p1 is 3, $Z_1$ is absent, and p3 is 2.
In one embodiment, p1 is 3, $Z_1$ is absent, and p2 is 0.
In one embodiment, p1 is 3, $Z_1$ is absent, p3 is 2, and p2 is 0.
In one embodiment, p1 is 3, $Z_1$ is absent, p3 is 2, p2 is 0, and each W is O.
In one embodiment, p1 is 3, $Z_1$ is absent, p3 is 2, p2 is 0, each W is O, and Q is absent.
In one embodiment, p1 is 5 and $Z_1$ is absent.
In one embodiment, p1 is 5, $Z_1$ is absent, and p3 is 2.
In one embodiment, p1 is 5, $Z_1$ is absent, and p2 is 0.
In one embodiment, p1 is 5, $Z_1$ is absent, p3 is 2, and p2 is 0.
In one embodiment, p1 is 5, $Z_1$ is absent, p3 is 2, p2 is 0, and each W is O.
In one embodiment, p1 is 5, $Z_1$ is absent, p3 is 2, p2 is 0, each W is O, and Q is absent.
In one embodiment, p1 is 1 and $Z_1$ is C(O).
In one embodiment, p1 is 1, $Z_1$ is C(O), and p3 is 2.
In one embodiment, p1 is 1, $Z_1$ is C(O), and p2 is 0.
In one embodiment, p1 is 1, $Z_1$ is C(O), p3 is 2, and p2 is 0.
In one embodiment, p1 is 1, $Z_1$ is C(O), p3 is 2, p2 is 0, and each W is O.
In one embodiment, p1 is 1, $Z_1$ is C(O), p3 is 2, p2 is 0, each W is O, and Q is absent.
In one embodiment, p1 is 3 and $Z_1$ is C(O).
In one embodiment, p1 is 3, $Z_1$ is C(O), and p3 is 2.
In one embodiment, p1 is 3, $Z_1$ is C(O), and p2 is 0.

In one embodiment, p1 is 3, $Z_1$ is C(O), p3 is 2, and p2 is 0.

In one embodiment, p1 is 3, $Z_1$ is C(O), p3 is 2, p2 is 0, and each W is O.

In one embodiment, p1 is 3, $Z_1$ is C(O), p3 is 2, p2 is 0, each W is O, and Q is absent.

In one embodiment, p1 is 5 and $Z_1$ is C(O).

In one embodiment, p1 is 5, $Z_1$ is C(O), and p3 is 2.

In one embodiment, p1 is 5, $Z_1$ is C(O), and p2 is 0.

In one embodiment, p1 is 5, $Z_1$ is C(O), p3 is 2, and p2 is 0.

In one embodiment, p1 is 5, $Z_1$ is C(O), p3 is 2, p2 is 0, and each W is O.

In one embodiment, p1 is 5, $Z_1$ is C(O), p3 is 2, p2 is 0, each W is O, and Q is absent.

In one embodiment, p3 is 3 and $Z_1$ is absent.

In one embodiment, p3 is 3, $Z_1$ is absent, and p1 is 0.

In one embodiment, p3 is 3, $Z_1$ is absent, p1 is 0, and Q is absent.

In one embodiment, p3 is 4 and $Z_1$ is absent.

In one embodiment, p3 is 4, $Z_1$ is absent, and p1 is 0.

In one embodiment, p3 is 4, $Z_1$ is absent, p1 is 0, and Q is absent.

In one embodiment, p3 is 2, and $Z_1$ is absent.

In one embodiment, p1 is 3 and $Z_1$ is $(CH_2)_jC(O)NH$.

In one embodiment, p1 is 3 and $Z_1$ is $(CH_2)C(O)NH$.

In one embodiment, p1 is 3 and $Z_1$ is $(CH_2)_2C(O)NH$.

In one embodiment, p1 is 3 and $Z_1$ is $(CH_2)_3C(O)NH$.

In one embodiment, p1 is 3, $Z_1$ is $(CH_2)_jC(O)NH$, and p3 is 2.

In one embodiment, p1 is 3, $Z_1$ is $(CH_2)C(O)NH$, and p3 is 2.

In one embodiment, p1 is 3, $Z_1$ is $(CH_2)_2C(O)NH$, and p3 is 2.

In one embodiment, p1 is 3, $Z_1$ is $(CH_2)_3C(O)NH$, and p3 is 2.

In one embodiment, p1 is 3, $Z_1$ is $(CH_2)_jC(O)NH$, p3 is 2, and p2 is 0.

In one embodiment, p1 is 3, $Z_1$ is $(CH_2)C(O)NH$, p3 is 2, and p2 is 0.

In one embodiment, p1 is 3, $Z_1$ is $(CH_2)_2C(O)NH$, p3 is 2, and p2 is 0.

In one embodiment, p1 is 3, $Z_1$ is $(CH_2)_3C(O)NH$, p3 is 2, and p2 is 0.

In one embodiment, p1 is 3, $Z_1$ is $(CH_2)_jC(O)NH$, p3 is 2, p2 is 0, and each W is O.

In one embodiment, p1 is 3, $Z_1$ is $(CH_2)C(O)NH$, p3 is 2, p2 is 0, and each W is O.

In one embodiment, p1 is 3, $Z_1$ is $(CH_2)_2C(O)NH$, p3 is 2, p2 is 0, and each W is O.

In one embodiment, p1 is 3, $Z_1$ is $(CH_2)_3C(O)NH$, p3 is 2, p2 is 0, and each W is O.

In one embodiment, p1 is 3, $Z_1$ is $(CH_2)_jC(O)NH$, p3 is 2, p2 is 0, each W is O, and Q is absent.

In one embodiment, p1 is 3, $Z_1$ is $(CH_2)C(O)NH$, p3 is 2, p2 is 0, each W is O, and Q is absent.

In one embodiment, p1 is 3, $Z_1$ is $(CH_2)_2C(O)NH$, p3 is 2, p2 is 0, each W is O, and Q is absent.

In one embodiment, p1 is 3, $Z_1$ is $(CH_2)_3C(O)NH$, p3 is 2, p2 is 0, each W is O, and Q is absent.

In one embodiment, p1 is 3 and $Z_1$ is $CH_2C(O)NH$.

In one embodiment, p1 is 3, $Z_1$ is $CH_2C(O)NH$, and Q is absent.

In one embodiment, p1 is 4 and $Z_1$ is absent.

In one embodiment, p1 is 4, $Z_1$ is absent, and p2 is 1.

In one embodiment, p1 is 4, $Z_1$ is absent, p2 is 1, and Q is absent.

In one embodiment, p1 is 4, $Z_1$ is absent, p2 is 1, and p3 is 3.

In one embodiment, p1 is 4, $Z_1$ is absent, p2 is 1, p3 is 3, and Q is absent.

In one embodiment, p1 is 3 and $Z_1$ is absent.

In one embodiment, p1 is 3, $Z_1$ is absent, and p3 is 3.

In one embodiment, p1 is 3, Q is absent, and p3 is 3.

In one embodiment, p1 is 4, $Z_1$ is absent, and p3 is 3.

In one embodiment, p1 is 4, $Z_1$ is absent, p3 is 3, and Q is absent.

In one embodiment, p1 is 4, $Z_1$ is absent, p3 is 3, Q is absent, and p2 is 0.

In one embodiment, p1 is 4, $Z_1$ is absent, and Q is absent.

In one embodiment, p1 is 3, $Z_1$ is $CH_2C(O)NH$, and Q is absent.

In one embodiment, p1 is 3, $Z_1$ is $CH_2C(O)NH$, Q is absent, and p3 is 2.

In one embodiment, p1 is 4, Q is absent, and p3 is 1.

In one embodiment, p1 is 4, Q is absent, p3 is 1, and p2 is 0.

In one embodiment, p1 is 4, Q is absent, and p3 is 3.

In one embodiment, p1 is 4, Q is absent, p3 is 3, and p2 is 0.

In one embodiment, the Linker-Targeting Ligand (TL) has the structure selected from Table L:

TABLE L

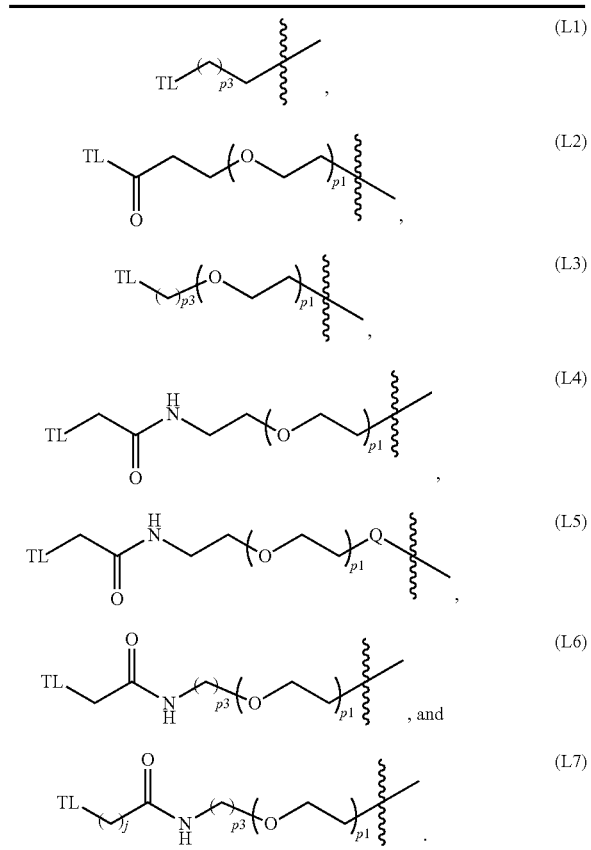

wherein Q, TL, p1, p3, and j are each as described above.

Any one of the Degrons described herein can be covalently bound to any one of the Linkers described herein. Any one of the Targeting Ligands described herein can be covalently bound to any one of the Linkers described herein.

In one embodiment, the present application relates to the Degron-Linker (DL), wherein the Degron is of Formula D1, and the Linker is selected from L1-L7. In one embodiment, the Degron is of Formula D1a or D1b, and the Linker is selected from L1-L7. In one embodiment, the Degron is of Formula D1a or D1b, and the Linker is L1, L2, or L3. In one embodiment, the Degron is of Formula D1a or D1b, and the Linker is L4, L5, L6, or L7. In one embodiment, the Degron is of Formula D1b, and the Linker is L1, L2, or L3. In one embodiment, the Degron is of Formula D1b, and the Linker is L4, L5, L6, or L7.

In one embodiment, the present application relates to the Degron-Linker (DL), wherein the Degron is of Formula D2, and the Linker is selected from L1-L7. In one embodiment, the Degron is of Formula D2a or D2b, and the Linker is selected from L1-L7. In one embodiment, the Degron is of Formula D2a or D2b, and the Linker is L1, L2, or L3. In one embodiment, the Degron is of Formula D2a or D2b, and the Linker is L4, L5, L6, or L7.

In one embodiment, the Linker is designed and optimized based on SAR (structure-activity relationship) and X-ray crystallography of the Targeting Ligand with regard to the location of attachment for the Linker.

In one embodiment, the optimal Linker length and composition vary by the Targeting Ligand and can be estimated based upon X-ray structure of the Targeting Ligand bound to its target. Linker length and composition can be also modified to modulate metabolic stability and pharmacokinetic (PK) and pharmacodynamics (PD) parameters.

Some embodiments of present application relate to the bifunctional compounds having the following structures in Table A:

TABLE A

| Cmpd No. | Structure |
|---|---|
| I-1 | 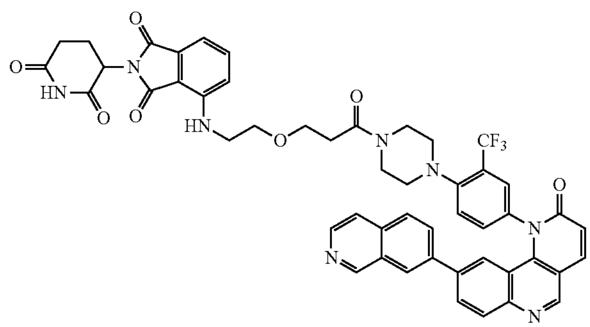 [SMILES: O=C1CCC(N2C(=O)c3cccc(NCCOCCC(=O)N4CCN(c5ccc(-n6c(=O)ccc7cnc8ccc(-c9ccc%10ccncc%10c9)cc8c76)cc5C(F)(F)F)CC4)c3C2=O)C(=O)N1] |
| I-2 | 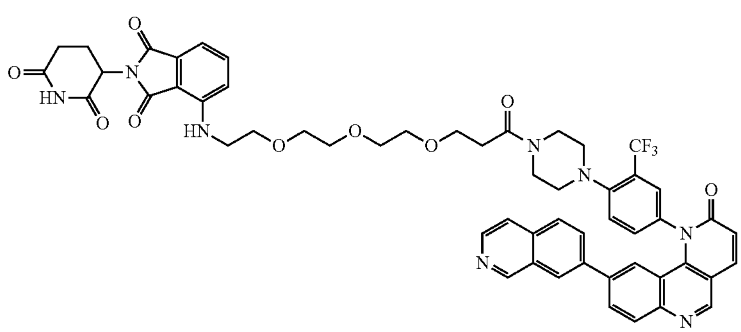 [SMILES: O=C1CCC(N2C(=O)c3cccc(NCCOCCOCCOCCC(=O)N4CCN(c5ccc(-n6c(=O)ccc7cnc8ccc(-c9ccc%10ccncc%10c9)cc8c76)cc5C(F)(F)F)CC4)c3C2=O)C(=O)N1] |
| I-3 | 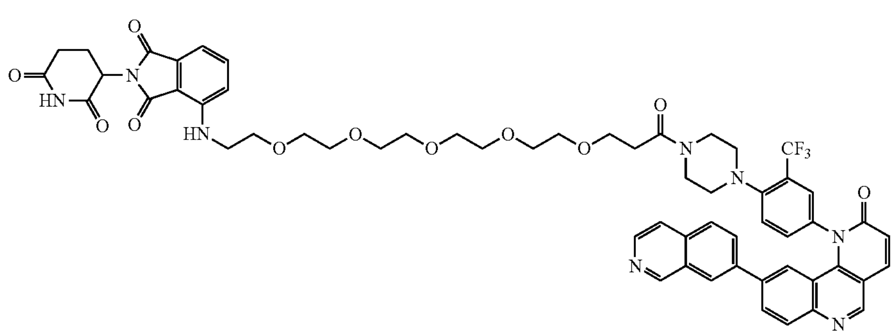 [SMILES: O=C1CCC(N2C(=O)c3cccc(NCCOCCOCCOCCOCCOCCC(=O)N4CCN(c5ccc(-n6c(=O)ccc7cnc8ccc(-c9ccc%10ccncc%10c9)cc8c76)cc5C(F)(F)F)CC4)c3C2=O)C(=O)N1] |

TABLE A-continued

| Cmpd No. | Structure |
|---|---|
| I-4 | 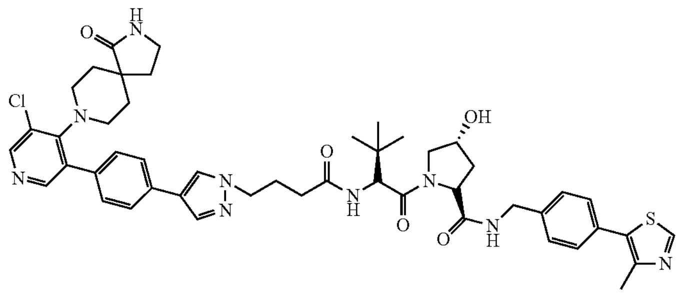 |
| I-5 | 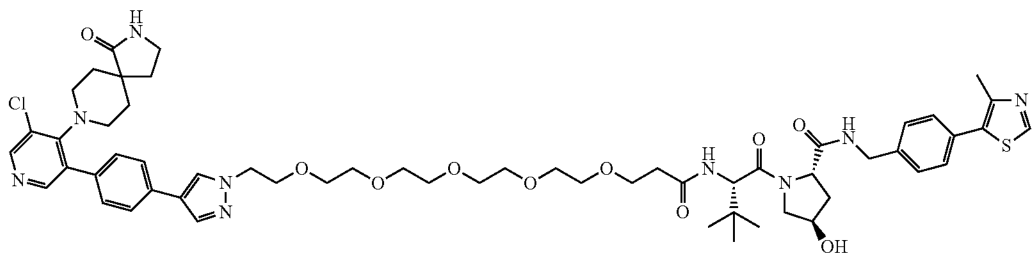 [SMILES: Cc1ncsc1-c1ccc(CNC(=O)[C@@H]2C[C@@H](O)CN2C(=O)[C@@H](NC(=O)CCOCCOCCOCCOCCOCCn2cc(-c3ccc(-c4cncc(Cl)c4N4CCC5(CCNC5=O)CC4)cc3)cn2)C(C)(C)C)cc1] |
| I-6 | 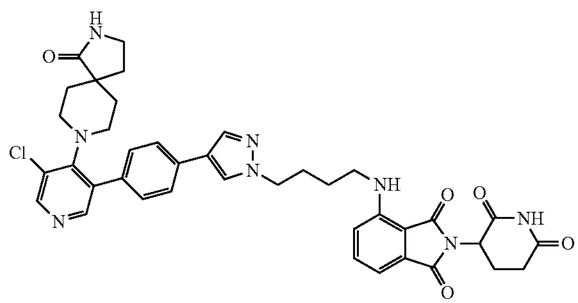 [SMILES: O=C1CCC(N2C(=O)c3cccc(NCCCCn4cc(-c5ccc(-c6cncc(Cl)c6N6CCC7(CCNC7=O)CC6)cc5)cn4)c3C2=O)C(=O)N1] |
| I-7 | 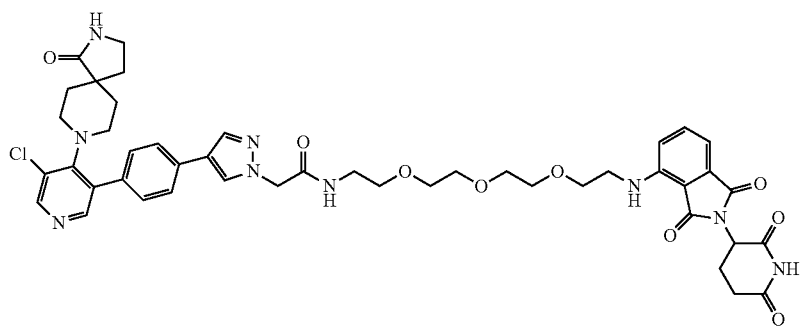 [SMILES: O=C(Cn1cc(-c2ccc(-c3cncc(Cl)c3N3CCC4(CCNC4=O)CC3)cc2)cn1)NCCOCCOCCOCCNc1cccc2c1C(=O)N(C1CCC(=O)NC1=O)C2=O] |
| I-8 | 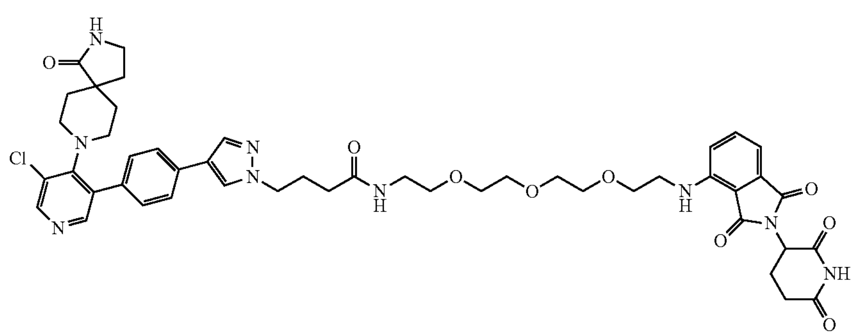 [SMILES: O=C(CCCn1cc(-c2ccc(-c3cncc(Cl)c3N3CCC4(CCNC4=O)CC3)cc2)cn1)NCCOCCOCCOCCNc1cccc2c1C(=O)N(C1CCC(=O)NC1=O)C2=O] |

TABLE A-continued

| Cmpd No. | Structure |
|---|---|
| I-9 | 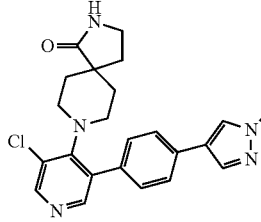 |

Some of the foregoing compounds can comprise one or more asymmetric centers, and thus can exist in various isomeric forms, e.g., stereoisomers and/or diastereomers. Accordingly, compounds of the application may be in the form of an individual enantiomer, diastereomer or geometric isomer, or may be in the form of a mixture of stereoisomers. In one embodiment, the compounds of the application are enantiopure compounds. In another embodiment, mixtures of stereoisomers or diastereomers are provided.

Furthermore, certain compounds, as described herein, may have one or more double bonds that can exist as either the Z or E isomer, unless otherwise indicated. The application additionally encompasses the compounds as individual Z/E isomers substantially free of other E/Z isomers and alternatively, as mixtures of various isomers.

In one embodiment, the present application relates to compounds that target proteins, such as CDK8 for degradation, which have numerous advantages over inhibitors of protein function (e.g., kinase activity) and can a) overcome resistance in certain cases; b) prolong the kinetics of drug effect by destroying the protein, thus requiring resynthesis of the protein even after the compound has been metabolized; c) target all functions of a protein at once rather than a specific catalytic activity or binding event; d) expand the number of drug targets by including all proteins that a ligand can be developed for, rather than proteins whose activity (e.g., kinase activity) can be affected by a small molecule inhibitor, antagonist or agonist; and e) have increased potency compared to inhibitors due to the possibility of the small molecule acting catalytically.

Some embodiments of the present application relate to degradation or loss of 30% to 100% of the target protein. Some embodiments relate to the loss of 50-100% of the target protein. Other embodiments relate to the loss of 75-95% of the targeted protein.

A bifunctional compound of the present application (e.g., a bifunctional compound of any of the formulae described herein, or selected from any bifunctional compounds described herein) is capable of modulating (e.g., decreasing) the amount of a targeted protein (e.g., CDK8). A bifunctional compound of the present application (e.g., a bifunctional compound of any of the formulae described herein, or selected from any bifunctional compounds described herein) is also capable of degrading a targeted protein (e.g., CDK8) through the UPP pathway. Accordingly, a bifunctional compound of the present application (e.g., a bifunctional compound of any of the formulae described herein, or selected from any bifunctional compounds described herein) is capable of treating or preventing a disease or disorder in which CDK8 plays a role. A bifunctional compound of the present application (e.g., a bifunctional compound of any of the formulae described herein, or selected from any bifunctional compounds described herein) is also capable of treating or preventing a disease or disorder in which CDK8 plays a role or in which CDK8 is deregulated (e.g., overexpressed).

Modulation of CDK8 through UPP-mediated degradation by a bifunctional compound of the application, such as those described herein, provides a novel approach to the treatment, prevention, or amelioration of diseases or disorders in which CDK8 plays a role including, but not limited to, cancer and metastasis, inflammation, arthritis, systemic lupus erythematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy. Further, modulation of CDK8 through UPP-mediated degradation by a bifunctional compound of the application, such as those described herein, also provides a new paradigm for treating, preventing, or ameliorating diseases or disorders in which CDK8 is deregulated.

In one embodiment, a bifunctional compound of the present application (e.g., a bifunctional compound of any of the formulae described herein, or selected from any bifunctional compounds described herein) is more efficacious in treating a disease or condition (e.g., cancer) than, or is capable of treating a disease or condition resistant to, the Targeting Ligand, when the Targeting Ligand is administered alone (i.e., not bonded to a Linker and a Degron). In one embodiment, a bifunctional compound of the present application (e.g., a bifunctional compound of any of the formulae described herein, or selected from any bifunctional compounds described herein) is capable of modulating (e.g., decreasing) the amount of CDK8, and thus is useful in treating a disease or condition (e.g., cancer) in which CDK8 plays a role.

In one embodiment, the bifunctional compound of the present application that is more efficacious in treating a disease or condition than, or is capable of treating a disease or condition resistant to, the Targeting Ligand, when the Targeting Ligand is administered alone (i.e., not bonded to a Linker and a Degron), is more potent in inhibiting the growth of cells (e.g., cancer cells) or decreasing the viability of cells (e.g., cancer cells), than the Targeting Ligand, when the Targeting Ligand is administered alone (i.e., not bonded to a Linker and a Degron). In one embodiment, the bifunctional compound inhibits the growth of cells (e.g., cancer cells) or decreases the viability of cells (e.g., cancer cells) at an $IC_{50}$ that is lower than the $IC_{50}$ of the Targeting Ligand (when the Targeting Ligand is administered alone (i.e., not bonded to a Linker and a Degron)) for inhibiting the growth or decreasing the viability of the cells. In one embodiment, the $IC_{50}$ of the bifunctional compound is at most 90%, 80%, 70%, 60%, 50%, 40%, 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 50%, 40%, 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 1%, 0.8%, 0.5%, 0.4%, 0.3%, 0.2%, or 0.1% of the $IC_{50}$ of the Targeting Ligand. In one embodiment, the bifunctional compound inhibits the growth of cells (e.g., cancer cells) or decreases the viability of cells (e.g., cancer cells) at an $E_{max}$ that is lower than the $E_{max}$ of the Targeting Ligand (when the Targeting Ligand is administered alone (i.e., not bonded to a Linker and a Degron)) for inhibiting the growth or decreasing the viability of the cells. In one embodiment, the $E_{max}$ of the bifunctional compound is at most 90%, 80%, 70%, 60%, 50%, 40%, 30%, 20%, 10%, 8%, 5%, 4%, 3%, 2%, or 1% of the $E_{max}$ of the Targeting Ligand. In one embodiment, the $E_{max}$ of the bifunctional compound is at most 50%, 40%, 30%, 20%, 10%, 8%, 5%, 4%, 3%, 2%, or 1% of the $E_{max}$ of the Targeting Ligand. In one embodiment, the $E_{max}$ of the bifunctional compound is at most 90%, 80%, 70%, 60%, 50%, 40%, 30%, 20%, or 10% of the $E_{max}$ of the Targeting Ligand.

In some embodiments, the inhibition of CDK8 activity is measured by $IC_{50}$.

In some embodiments, the inhibition of CDK8 activity is measured by $EC_{50}$.

Potency of the inhibitor can be determined by $EC_{50}$ value. A compound with a lower $EC_{50}$ value, as determined under substantially similar conditions, is a more potent inhibitor relative to a compound with a higher $EC_{50}$ value. In some embodiments, the substantially similar conditions comprise determining a CDK8-dependent phosphorylation level, in vitro or in vivo (e.g., in cells expressing a wild-type CDK8, a mutant CDK8, or a fragment of any thereof).

Potency of the inhibitor can also be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining a CDK8-dependent phosphorylation level, in vitro or in vivo (e.g., in cells expressing a wild-type CDK8, a mutant CDK8, or a fragment of any thereof).

In one embodiment, the bifunctional compounds of the present application are useful as anticancer agents, and thus may be useful in the treatment of cancer, by effecting tumor cell death or inhibiting the growth of tumor cells. In certain exemplary embodiments, the disclosed anticancer agents are useful in the treatment of cancers and other proliferative disorders, including, but not limited to breast cancer, cervical cancer, colon and rectal cancer, leukemia, lung cancer (e.g., non-small cell lung cancer), melanoma, multiple myeloma, non-Hodgkin's lymphoma, ovarian cancer, pancreatic cancer, prostate cancer, gastric cancer, leukemias (e.g., myeloid, lymphocytic, myelocytic and lymphoblastic leukemias), malignant melanomas, and T-cell lymphoma.

A "selective CDK8 inhibitor," can be identified, for example, by comparing the ability of a compound to inhibit CDK8 kinase activity to its ability to inhibit the other members of the CDK kinase family or other kinases. For example, a substance may be assayed for its ability to inhibit CDK8 kinase activity, as well as CDK1, CDK2, CDK4, CDK6, CDK7, CDK9, CDK11, CDK12, CDK13, CDK14 and other kinases. In some embodiments, the selectivity can be identified by measuring the $EC_{50}$ or $IC_{50}$ of the compounds.

In some embodiments, the bifunctional compounds of the present application containing a Target Ligand inhibit CDK8 more selectively over other cyclin-dependent kinases and/or other kinases than the Target Ligand alone (i.e., a Target Ligand itself compared to the Target Ligand covalently bound to a Linker and a Degron). In certain embodiments, the bifunctional compounds of the application are about 10%, about 20%, about 30%, about 40%, about 50%, about 60%, about 70%, about 80%, about 90% or about 99% more selective at inhibiting CDK8 than the Target Ligand alone. In certain embodiments, the bifunctional compounds of the application are about 10%, about 20%, about 30%, about 40%, or about 50% more selective at inhibiting CDK8 than the Target Ligand alone. In certain embodiments, the bifunctional compounds of the application are about 20%, about 30%, about 40%, about 50% or about 60% more selective at inhibiting CDK8 than the Target Ligand alone. In certain embodiments, the bifunctional compounds of the application are about 30%, about 40%, about 50%, about 60% or about 70% more selective at inhibiting CDK8 than the Target Ligand alone. In certain embodiments, the bifunctional compounds of the application are about 40%, about 50%, about 60%, about 70%, or about 80% more selective at inhibiting CDK8 than the Target Ligand alone. In certain embodiments, the bifunctional compounds of the application are about 50%, about 60%, about 70%, about 80%, or about 90% more selective at inhibiting CDK8 than the Target Ligand alone. In certain embodiments, the bifunctional compounds of the application are about 60%, about 70%, about 80%, about 90%, or about 99% more selective at inhibiting CDK8 than the Target Ligand alone. In other embodiments, the bifunctional compounds of the application are at least 10%, at least 20%, at least 30%, at least 40%, at least 50%, at least 60%, at least 70%, at least 80%, at least 90%, or at least 99% more selective at inhibiting CDK8 than the Target Ligand alone.

In other embodiments, the bifunctional compounds of the application are between about 10% and about 99% more selective at inhibiting CDK8 than the Target Ligand alone. In other embodiments, the bifunctional compounds of the application are between about 10% and about 30% more selective at inhibiting CDK8 than the Target Ligand alone. In other embodiments, the bifunctional compounds of the application are between about 20% and about 40% more selective at inhibiting CDK8 than the Target Ligand alone. In other embodiments, the bifunctional compounds of the application are between about 30% and about 50% more selective at inhibiting CDK8 than the Target Ligand alone. In other embodiments, the bifunctional compounds of the application are between about 40% and about 60% more selective at inhibiting CDK8 than the Target Ligand alone. In other embodiments, the bifunctional compounds of the application are between about 50% and about 70% more selective at inhibiting CDK8 than the Target Ligand alone. In other embodiments, the bifunctional compounds of the application are between about 60% and about 80% more selective at inhibiting CDK8 than the Target Ligand alone. In other embodiments, the bifunctional compounds of the application are between about 70% and about 90% more selective at inhibiting CDK8 than the Target Ligand alone. In other embodiments, the bifunctional compounds of the application are between about 80% and about 99% more selective at inhibiting CDK8 than the Target Ligand alone.

In some embodiments, the compounds of the present application are selective over other kinases. As used herein, "selective", "selective CDK8 inhibitor", or "selective CDK8 compound" refers to a compound, for example a bifunctional compound of the application, that effectively inhibits CDK8 kinase to a greater extent than any other kinase enzyme, particularly any enzyme from the Cyclic-dependent kinase family (e.g., CDK1, CDK2, CDK4, CDK6, CDK7, CDK9, CDK11, CDK12, CDK13, CDK14, etc.).

In certain embodiments, the compounds of the application are CDK8 inhibitors that exhibit at least 2-fold, 3-fold, 5-fold, 10-fold, 25-fold, 50-fold or 100-fold selectivity over other kinases (e.g., CDK1, CDK2, CDK4, CDK6, CDK7, CDK9, CDK11, CDK12, CDK13, CDK14, etc.). In various embodiments, the compounds of the application exhibit 1000-fold selectivity over other kinases.

In certain embodiments, the compounds of the application are CDK8 inhibitors that exhibit at least 2-fold, 3-fold, 5-fold, 10-fold, 25-fold, 50-fold or 100-fold selectivity over other cyclin-dependent kinases (e.g., CDK1, CDK2, CDK4, CDK6, CDK7, CDK9, CDK11, CDK12, CDK13, CDK14, etc.). In various embodiments, the compounds of the application exhibit 1000-fold selectivity over other cyclin-dependent kinases.

Definitions

Listed below are definitions of various terms used in this application. These definitions apply to the terms as they are used throughout this specification and claims, unless otherwise limited in specific instances, either individually or as part of a larger group.

The term "alkyl," as used herein, refers to saturated, straight or branched-chain hydrocarbon radicals containing, in certain embodiments, between one and six carbon atoms. Examples of $C_1$-$C_6$ alkyl radicals include, but are not limited to, methyl, ethyl, propyl, isopropyl, n-butyl, tert-butyl, neopentyl, and n-hexyl radicals.

The term "alkenyl," as used herein, denotes a monovalent group derived from a hydrocarbon moiety containing, in certain embodiments, from two to six carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl and the like.

The term "alkoxy" refers to an —O-alkyl radical.

The terms "hal," "halo," and "halogen," as used herein, refer to an atom selected from fluorine, chlorine, bromine and iodine.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$ cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocyclyl," or "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl), e.g., —NH($C_1$-$C_6$ alkyl), where $C_1$-$C_{12}$ alkyl is as previously defined.

The term "dialkylamino" refers to a group having the structure —N($C_1$-$C_{12}$ alkyl)$_2$, e.g., —NH($C_1$-$C_6$ alkyl), where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the application, any of the aryls, substituted aryls, heteroaryls and substituted heteroaryls described herein, can be any aromatic group. Aromatic groups can be substituted or unsubstituted.

The terms "hal," "halo," and "halogen," as used herein, refer to an atom selected from fluorine, chlorine, bromine and iodine.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I, —OH, protected hydroxy, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)—heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH— heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)— heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$—heterocycloalkyl, NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, NHC(O)NH-heterocycloalkyl, —NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NHheterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, C(NH)NH—C$_3$-C$_{12}$-cycloalkyl, —C(NH)NH-aryl, —C(NH)NH-heteroaryl, —C(NH)NHheterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

It is understood that the aryls, heteroaryls, alkyls, and the like can be substituted. The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colonrectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "CDK8" herein refers to cyclin-dependent kinase 8.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, "preventing" or "prevent" describes reducing or eliminating the onset of the symptoms or complications of the disease, condition or disorder.

The term "targeted protein(s)" is used interchangeably with "target protein(s)", unless the context clearly dictates otherwise. In one embodiment, a "targeted protein" is CDK.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

The terms "disease(s)", "disorder(s)", and "condition(s)" are used interchangeably, unless the context clearly dictates otherwise.

The term "therapeutically effective amount" of a bifunctional compound or pharmaceutical composition of the application, as used herein, means a sufficient amount of the bifunctional compound or pharmaceutical composition so as to decrease the symptoms of a disorder in a subject. As is well understood in the medical arts a therapeutically effective amount of a bifunctional compound or pharmaceutical composition of this application will be at a reasonable benefit/risk ratio applicable to any medical treatment. It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). The salts can be prepared in situ during the final isolation and purification of the compounds of the application, or separately by reacting the free base or acid function with a suitable acid or base.

Examples of pharmaceutically acceptable salts include, but are not limited to, nontoxic acid addition salts: salts formed with inorganic acids such as hydrochloric acid, hydrobromic acid, phosphoric acid, sulfuric acid and perchloric acid, or with organic acids such as acetic acid, maleic acid, tartaric acid, citric acid, succinic acid or malonic acid. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, /7-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the bifunctional compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein, refers to those prodrugs of the bifunctional compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application. "Prodrug", as used herein, means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This application also encompasses pharmaceutical compositions containing, and methods of treating disorders through administering, pharmaceutically acceptable prodrugs of bifunctional compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews*, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

The application also provides for a pharmaceutical composition comprising a therapeutically effective amount of a bifunctional compound of the application, or an enantiomer, diastereomer, stereoisomer, or pharmaceutically acceptable salt thereof, and a pharmaceutically acceptable carrier.

In another aspect, the application provides a kit comprising a bifunctional compound capable of inhibiting CDK8 activity selected from one or more compounds disclosed herein, or a pharmaceutically acceptable salt, hydrate, solvate, prodrug, stereoisomer, or tautomer thereof, optionally in combination with a second agent and instructions for use in treating cancer.

In another aspect, the application provides a method of synthesizing a bifunctional compound disclosed herein.

The synthesis of the bifunctional compounds of the application can be found herein and in the Examples below.

Other embodiments are a method of making a bifunctional compound of any of the formulae herein using any one, or combination of, reactions delineated herein. The method can include the use of one or more intermediates or chemical reagents delineated herein.

Another aspect is an isotopically labeled bifunctional compound of any of the formulae delineated herein. Such compounds have one or more isotope atoms which may or may not be radioactive (e.g., $^3$H, $^2$H, $^{14}$C, $^{13}$C, $^{18}$F, $^{35}$S, $^{32}$P, $^{125}$I, and $^{131}$I) introduced into the bifunctional compound. Such compounds are useful for drug metabolism studies and diagnostics, as well as therapeutic applications.

A bifunctional compound of the application can be prepared as a pharmaceutically acceptable acid addition salt by reacting the free base form of the compound with a pharmaceutically acceptable inorganic or organic acid. Alternatively, a pharmaceutically acceptable base addition salt of a bifunctional compound of the application can be prepared by reacting the free acid form of the bifunctional compound with a pharmaceutically acceptable inorganic or organic base.

Alternatively, the salt forms of the bifunctional compounds of the application can be prepared using salts of the starting materials or intermediates.

The free acid or free base forms of the bifunctional compounds of the application can be prepared from the corresponding base addition salt or acid addition salt from, respectively. For example, a bifunctional compound of the application in an acid addition salt form can be converted to the corresponding free base by treating with a suitable base (e.g., ammonium hydroxide solution, sodium hydroxide, and the like). A bifunctional compound of the application in a base addition salt form can be converted to the corresponding free acid by treating with a suitable acid (e.g., hydrochloric acid, etc.).

Prodrugs of the bifunctional compounds of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized bifunctional compound of the application with a suitable carbamylating agent (e.g., 1,1-acyloxyalkylcarbanochloridate, para-nitrophenyl carbonate, or the like).

Protected derivatives of the bifunctional compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present application can be conveniently prepared, or formed during the process of the application, as solvates (e.g., hydrates). Hydrates of bifunctional compounds of the present application can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

When any variable (e.g., $R_{14}$) occurs more than one time in any constituent or formula for a compound, its definition at each occurrence is independent of its definition at every other occurrence. Thus, for example, if a group is shown to be substituted with one or more $R_{14}$ moieties, then $R_{14}$ at each occurrence is selected independently from the definition of $R_{14}$. Also, combinations of substituents and/or variables are permissible, but only if such combinations result in stable compounds within a designated atom's normal valency.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or F- or Z-double isomeric forms, and other stereoisomeric forms that may be defined, in terms of absolute stereochemistry, as (R)- or (S)-, or as (D)- or (L)- for amino acids. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present application.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981).

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products).

In the present application, the structural formula of the bifunctional compound represents a certain isomer for convenience in some cases, but the present application includes all isomers, such as geometrical isomers, optical isomers based on an asymmetrical carbon, stereoisomers, tautomers, and the like. In the present specification, the structural formula of the compound represents a certain isomer for convenience in some cases, but the present application includes all isomers, such as geometrical isomers, optical isomers based on an asymmetrical carbon, stereoisomers, tautomers, and the like.

Additionally, the compounds of the present application, for example, the salts of the bifunctional compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The synthesized bifunctional compounds can be separated from a reaction mixture and further purified by a method such as column chromatography, high pressure liquid chromatography, or recrystallization. As can be appreciated by the skilled artisan, further methods of synthesizing the bifunctional compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Method of Synthesizing the Compounds

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; and Greene, T. W., Wuts, P. G. M., *Protective Groups in Organic Synthesis*, $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application. The processes generally provide the desired final compound at or near the end of the overall process, although it may be desirable in certain instances to further convert the compound to a pharmaceutically acceptable salt, ester or prodrug thereof. Suitable synthetic routes are depicted in the schemes below.

Those skilled in the art will recognize if a stereocenter exists in the compounds disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below.

Compounds of the present application can be synthesized by following the steps outlined in General Scheme 1 and 2 which comprise different sequences of assembling intermediates. Starting materials are either commercially available or made by known procedures in the reported literature or as illustrated.

General Scheme 1 Synthesis of Thalidomide-based Degronimids

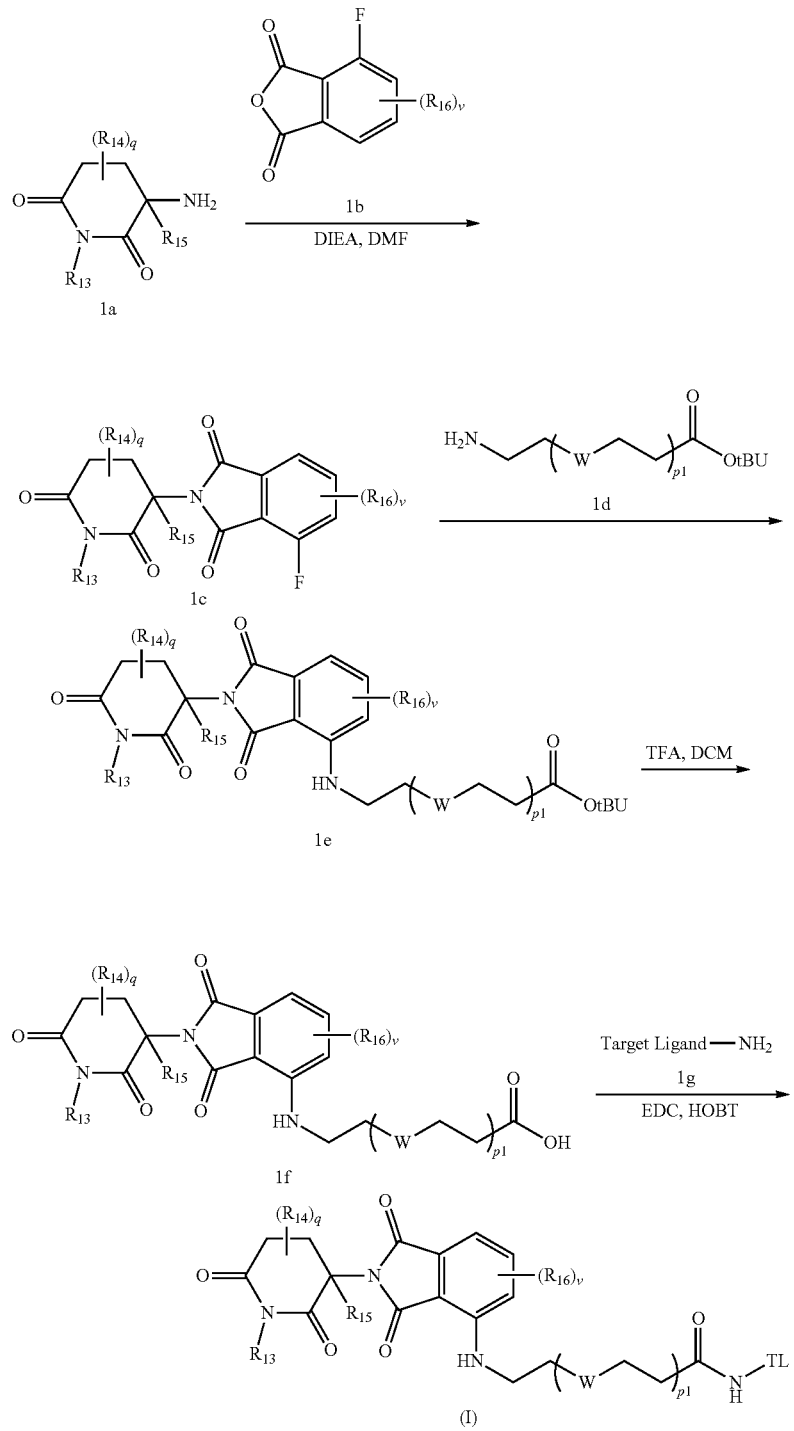

wherein $R_{13}$, $R_{14}$, $R_{15}$, $R_{16}$, W, p1, q, and v are as defined herein above.

The general way of preparing representative compounds of the present application (i.e., Compound of Formula (1) shown above) using intermediates 1a, 1b, 1c, 1d, 1e, 1f, and 1g is outlined in General Scheme 1. Reaction of 1a with 1b in the presence of a base, i.e., diisopropylethylamine (DIPEA), and in a solvent, i.e., dimethylformamide (DMF), provides intermediate 1c. Reaction of 1d with fluoride 1c provides intermediate 1e. Deprotection of the 1e in the presence of TFA in a solvent, i.e., dichloromethane (DCM) or methanol (MeOH), provides 1f. Coupling of 1f and Target Ligand 1g under standard coupling conditions using a coupling reagent, i.e., 1-ethyl-3-(3-dimethylaminopropyl) carbodiimide (EDC) and hydroxybenzotriazole, in a solvent, i.e., DCM or DMF, provides bifunctional compound of formula (I).

General Scheme 2 Synthesis of VHL-based Degronimids

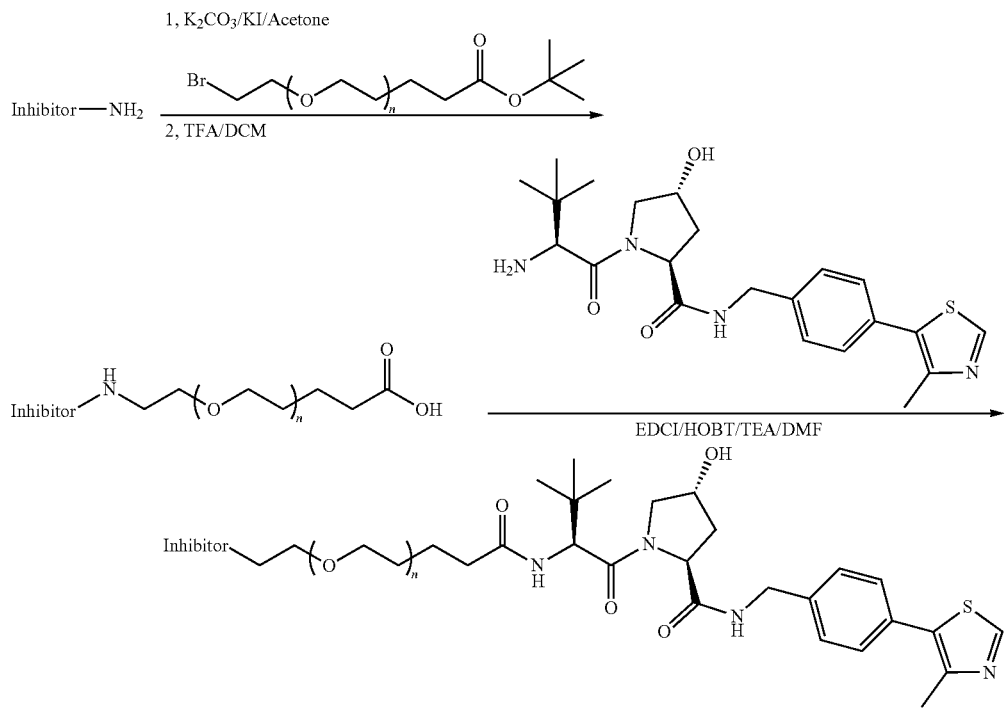

Biological Assays

Cell Viability Assay

Wild-type or cereblon null cells are treated with various concentrations of a bifunctional compound of the invention and allowed to grow. Cells are then assayed to determine cell viability by measuring the amount of ATP present, which is an indicator of cell metabolic activity. Results are graphed as relative luminescent values.

Enzyme Degradation Assay

Cells are treated with a control or a bifunctional compound of the application alone or in combination with an agent that blocks proteasomal degradation at a single concentration or various concentrations. After treatment, cells are washed and harvested by resuspending in buffer and lysed on ice 30 minutes. Lysates are then cleared by centrifugation. Samples are boiled and equal amount of protein is loaded onto polyacrylamide gel. The gel is transferred to nitrocellulose and blotted for CDK8, mTOR, STAT1 serine 727 phosphorylation or actin.

Western Blotting on CDK8

Cells are treated with a control or a bifunctional compound of the application at various concentrations for a desired period of time. Cells are then lysed in a suitable buffer. Protein concentration may be measured with any appropriate assay known in the art. Equivalent amounts of the samples are loaded on a polyacrylamide gel, transferred to nitrocellulose membranes, and immunoblotted with antibodies against CDK8 and a loading control, such as actin. Labeled secondary antibodies are added and washed. The signals from the label are detected.

Methods of the Application

In another aspect, the application provides a method of modulating a kinase, comprising contacting the kinase with a bifunctional compound disclosed herein, or a pharmaceutically acceptable salt, hydrate, solvate, prodrug, stereoisomer, or tautomer thereof, or with a pharmaceutical composition disclosed herein. In some embodiments, the kinase is CDK8.

In another aspect, the application provides a method of inhibiting a kinase, comprising contacting the kinase with a bifunctional compound disclosed herein, or a pharmaceutically acceptable salt, hydrate, solvate, prodrug, stereoisomer, or tautomer thereof, or with a pharmaceutical composition disclosed herein. In some embodiments, the kinase is CDK8.

In still another aspect, the application provides a method of inhibiting cyclin-dependent kinase (CDK8), the method comprising administering to a subject in need thereof an effective amount of a bifunctional compound disclosed herein, or a pharmaceutically acceptable salt, hydrate, solvate, prodrug, stereoisomer, or tautomer thereof.

In still another aspect, the application provides a method of inhibiting cyclin-dependent kinase (CDK8), the method comprising administering to a subject in need thereof an effective amount of a pharmaceutical composition comprising a bifunctional compound disclosed herein, or a pharmaceutically acceptable salt, hydrate, solvate, prodrug, stereoisomer, or tautomer thereof and a pharmaceutically acceptable carrier.

Another aspect of the application provides a method of treating or preventing a disease, the method comprising administering to a subject in need thereof an effective amount of a bifunctional compound disclosed herein, or a pharmaceutically acceptable salt, hydrate, solvate, prodrug, stereoisomer, or tautomer thereof. In some embodiments, the disease is mediated by a kinase. In further embodiments, the kinase is CDK8.

Another aspect of the application provides a method of treating or preventing a disease, the method comprising administering to a subject in need thereof an effective amount of a pharmaceutical composition comprising a bifunctional compound disclosed herein, or a pharmaceutically acceptable salt, hydrate, solvate, prodrug, stereoisomer, or tautomer thereof and a pharmaceutically acceptable carrier. In some embodiments, the disease is mediated by a kinase. In further embodiments, the kinase is CDK8.

In some embodiments, the disease is mediated by CDK8 (e.g., CDK8 plays a role in the initiation or development of the disease).

In certain embodiments, the disease or disorder is cancer or a proliferation disease.

In further embodiments, the disease or disorder is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In other embodiments, the disease or disorder is inflammation, arthritis, rheumatoid arthritis, spondyiarthropathies, gouty arthritis, osteoarthritis, juvenile arthritis, and other arthritic conditions, systemic lupus erythematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy, or B-Cell Lymphoma.

In further embodiments, the disease or disorder is inflammation, arthritis, rheumatoid arthritis, spondyloarthropathies, gouty arthritis, osteoarthritis, juvenile arthritis, and other arthritic conditions, systemic lupus erythematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia or lymphoma.

Another aspect of the application provides a method of treating a kinase mediated disorder, the method comprising administering to a subject in need thereof an effective amount of a bifunctional compound disclosed herein, or a pharmaceutically acceptable salt, hydrate, solvate, prodrug, stereoisomer, or tautomer thereof. In some embodiments, the bifunctional compound is an inhibitor of CDK8. In other embodiments, the subject is administered an additional therapeutic agent. In other embodiments, the bifunctional compound and the additional therapeutic agent are administered simultaneously or sequentially.

Another aspect of the application provides a method of treating a kinase mediated disorder, the method comprising administering to a subject in need thereof an effective amount of a pharmaceutical composition comprising a bifunctional compound disclosed herein, or a pharmaceutically acceptable salt, hydrate, solvate, prodrug, stereoisomer, or tautomer thereof and a pharmaceutically acceptable carrier. In some embodiments, the bifunctional compound is an inhibitor of CDK8. In other embodiments, the subject is administered an additional therapeutic agent. In other embodiments, the pharmaceutical composition comprising a bifunctional compound and the additional therapeutic agent are administered simultaneously or sequentially.

In other embodiments, the disease or disorder is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

Another aspect of the present application relates to a method of treating or preventing a proliferative disease. The method comprises administering to a subject in need thereof an effective amount of a bifunctional compound of the application, or a pharmaceutically acceptable salt, hydrate, solvate, prodrug, stereoisomer, or tautomer thereof.

Another aspect of the present application relates to a method of treating or preventing a proliferative disease. The method comprises administering to a subject in need thereof an effective amount of a pharmaceutical composition comprising a bifunctional compound disclosed herein, or a pharmaceutically acceptable salt, hydrate, solvate, prodrug, stereoisomer, or tautomer thereof and a pharmaceutically acceptable carrier.

In another aspect, the application provides a method of treating or preventing cancer, wherein the cancer cell comprises activated CDK8, comprising administering to a subject in need thereof an effective amount of a bifunctional compound disclosed herein, or a pharmaceutically acceptable salt, hydrate, solvate, prodrug, stereoisomer, or tautomer thereof.

In another aspect, the application provides a method of treating or preventing cancer, wherein the cancer cell comprises activated CDK8, comprising administering to a subject in need thereof an effective amount of a pharmaceutical composition comprising a bifunctional compound disclosed herein, or a pharmaceutically acceptable salt, hydrate, solvate, prodrug, stereoisomer, or tautomer thereof and a pharmaceutically acceptable carrier.

In certain embodiments, the CDK8 activation is selected from mutation of CDK8, amplification of CDK8, expression of CDK8, and ligand mediated activation of CDK8.

Another aspect of the application provides a method of treating or preventing cancer in a subject, wherein the subject is identified as being in need of CDK8 inhibition for the treatment of cancer, comprising administering to the subject an effective amount of a bifunctional compound disclosed herein, or a pharmaceutically acceptable salt, hydrate, solvate, prodrug, stereoisomer, or tautomer thereof.

Another aspect of the application provides a method of treating or preventing cancer in a subject, wherein the subject is identified as being in need of CDK8 inhibition for the treatment of cancer, comprising administering to the subject an effective amount of a pharmaceutical composition comprising a bifunctional compound disclosed herein, or a pharmaceutically acceptable salt, hydrate, solvate, prodrug, stereoisomer, or tautomer thereof and a pharmaceutically acceptable carrier.

In certain embodiments, the application provides a method of treating any of the disorders described herein, wherein the subject is a human. In certain embodiments, the application provides a method of preventing any of the disorders described herein, wherein the subject is a human.

In another aspect, the application provides a bifunctional compound disclosed herein, or a pharmaceutically acceptable salt, hydrate, solvate, prodrug, stereoisomer, or tautomer thereof, for use in the manufacture of a medicament for treating or preventing a disease in which CDK8 plays a role.

In still another aspect, the application provides a bifunctional compound of the application, or a pharmaceutically acceptable salt, hydrate, solvate, prodrug, stereoisomer, or tautomer thereof for use in treating or preventing a disease in which CDK8 plays a role.

In another aspect, the application provides a pharmaceutical composition comprising a bifunctional compound disclosed herein, or a pharmaceutically acceptable salt, hydrate, solvate, prodrug, stereoisomer, or tautomer thereof and a pharmaceutically acceptable carrier, for use in the manufacture of a medicament for treating or preventing a disease in which CDK8 plays a role.

In still another aspect, the application provides a pharmaceutical composition comprising a bifunctional compound disclosed herein, or a pharmaceutically acceptable salt, hydrate, solvate, prodrug, stereoisomer, or tautomer thereof and a pharmaceutically acceptable carrier, for use in treating or preventing a disease in which CDK8 plays a role.

As inhibitors of CDK8 kinase, the bifunctional compounds and compositions of this application are particularly useful for treating or lessening the severity of a disease, condition, or disorder where a protein kinase is implicated in the disease, condition, or disorder. In one aspect, the present application provides a method for treating or lessening the severity of a disease, condition, or disorder where a protein kinase is implicated in the disease state. In another aspect, the present application provides a method for treating or lessening the severity of a kinase disease, condition, or disorder where inhibition of enzymatic activity is implicated in the treatment of the disease. In another aspect, this application provides a method for treating or lessening the severity of a disease, condition, or disorder with bifunctional compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this application provides bifunctional compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject bifunctional compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the bifunctional compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more bifunctional compounds of the application in the manufacture of a medicament for the treatment of cancer, including without limitation the various types of cancer disclosed herein.

In some embodiments, the bifunctional compounds of this application are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the bifunctional compounds of this application are useful for treating hematopoietic disorders, in particular, acute-myelogenous leukemia (AML), chronic-myelogenous leukemia (CML), acute-promyelocytic leukemia, and acute lymphocytic leukemia (ALL).

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject bifunctional compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

Examples of neurodegenerative diseases include, without limitation, Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and Toxic encephalopathy.

Another aspect of this application provides a method for the treatment or lessening the severity of a disease selected from a proliferative or hyperproliferative disease, or a neurodegenerative disease, comprising administering an effective amount of a bifunctional compound, or a pharmaceutically acceptable composition comprising a bifunctional compound, to a subject in need thereof.

As inhibitors of CDK8 kinase, the compounds and compositions of this application are also useful in biological samples. One aspect of the application relates to inhibiting protein kinase activity in a biological sample, which method comprises contacting said biological sample with a bifunctional compound of the application or a composition comprising said bifunctional compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this application relates to the study of CDK8 kinase in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds and compositions of the present application as CDK8 inhibitors may be assayed in vitro, in vivo, or in a cell line. In vitro assays include assays that determine inhibition of either the kinase activity or ATPase activity of the activated kinase. Alternate in vitro assays quantitate the ability of the inhibitor to bind to the protein kinase and may be measured either by radio labelling the inhibitor prior to binding, isolating the inhibitor/kinase complex and determining the amount of radio label bound, or by running a competition experiment where new inhibitors are incubated with the kinase bound to known radioligands. Detailed conditions for assaying a compound utilized in this application as an inhibitor of various kinases are set forth in the Examples below.

In accordance with the foregoing, the present application further provides a method for preventing or treating any of the diseases or disorders described above in a subject in need of such treatment, which method comprises administering to said subject a therapeutically effective amount of a bifunctional compound of the application, or a pharmaceutically acceptable salt, hydrate, solvate, prodrug, stereoisomer, or tautomer thereof. For any of the above uses, the required dosage will vary depending on the mode of administration, the particular condition to be treated and the effect desired.

Pharmaceutical Compositions

In another aspect, the application provides a pharmaceutical composition comprising a therapeutically effective amount of a bifunctional compound of the present application or an enantiomer, diastereomer, stereoisomer, or pharmaceutically acceptable salt thereof, and a pharmaceutically acceptable carrier.

Bifunctional compounds of the application can be administered as pharmaceutical compositions by any conventional route, in particular enterally, e.g., orally, e.g., in the form of tablets or capsules, or parenterally, e.g., in the form of injectable solutions or suspensions, or topically, e.g., in the form of lotions, gels, ointments or creams, or in a nasal or suppository form. Pharmaceutical compositions comprising a compound of the present application in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxy propylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this application can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds and compositions of the application can be administered in therapeutically effective amounts in a combinational therapy with one or more therapeutic agents (pharmaceutical combinations) or modalities, e.g., an anti-proliferative, anti-cancer, immunomodulatory or anti-inflammatory agent. Where the compounds of the application are administered in conjunction with other therapies, dosages of the co-administered compounds will of course vary depending on the type of co-drug employed, on the specific drug employed, on the condition being treated and so forth. Compounds and compositions of the application can be administered in therapeutically effective amounts in a combinational therapy with one or more therapeutic agents (pharmaceutical combinations) or modalities, e.g., anti-proliferative, anti-cancer, immunomodulatory or anti-inflammatory agent, and/or non-drug therapies, etc. For example, synergistic effects can occur with anti-proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy includes the administration of the subject compounds in further combination with one or more other biologically active ingredients (such as, but not limited to, a second CDK8 inhibitor, a second and different antineoplastic agent, a second cyclin-dependent kinase inhibitor (i.e., CDK1, CDK2, CDK4, CDK6, CDK7, CDK9, CDK11, CDK12, CDK13, CDK14, etc.) and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

In another aspect of the application, the compounds may be administered in combination with one or more separate pharmaceutical agents, e.g., a chemotherapeutic agent, an immunotherapeutic agent, or an adjunctive therapeutic agent.

EXAMPLES

Analytical Methods, Materials, and Instrumentation

All reactions were monitored Waters Acquity UPLC/MS system (Waters PDA eλ Detector, QDa Detector, Sample manager—FL, Binary Solvent Manager) using Acquity UPLC® BEH C18 column (2.1×50 mm, 1.7 μm particle size): solvent gradient=90% A at 0 min, 1% A at 1.8 min; solvent A=0.1% formic acid in Water; solvent B=0.1% formic acid in Acetonitrile; flow rate: 0.6 mL/min. Reaction products were purified by flash column chromatography using CombiFlash® Rf with Teledyne Isco RediSep® Rf High Performance Gold or Silicycle SiliaSep™ High Performance columns (4 g, 12 g, 24 g, 40 g, or 80 g), Waters HPLC system using SunFire™ Prep C18 column (19×100 mm, 5 μm particle size): solvent gradient=80% A at 0 min, 5% A at 25 min; solvent A=0.035% TFA in Water; solvent B=0.035% TFA in MeOH; flow rate: 25 mL/min (Method A), and Waters Acquity UPLC/MS system (Waters PDA eλ Detector, QDa Detector, Sample manager—FL, Binary Solvent Manager) using Acquity UPLC® BEH C18 column (2.1×50 mm, 1.7 m particle size): solvent gradient=80% A at 0 min, 5% A at 2 min; solvent A=0.1% formic acid in Water; solvent B=0.1% formic acid in Acetonitrile; flow rate: 0.6 mL/min (method B). The purity of all compounds was over 95% and was analyzed with Waters LC/MS system. $^1$H NMR was obtained using a 500 MHz Bruker Avance III. Chemical shifts are reported relative to dimethyl sulfoxide (δ=2.50) for ¹H NMR. Data are reported as (br=broad, s=singlet, d=doublet, t=triplet, q=quartet, m=multiplet).

Abbreviations used in the following examples and elsewhere herein are:
atm atmosphere
br broad
DCM dichloromethane
DIEA N,N-diisopropylethylamine
DMA N,N-dimethylacetamide
DMF N,N-dimethylformamide
DMSO dimethyl sulfoxide
EDCI 1-ethyl-3-(3-dimethylaminopropyl) carbodiimide
ESI electrospray ionization
EtOAc ethyl acetate
HCl hydrochloric acid
h hour(s)
HATU bis(dimethylamino)methylene]-1H-1,2,3-triazolo[4,5-b]pyridinium 3-oxide hexafluoro-phosphate
HPLC high-performance liquid chromatography
LCMS liquid chromatography-mass spectrometry
m multiplet
MeOH methanol
MHz megahertz
min minutes
MS mass spectrometry
NMR nuclear magnetic resonance
Pd₂(dba)₃ tris(dibenzylideneacetone)dipalladium(0)
ppm parts per million
TBAF tetra-n-butylammonium fluoride
THF tetrahydrofuran
TLC thin layer chromatography
Xphos 2-dicyclohexylphosphino-2',4',6'-triisopropylbiphenyl Example 1: Synthesis of 2-(2,6-dioxopiperidin-3-yl)-4-((2-(3-(4-(4-(9-(isoquinolin-7-yl)-2-oxobenzo[h][1,6]naphthyridin-1(2H)-yl)-2-(trifluoromethyl)phenyl)piperazin-1-yl)-3-oxopropoxy)ethyl)amino)isoindoline-1,3-dione (I-1)

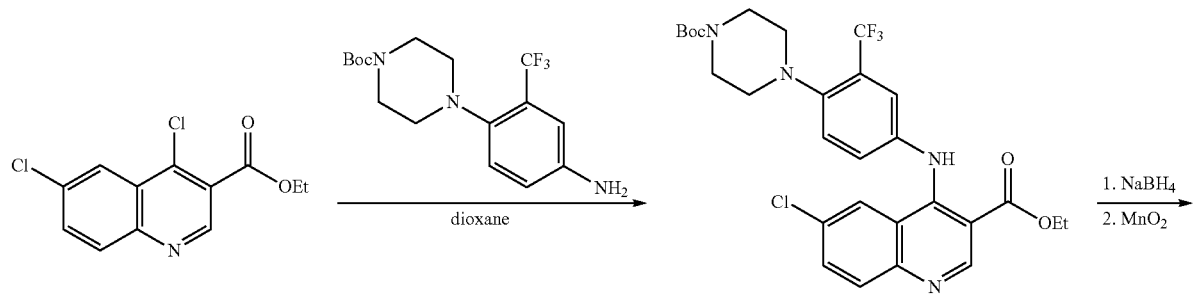

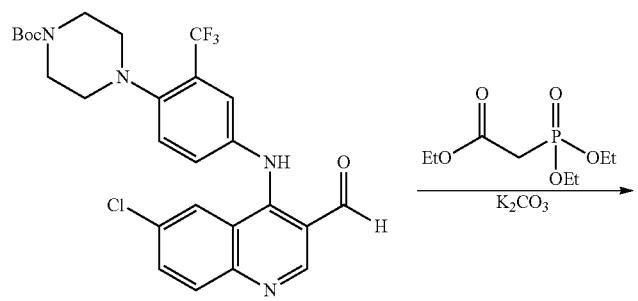

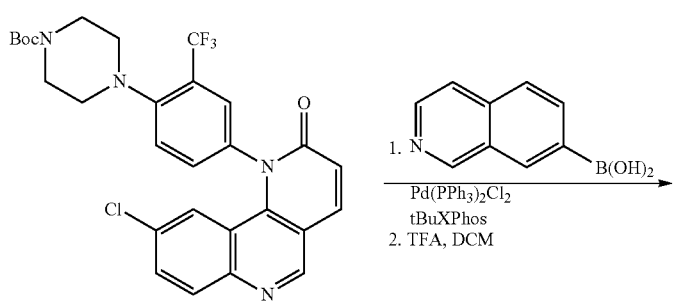

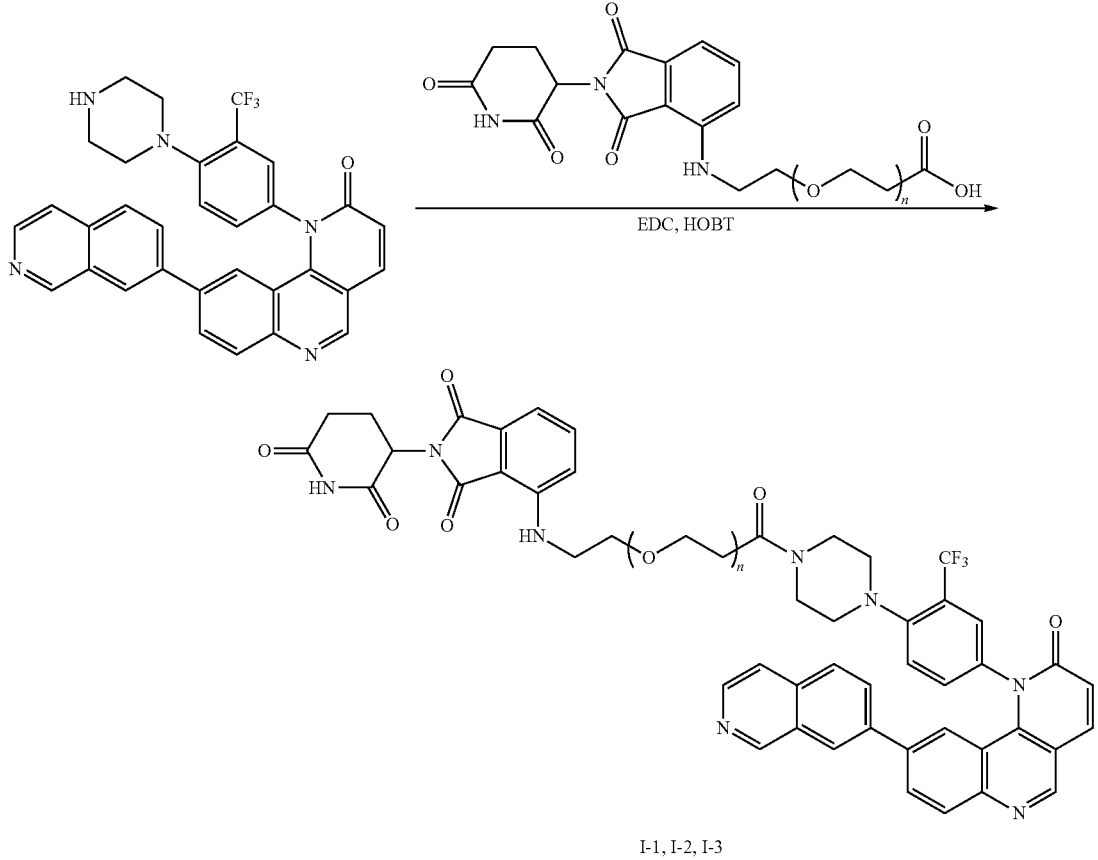

I-1, I-2, I-3

Step 1: Synthesis of Ethyl 4-((4-(4-(tert-butoxycarbonyl)piperazin-1-yl)-3-(trifluoromethyl)phenyl)amino)-6-chloroquinoline-3-carboxylate Ethyl 4,6-dichloroquinoline-3-carboxylate (569 mg, 2.1 mmol), tert-butyl 4-(4-amino-2-(trifluoromethyl)phenyl)piperazine-1-carboxylate (727 mg, 2.1 mmol), and DIEA (258 mg, 0.35 mL, 2 mmol) were mixed in dioxane (10 mL). The mixture was stirred at 100° C. overnight. The reaction was concentrated and purified by flash column chromatography on silica gel (0-70% EtOAc in hexane) to give the title compound as a yellow solid (465 mg, 38%). LCMS: m/z 579.2 [M+1].

Step 2: Synthesis of tert-Butyl 4-(4-(9-chloro-2-oxobenzo[h][1,6]naphthyridin-1(2H)-yl)-2-(trifluoromethyl)phenyl)piperazine-1-carboxylate To a solution of ethyl 4-((4-(4-(tert-butoxycarbonyl)piperazin-1-yl)-3-(trifluoromethyl)phenyl)amino)-6-chloroquinoline-3-carboxylate (465 mg, 0.80 mmol) in EtOH (10 mL) was added NaBH$_4$ (304 mg, 8.0 mmol) slowly. The mixture was stirred at rt overnight. The reaction was concentrated and extracted with EtOAc from H$_2$O, washed with brine, dried (Na$_2$SO$_4$), and concentrated. The residue was mixed in DCM (10 mL) and MnO$_2$ (2 g) was added. The mixture was stirred at rt overnight. The mixture was filtered through Celite and concentrated. The residue was dissolved in EtOH (10 mL) and triethyl phosphonoacetate (362 mg, 1.6 mmol) was added, followed by K$_2$CO$_3$ (331 mg, 2.4 mmol). The mixture was stirred at 100° C. overnight. The mixture was concentrated and purified by flash column chromatography on silica gel (100% EtOAc) to give the title compound as a yellow solid (138 mg, 31% over three steps). LCMS: m/z 559.2 [M+1].

Step 3: Synthesis of 9-(Isoquinolin-7-yl)-1-(4-(piperazin-1-yl)-3-(trifluoromethyl)phenyl) benzo[h][1,6]naphthyridin-2(1H)-one To a sealed tube was added tert-Butyl 4-(4-(9-chloro-2-oxobenzo[h][1,6]naphthyridin-1(2H)-yl)-2-(trifluoromethyl)phenyl)piperazine-1-carboxylate (138 mg, 0.25 mmol), isoquinolin-7-ylboronic acid (86.5 mg, 0.5 mmol), tBuXPhos (10.6 mg, 0.025 mmol), dioxane (6 mL), and Na$_2$CO$_3$ (1.5 mL). The mixture was degassed and Pd(PPh$_3$)$_2$CH$_2$ (17.5 mg, 0.025 mmol) was added. The mixture was stirred at 80° C. overnight. The mixture was filtered and concentrated. The residue was dissolved in DCM (1 mL) and TFA (1 mL) and stirred at rt for 1 h. The reaction was concentrated and purified by flash column chromatography on silica gel (0-10% MeOH in DCM) to give the title compound as a yellow solid (131 mg, 95% over two steps). LCMS: m/z 552.2 [M+1].

Step 4: Synthesis of 2-(2,6-Dioxopiperidin-3-yl)-4-((2-(3-(4-(4-(9-(isoquinolin-7-yl)-2-oxobenzo[h][1,6]naphthyridin-1(2H)-yl)-2-(trifluoromethyl)phenyl)piperazin-1-yl)-3-oxopropoxy)ethyl)amino)isoindoline-1,3-dione (I-1)

To a solution of 9-(isoquinolin-7-yl)-1-(4-(piperazin-1-yl)-3-(trifluoromethyl)phenyl)benzo[h][1,6]naphthyridin-2(1H)-one (13 mg, 0.0232 mmol) and 3-(2-((2-(2,6-dioxopiperidin-3-yl)-1,3-dioxoisoindolin-4-yl)amino)ethoxy)propanoic acid (13 mg, 0.0232 mmol) in DMF (0.5 mL) were added EDC (5.3 mg, 0.0278 mmol), HOBT (4.1 mg, 0.03 mmol), and TEA (12 mg, 16 µL, 0.116 mmol). The mixture was stirred at rt overnight. The mixture was purified by reverse phase HPLC (0-100% MeOH in H$_2$O) to give compound I-1 as a yellow solid (11 mg, 51%). $^1$H NMR (500 MHz, DMSO-d$_6$) δ 11.01 (s, 1H), 9.43 (s, 1H), 9.16 (s, 1H), 8.54 (d, J=6.0 Hz, 1H), 8.30 (d, J=9.5 Hz, 1H), 8.19-8.11 (m, 2H), 8.11-8.06 (m, 2H), 8.05-7.96 (m, 2H), 7.66 (dt, J=8.5, 2.5 Hz, 1H), 7.58-7.47 (m, 3H), 7.07 (d, J=8.6 Hz, 1H), 7.05 (d, J=1.9 Hz, 1H), 6.96 (d, J=7.0 Hz, 1H), 6.91 (d, J=9.4 Hz, 1H), 6.53 (s, 1H), 4.97 (ddd, J=12.9, 5.4, 2.3 Hz, 1H), 3.63 (t, J=6.6 Hz, 2H), 3.56 (t, J=5.5 Hz, 2H), 3.48-3.37 (m, 2H), 3.37-3.29 (m, 2H), 3.29-3.20 (m, 1H), 2.83-2.72 (m, 1H), 2.72-2.58 (m, 2H), 2.54-2.47 (m, 2H), 2.34-2.25 (m, 1H), 1.96-1.87 (m, 1H). LCMS: m/z 923.3 [M+1].

Example 2: Synthesis of 2-(2,6-dioxopiperidin-3-yl)-4-((2-(2-(2-(3-(4-(4-(9-isoquinolin-7-yl)-2-oxobenzo[h][1,6]naphthyridin-1(2H)-yl)-2-(trifluoromethyl)phenyl)piperazin-1-yl)-3-oxopropoxy)ethoxy)ethoxy)ethyl)amino)isoindoline-1,3-dione (I-2)

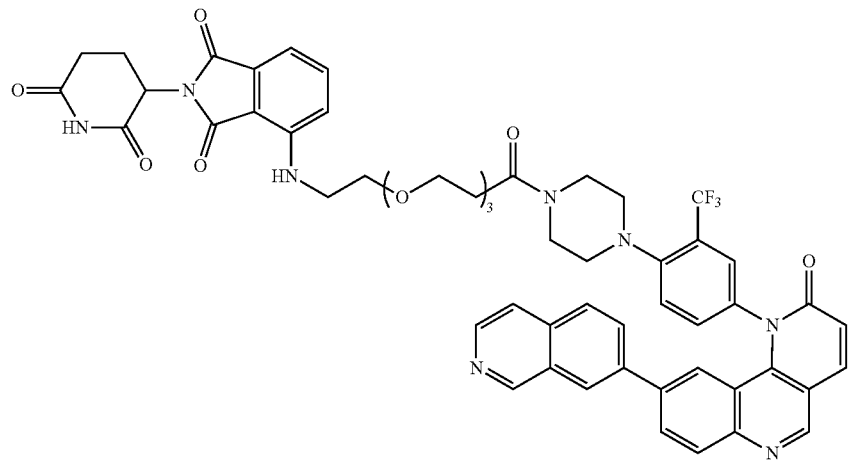

To a solution of 9-(isoquinolin-7-yl)-1-(4-(piperazin-1-yl)-3-(trifluoromethyl)phenyl) benzo[h][1,6]naphthyridin-2(1H)-one (8.5 mg, 0.0154 mmol) and 3-(2-(2-(2-((2-(2,6-dioxopiperidin-3-yl)-1,3-dioxoisoindolin-4-yl)amino)ethoxy)ethoxy)ethoxy)propanoic acid (10 mg, 0.0154 mmol) in DMF (0.5 mL) were added EDC (3.5 mg, 0.0185 mmol), HOBT (2.7 mg, 0.02 mmol), and TEA (7.8 mg, 11 µL, 0.077 mmol). The mixture was stirred at rt overnight. The mixture was purified by reverse phase HPLC (0-100% MeOH in H$_2$O) to give compound I-2 as a yellow solid (7.2 mg, 46%). $^1$H NMR (500 MHz, DMSO-d$_6$) δ 11.02 (s, 1H), 9.45 (s, 1H), 9.16 (s, 1H), 8.56 (d, J=6.0 Hz, 1H), 8.29 (d, J=9.5 Hz, 1H), 8.19-8.11 (m, 3H), 8.09 (dd, J=8.7, 1.9 Hz, 1H), 8.03 (d, J=8.6 Hz, 1H), 7.99 (d, J=2.4 Hz, 1H), 7.67 (dd, J=8.5, 2.5 Hz, 1H), 7.56 (d, J=8.6 Hz, 1H), 7.53 (dd, J=8.6, 1.9 Hz, 1H), 7.48 (dd, J=8.6, 7.1 Hz, 1H), 7.06-7.02 (m, 2H), 6.94 (d, J=7.0 Hz, 1H), 6.91 (d, J=9.4 Hz, 1H), 6.51 (s, 1H), 4.98 (dd, J=12.7, 5.5 Hz, 1H), 3.60-3.50 (m, 3H), 3.50-3.40 (m, 7H), 3.40-3.28 (m, 2H), 3.28-3.19 (m, 1H), 2.81 (ddd, J=16.8, 13.7, 5.4 Hz, 1H), 2.73-2.65 (m, 1H), 2.65-2.58 (m, 1H), 2.55-2.51 (m, 1H), 2.51-2.45 (m, 2H), 2.32-2.24 (m, 0H), 1.99-1.88 (m, 1H). LCMS: m/z 1011.4 [M+1].

Example 3: Synthesis of 2-(2,6-dioxopiperidin-3-yl)-4-((18-(4-(4-(9-(isoquinolin-7-yl)-2-oxobenzo[h][1,6]naphthyridin-1(2H)-yl)-2-(trifluoromethyl)phenyl)piperazin-1-yl)-18-oxo-3,6,9,12,15-pentaoxaoctadecyl)amino)isoindoline-1,3-dione (I-3)

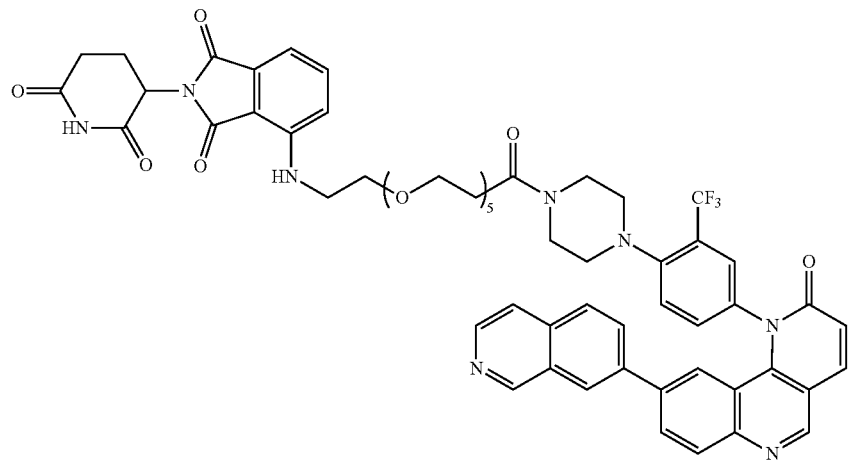

To a solution of 9-(isoquinolin-7-yl)-1-(4-(piperazin-1-yl)-3-(trifluoromethyl)phenyl) benzo[h][1,6]naphthyridin-2(1H)-one (8.3 mg, 0.015 mmol) and 1-((2-(2,6-dioxopiperidin-3-yl)-1,3-dioxoisoindolin-4-yl)amino)-3,6,9,12,15-pentaoxaoctadecan-18-oic acid (11 mg, 0.015 mmol) in DMF (0.5 mL) were added EDC (3.5 mg, 0.018 mmol), HOBT (2.6 mg, 0.02 mmol), and TEA (7.6 mg, 10 μl, 0.075 mmol). The mixture was stirred at rt overnight. The mixture was purified by reverse phase HPLC (0-100% MeOH in H$_2$O) to give compound I-3 as a yellow solid (7.7 mg, 47%). $^1$H NMR (500 MHz, DMSO-d$_6$) δ 11.02 (s, 1H), 9.48 (s, 1H), 9.17 (s, 1H), 8.58 (d, J=6.0 Hz, 1H), 8.29 (d, J=9.5 Hz, 1H), 8.21-8.13 (m, 3H), 8.09 (dd, J=8.7, 1.9 Hz, 1H), 8.06 (d, J=8.6 Hz, 1H), 7.99 (d, J=2.5 Hz, 1H), 7.67 (dd, J=8.5, 2.4 Hz, 1H), 7.59-7.52 (m, 2H), 7.49 (dd, J=8.6, 7.1 Hz, 1H), 7.05 (dd, J=5.3, 3.3 Hz, 2H), 6.95 (d, J=6.9 Hz, 1H), 6.91 (d, J=9.4 Hz, 1H), 6.52 (s, 1H), 4.98 (dd, J=12.7, 5.4 Hz, 1H), 3.61-3.50 (m, 4H), 3.50-3.20 (m, 17H), 2.81 (ddd, J=16.9, 13.7, 5.4 Hz, 1H), 2.74-2.66 (m, 1H), 2.65-2.57 (m, 1H), 2.55-2.51 (m, 1H), 2.51-2.46 (m, 2H), 2.34-2.24 (m, 1H), 2.00-1.88 (m, 1H). LCMS: m/z 1099.4 [M+1].

Example 4: Synthesis of (2R,4R)-1-((R)-2-(4-(4-(5-chloro-4-(1-oxo-2,8-diazaspiro[4.5]decan-8-yl)pyridin-3-yl)phenyl)-1H-pyrazol-1-yl)butanamido)-3,3-dimethylbutanoyl)-4-hydroxy-N-(4-(4-methylthiazol-5-yl)benzyl)pyrrolidine-2-carboxamide (I-4)

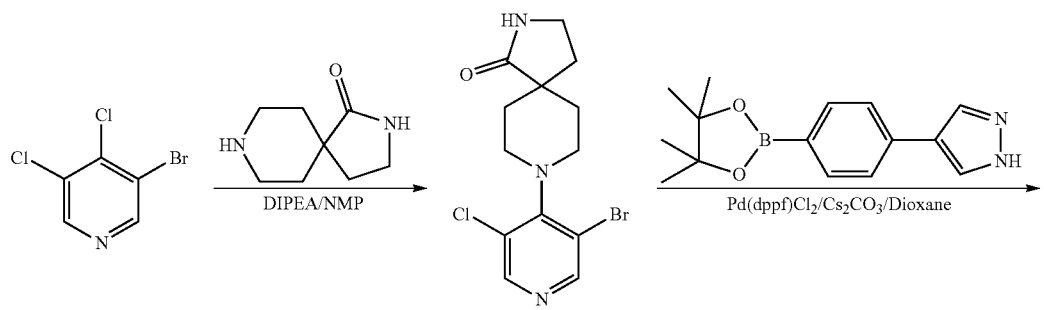

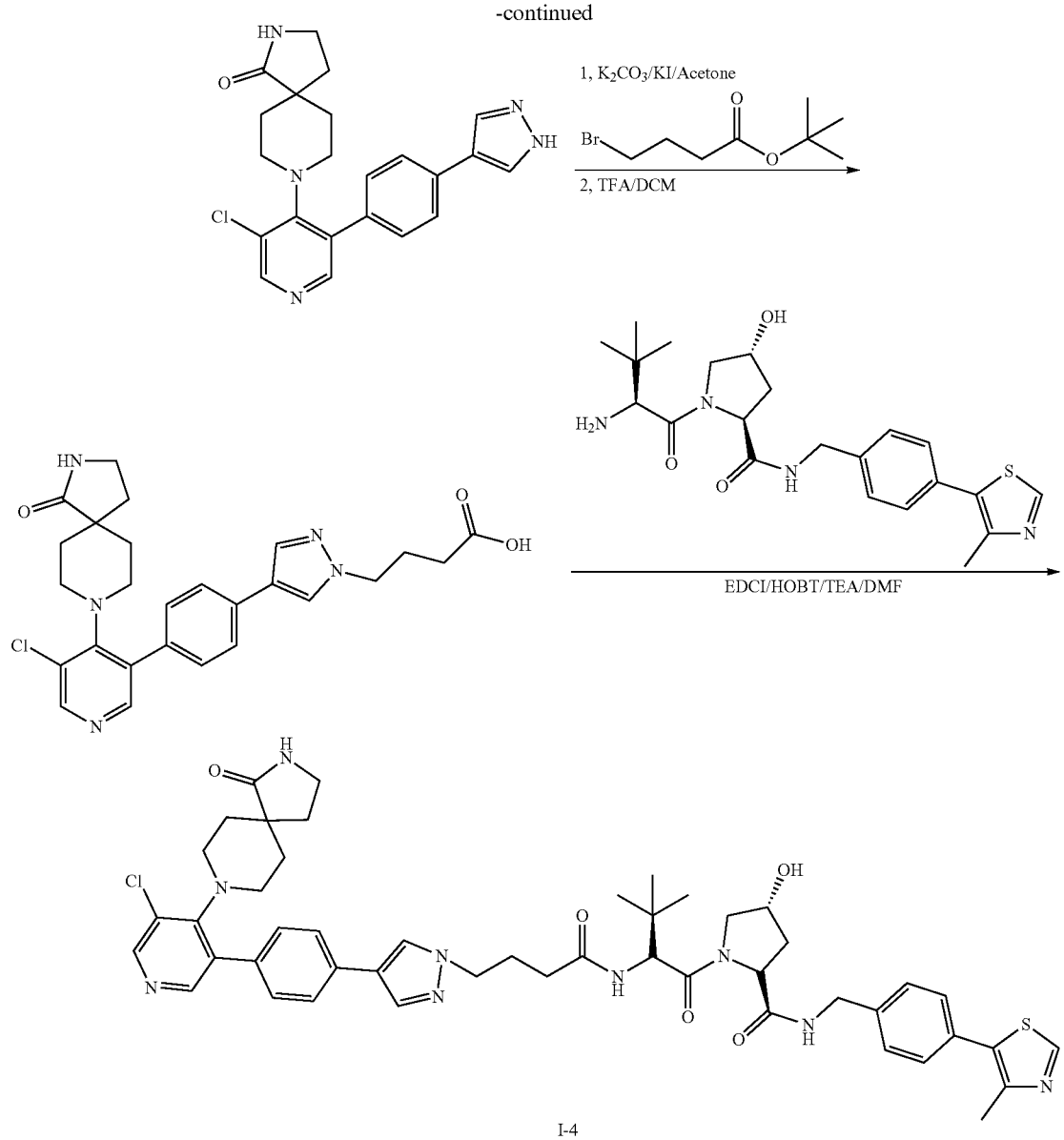

I-4

Step 1: Synthesis of 8-(3-(4-(1H-pyrazol-4-yl)phenyl)-5-chloropyridin-4-yl)-2,8-diazaspiro[4.5]decan-1-one 3-Bromo-4,5-dichloropyridine (454 mg, 2 mmol), 2,8-diazaspiro[4.5]decan-1-one (381 mg, 2 mmol), and DIPEA (516 mg, 0.7 mL, 4 mmol) were mixed in 5 mL of NMP. The mixture was heated to 120° C. and kept stirring overnight. The mixture was then cooled to room temperature and extracted with chloroform and isopropanol (V/V=4/1), dried over anhydrous $Na_2SO_4$ and concentrated. The crude was purified by column chromatography on silica gel (0-10% MeOH in DCM) to give 8-(3-bromo-5-chloropyridin-4-yl)-2,8-diazaspiro[4.5]decan-1-one (516 mg, 75%). LCMS: m/z 344.0 [M+1].

To a sealed tube were added 8-(3-bromo-5-chloropyridin-4-yl)-2,8-diazaspiro[4.5]decan-1-one (500 mg, 1.45 mmol), 4-(4-(4,4,5,5-tetramethyl-1,3,2-dioxaborolan-2-yl)phenyl)-1H-pyrazole (783 mg, 2.9 mmol), $Cs_2CO_3$ (1.43 g, 4.35 mmol), Dioxane (5.4 mL) and $H_2O$ (0.6 mL). The mixture was degassed and $Pd(dppf)Cl_2$ (118 mg, 0.15 mmol) was added. After addition, the mixture was heated to 110° C. and kept stirring overnight. The mixture was then cooled to room temperature and extracted with chloroform and isopropanol (V/V=4/1), dried over anhydrous $Na_2SO_4$ and concentrated. The crude was purified by column chromatography on silica gel (0-10% MeOH in DCM) to give 8-(3-(4-(1H-pyrazol-4-yl)phenyl)-5-chloropyridin-4-yl)-2,8-diazaspiro[4.5]decan-1-one as a white solid (473.5 mg, 80%). LCMS: m/z 408.2 [M+1].

Step 2: Synthesis of (2R,4R)-1-((R)-2-(4-(4-(4-(5-chloro-4-(1-oxo-2,8-diazaspiro[4.5]decan-8-yl)pyridin-3-yl)phenyl)-1H-pyrazol-1-yl)butanamido)-3,3-dimethylbutanoyl)-4-hydroxy-N-(4-(4-methylthiazol-5-yl)benzyl)pyrrolidine-2-carboxamide (I-4)

To a solution of 8-(3-(4-(1H-pyrazol-4-yl)phenyl)-5-chloropyridin-4-yl)-2,8-diazaspiro[4.5]decan-1-one (18.4 mg, 0.045 mmol) in Acetone (0.5 mL) was added tert-butyl 4-bromobutanoate (15.1 mg, 0.068 mmol), followed by $K_2CO_3$ (12.3 mg, 0.09 mmol) and KI (11.3 mg, 0.068 mmol). The mixture was then heated to reflux and kept stirring overnight. The mixture was diluted with EtOAc and $H_2O$, extracted, and washed with brine. The organic layer was dried over anhydrous $Na_2SO_4$ and concentrated. The crude was purified by column chromatography on silica gel (0-10% MeOH in DCM) to give t-butyl ester as a gray solid (23.5 mg, 95%). LCMS: m/z 550.3 [M+1].

To a solution of the t-butyl ester (22 mg, 0.04 mmol) in DCM (0.5 mL) was added TFA (0.5 mL) and stirred at rt for 2 h. The mixture was then concentrated and dissolved in DMF (0.5 mL). (2S,4R)-1-((S)-2-amino-3,3-dimethylbutanoyl)-4-hydroxy-N-(4-(4-methylthiazol-5-yl)benzyl)pyrrolidine-2-carboxamide (17.2 mg, 0.04 mmol) was added, followed by EDCI (8.7 mg, 0.046 mmol), HOBT (6.6 mg, 0.049 mmol), and TEA (19 mg, 26 L, 0.19 mmol). The mixture was stirred at rt overnight. The mixture was filtered and purified by reverse phase HPLC (0-100% MeOH in $H_2O$) to give compound I-4 as a yellow solid (16.3 mg, 45% over two steps). $^1$H NMR (500 MHz, DMSO-$d_6$) δ 8.97 (s, 1H), 8.61-8.53 (m, 2H), 8.26 (d, J=3.9 Hz, 2H), 7.98 (d, J=13.0 Hz, 2H), 7.75-7.69 (m, 3H), 7.53 (s, 1H), 7.42 (d, J=8.3 Hz, 2H), 7.37 (d, J=8.3 Hz, 2H), 7.33 (d, J=8.1 Hz, 2H), 4.55 (d, J=9.2 Hz, 1H), 4.48-4.40 (m, 2H), 4.36 (dq, J=6.4, 3.2 Hz, 2H), 4.21 (dd, J=15.9, 5.5 Hz, 1H), 4.12 (t, J=6.9 Hz, 2H), 3.68 (d, J=3.4 Hz, 2H), 3.11 (q, J=7.9, 6.7 Hz, 4H), 2.75-2.65 (m, 2H), 2.43 (s, 3H), 2.03 (ddd, J=14.3, 11.3, 6.8 Hz, 4H), 1.91 (ddd, J=12.9, 8.6, 4.6 Hz, 1H), 1.83 (t, J-=6.8 Hz, 2H), 1.72 (td, J=12.5, 4.2 Hz, 2H), 1.27 (d, J=12.8 Hz, 2H), 0.95 (s, 9H). LCMS: m/z 906.4 [M+1].

Example 5: Synthesis of (2S,4R)-1-((S)-20-tert-butyl-1-(4-(4-(5-chloro-4-(1-oxo-2,8-diazaspiro[4.5]decan-8-yl)pyridin-3-yl)phenyl)-1H-pyrazol-1-yl)-18-oxo-3,6,9,12,15-pentaoxa-19-azahenicosane)-4-hydroxy-N-(4-(4-methylthiazol-5-yl)benzyl) pyrrolidine-2-carboxamide (I-5)

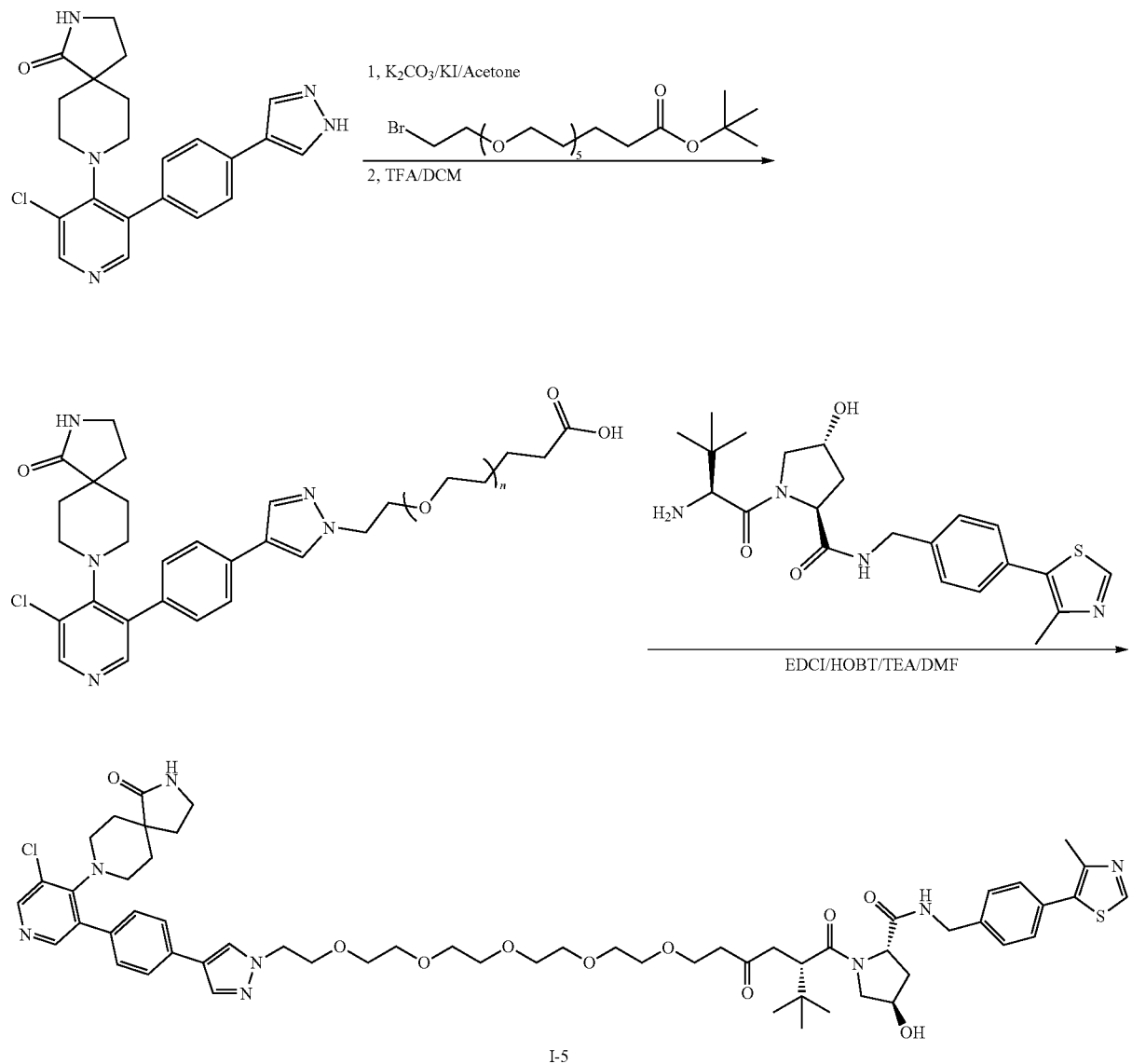

I-5

To a solution of 8-(3-(4-(1H-pyrazol-4-yl)phenyl)-5-chloropyridin-4-yl)-2,8-diazaspiro[4.5]decan-1-one (18.4 mg, 0.045 mmol) in Acetone (0.5 mL) was added tert-butyl 1-bromo-3,6,9,12,15-pentaoxaoctadecan-18-oate (30 mg, 0.068 mmol), followed by K$_2$CO$_3$ (12.3 mg, 0.09 mmol) and KI (11.3 mg, 0.068 mmol). The mixture was then heated to reflux and kept stirring overnight. The mixture was diluted with EtOAc and H$_2$O, extracted, and washed with brine. The organic layer was dried over anhydrous Na$_2$SO$_4$ and concentrated. The crude was purified by column chromatography on silica gel (0-10% MeOH in DCM) to give t-butyl ester (30.6 mg, 90%). LCMS: m/z 756.4 [M+1].

To a solution of the t-butyl ester (30 mg, 0.04 mmol) in DCM (0.5 mL) was added TFA (0.5 mL) and stirred at rt for 2 h. The mixture was then concentrated and dissolved in DMF (0.5 mL). (2S,4R)-1-((S)-2-amino-3,3-dimethylbutanoyl)-4-hydroxy-N-(4-(4-methylthiazol-5-yl)benzyl)pyrrolidine-2-carboxamide (17.2 mg, 0.04 mmol) was added, followed by EDCI (8.7 mg, 0.046 mmol), HOBT (6.6 mg, 0.049 mmol), and TEA (19 mg, 26 µL, 0.19 mmol). The mixture was stirred at rt overnight. The mixture was filtered and purified by reverse phase HPLC (0-100% MeOH in H$_2$O) to give compound I-5 as a yellow solid (15.6 mg, 35% over two steps). $^1$H NMR (500 MHz, DMSO-d$_6$) δ 8.95 (d, J=3.4 Hz, 1H), 8.60 (s, 1H), 8.52 (t, J=6.1 Hz, 1H), 8.29 (d, J=18.7 Hz, 1H), 8.22 (d, J=7.1 Hz, 1H), 7.98-7.92 (m, 1H), 7.87 (d, J=9.3 Hz, 1H), 7.67 (d, J=8.1 Hz, 2H), 7.50 (s, 1H), 7.41-7.29 (m, 6H), 4.51 (d, J=9.3 Hz, 1H), 4.42-4.35 (m, 2H), 4.31 (d, J=4.2 Hz, 1H), 4.25 (t, J=5.4 Hz, 2H), 4.17 (dd, J=15.9, 5.5 Hz, 1H), 3.77 (t, J=5.4 Hz, 2H), 3.63 (dd, J=10.5, 4.1 Hz, 1H), 3.60-3.56 (m, 1H), 3.49 (dd, J=5.8, 2.8 Hz, 2H), 3.45-3.40 (m, 8H), 3.14 (d, J=12.9 Hz, 2H), 3.07 (t, J=6.8 Hz, 2H), 2.69 (t, J=12.1 Hz, 2H), 2.46 (p, J=1.9 Hz, 8H), 2.40 (s, 3H), 2.34-2.26 (m, 1H), 1.99 (t, J=10.5 Hz, 1H), 1.86 (ddd, J=13.0, 8.6, 4.8 Hz, 2H), 1.81 (t, J=6.8 Hz, 2H), 1.69 (td, J=12.4, 12.0, 4.0 Hz, 2H), 1.26 (d, J=13.0 Hz, 2H), 0.89 (s, 9I). LCMS: m/z 1112.5 [M+1].

Example 6: Synthesis of 4-(4-(4-(4-(5-chloro-4-(1-oxo-2,8-diazaspiro[4.5]decan-8-yl)pyridin-3-yl)phenyl)-1H-pyrazol-1-yl)butylamino)-2-(2,6-dioxopiperidin-3-yl)isoindoline-1,3-dione (I-6)

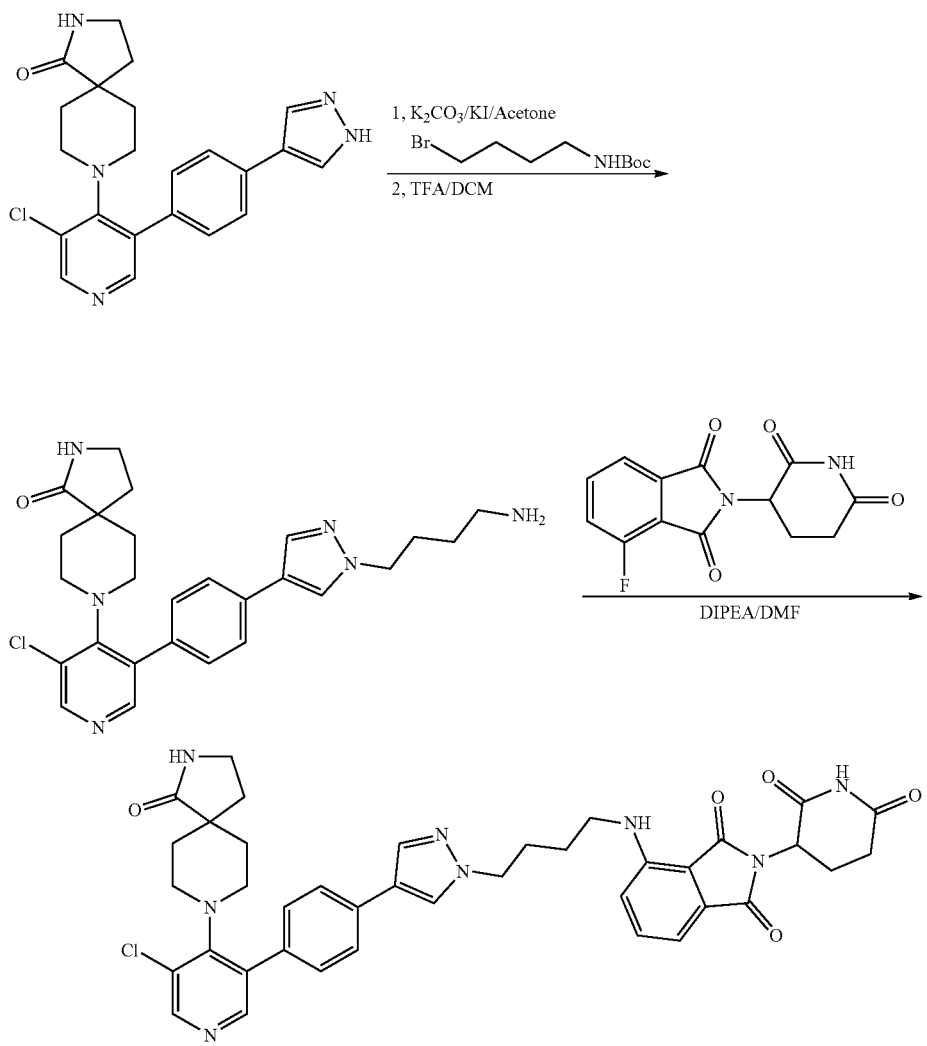

I-6

To a solution of 8-(3-(4-(1H-pyrazol-4-yl)phenyl)-5-chloropyridin-4-yl)-2,8-diazaspiro[4.5]decan-1-one (18.4 mg, 0.045 mmol) in Acetone (0.5 mL) was added tert-butyl 4-bromobutylcarbamate (17.2 mg, 0.068 mmol), followed by $K_2CO_3$ (12.3 mg, 0.09 mmol) and KI (11.3 mg, 0.068 mmol). The mixture was then heated to reflux and kept stirring overnight. The mixture was diluted with EtOAc and $H_2O$, extracted, and washed with brine. The organic layer was dried over anhydrous $Na_2SO_4$ and concentrated. The crude was purified by column chromatography on silica gel (0-10% MeOH in DCM) to give Boc protected amine (24.7 mg, 95%). LCMS: m/z 578.2 [M+1].

To a solution of the Boc protected amine (23 mg, 0.04 mmol) in DCM (0.5 mL) was added TFA (0.5 mL) and stirred at rt for 2 h. The mixture was then concentrated and dissolved in DMF (0.5 mL). 2-(2,6-dioxopiperidin-3-yl)-4-fluoroisoindoline-1,3-dione (11.1 mg, 0.04 mmol) was added, followed by EDCI (8.7 mg, 0.046 mmol), HOBT (6.6 mg, 0.049 mmol), and TEA (19 mg, 26 μL, 0.19 mmol). The mixture was stirred at rt overnight. The mixture was filtered and purified by reverse phase HPLC (0-100% MeOH in $H_2O$) to give compound I-6 as a yellow solid (11.2 mg, 38% over two steps). $^1$H NMR (500 MHz, DMSO-$d_6$) δ 11.08 (s, 1H), 8.55 (s, 1H), 8.28 (s, 1H), 8.26 (s, 1H), 7.97 (s, 1H), 7.70 (s, 1H), 7.68 (d, J=2.1 Hz, 1H), 7.56 (dd, J=8.6, 7.1 Hz, 1H), 7.53 (s, 1H), 7.34 (s, 1H), 7.33 (s, 11H), 7.10 (d, J=8.6 Hz, 1H), 7.00 (d, J=7.0 Hz, 1H), 6.62 (s, 1H), 5.04 (dd, J=12.7, 5.4 Hz, 1H), 4.19 (t, J=6.9 Hz, 2H), 3.34 (s, 2H), 3.11 (td, J=6.5, 3.3 Hz, 4H), 2.75-2.65 (m, 2H), 2.62-2.55 (m, 1H), 2.54 (s, 2H), 2.06-1.97 (m, 1H), 1.90 (p, J=7.0 Hz, 2H), 1.84 (t, J=6.8 Hz, 2H), 1.72 (td, J=12.4, 4.2 Hz, 2H), 1.62-1.51 (m, 2H), 1.28 (d, J=13.1 Hz, 2H). LCMS: m/z 735.3 [M+1].

Example 7: 2-(4-(4-(5-chloro-4-(1-oxo-2,8-diazaspiro[4.5]decan-8-yl)pyridin-3-yl)phenyl)-1H-pyrazol-1-yl)-N-(2-(2-(2-(2-(2-(2,6-dioxopiperidin-3-yl)-1,3-dioxoisoindolin-4-ylamino)ethoxy)ethoxy)ethoxy)ethyl)acetamide (I-7)

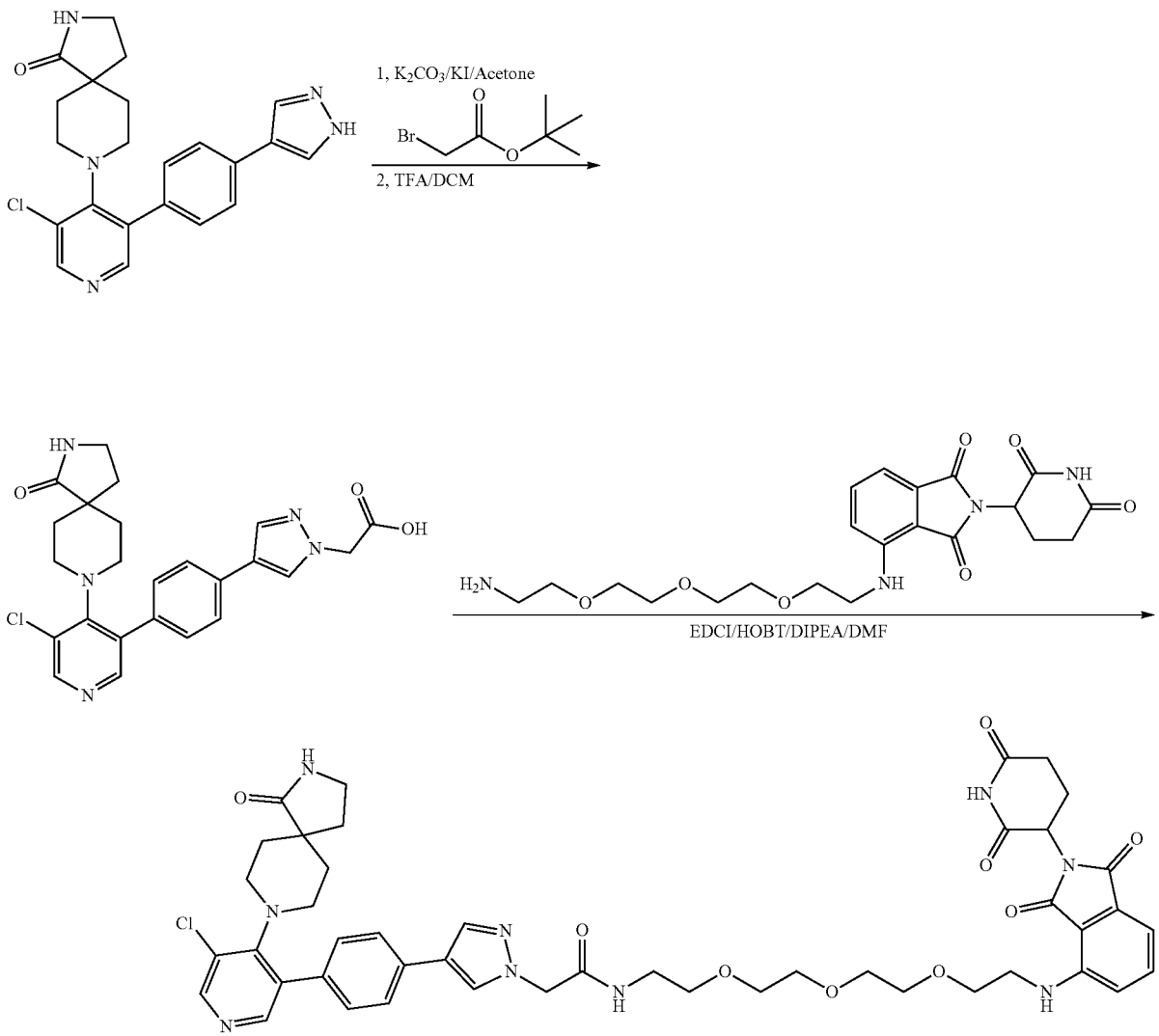

I-7

To a solution of 8-(3-(4-(1H-pyrazol-4-yl)phenyl)-5-chloropyridin-4-yl)-2,8-diazaspiro[4.5]decan-1-one (18.4 mg, 0.045 mmol) in Acetone (0.5 mL) was added tert-butyl 2-bromoacetate (13.2 mg, 0.068 mmol), followed by K₂CO₃ (12.3 mg, 0.09 mmol) and KI (11.3 mg, 0.068 mmol). The mixture was then heated to reflux and kept stirring overnight. The mixture was diluted with EtOAc and H₂O, extracted, and washed with brine. The organic layer was dried over anhydrous Na₂SO₄ and concentrated. The crude was purified by column chromatography on silica gel (0-10% MeOH in DCM) to give t-butyl ester (22.3 mg, 95%). LCMS: m/z 522.2 [M+1].

To a solution of the t-butyl ester (20.8 mg, 0.04 mmol) in DCM (0.5 mL) was added TFA (0.5 mL) and stirred at rt for 2 h. The mixture was then concentrated and dissolved in DMF (0.5 mL). 4-(2-(2-(2-(2-aminoethoxy)ethoxy)ethoxy)ethylamino)-2-(2,6-dioxopiperidin-3-yl)isoindoline-1,3-dione (17.9 mg, 0.04 mmol) was added, followed by EDCI (8.7 mg, 0.046 mmol), HOBT (6.6 mg, 0.049 mmol), and TEA (19 mg, 26 µL, 0.19 mmol). The mixture was stirred at rt overnight. The mixture was filtered and purified by reverse phase HPLC (0-100% MeOH 5 in H₂O) to give compound I-7 as a yellow solid (11.8 mg, 33% over two steps). ¹H NMR (500 MHz, DMSO-d₆) δ 11.09 (s, 1H), 8.57 (s, 1H), 8.28 (s, 1H), 8.21 (d, J=9.4 Hz, 1H), 7.98 (s, 1H), 7.70 (dd, J=7.6, 4.6 Hz, 2H), 7.60-7.50 (m, 2H), 7.35 (d, J=8.0 Hz, 2), 7.14 (d, J=8.6 Hz, 1H), 7.04 (d, J=7.0 Hz, 1H), 6.59 (d, J=15.1 Hz, 2H), 5.05 (dd, J=12.7, 5.4 Hz, 1H), 4.83 (s, 2H), 3.62 (t, J=5.4 Hz, 2H), 3.59-3.41 (m, 9H), 3.25 (q, J=5.6 Hz, 2H), 3.11 (q, J=6.6, 6.1 Hz, 3H), 2.94-2.82 (m, 2H), 2.69 (t, J=12.1 Hz, 2H), 2.58 (dt, J=16.9, 2.9 Hz, 1H), 2.02 (ddt, J=12.5, 5.6, 2.9 Hz, 4H), 1.84 (t, J=6.8 Hz, 2H), 1.72 (td, J=12.5, 4.2 Hz, 2H), 1.28 (d, J=13.0 Hz, 2H). LCMS: m/z 896.3 [M+1].

Example 8: 4-(4-(4-(5-chloro-4-(1-oxo-2,8-diazaspiro[4.5]decan-8-yl)pyridin-3-yl)phenyl)-1H-pyrazol-1-yl)-N-(2-(2-(2-(2-(2,6-dioxopiperidin-3-yl)-1,3-dioxoisoindolin-4-ylamino)ethoxy)ethoxy)ethoxy)ethyl)butanamide (I-8)

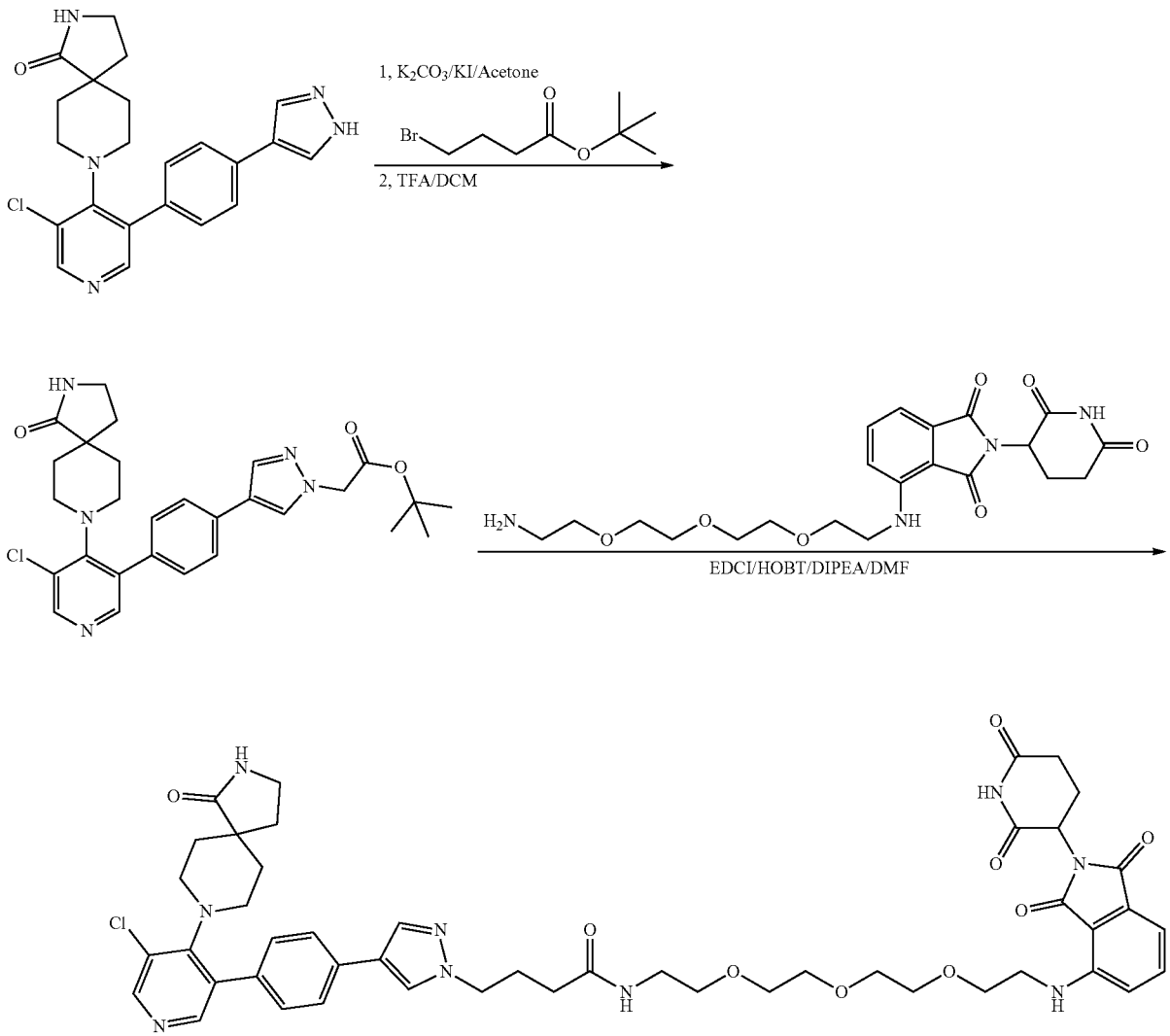

I-7

To a solution of 8-(3-(4-(1H-pyrazol-4-yl)phenyl)-5-chloropyridin-4-yl)-2,8-diazaspiro[4.5]decan-1-one (18.4 mg, 0.045 mmol) in Acetone (0.5 mL) was added tert-butyl 4-bromobutanoate (15.1 mg, 0.068 mmol), followed by $K_2CO_3$ (12.3 mg, 0.09 mmol) and KI (11.3 mg, 0.068 mmol). The mixture was then heated to reflux and kept stirring overnight. The mixture was diluted with EtOAc and $H_2O$, extracted, and washed with brine. The organic layer was dried over anhydrous $Na_2SO_4$ and concentrated. The crude was purified by column chromatography on silica gel (0-10% MeOH in DCM) to give t-butyl ester (23.5 mg, 95%). LCMS: m/z 550.3 [M+1].

To a solution of the t-butyl ester (22 mg, 0.04 mmol) in DCM (0.5 mL) was added TFA (0.5 mL) and stirred at rt for 2 h. The mixture was then concentrated and dissolved in DMF (0.5 mL). 4-(2-(2-(2-(2-aminoethoxy)ethoxy)ethoxy)ethylamino)-2-(2,6-dioxopiperidin-3-yl)isoindoline-1,3-dione (17.9 mg, 0.04 mmol) was added, followed by EDCI (8.7 mg, 0.046 mmol), HOBT (6.6 mg, 0.049 mmol), and TEA (19 mg, 26 µL, 0.19 mmol). The mixture was stirred at rt overnight. The mixture was filtered and purified by reverse phase HPLC (0-100% MeOH in $H_2O$) to give compound I-8 as a yellow solid (11.1 mg, 30% over two steps). $^1$H NMR (500 MHz, DMSO-$d_6$) δ 11.09 (s, 1H), 8.56 (s, 1H), 8.25 (d, J=6.2 Hz, 2H), 7.96 (s, 1H), 7.89 (t, J=5.6 Hz, 1H), 7.74-7.67 (m, 2H), 7.57 (dd, J=8.6, 7.1 Hz, 1H), 7.53 (d, J=2.8 Hz, 1H), 7.38-7.32 (m, 2H), 7.13 (d, J=8.6 Hz, 1H), 7.03 (d, J=7.0 Hz, 1H), 6.58 (d, J=10.4 Hz, 1H), 5.05 (dd, J=12.8, 5.5 Hz, 1H), 4.12 (t, J=6.8 Hz, 2H), 3.60 (t, J=5.4 Hz, 2H), 3.57-3.42 (m, 10H), 3.39 (t, J=5.9 Hz, 2H), 3.19 (q, J=5.8 Hz, 2H), 3.15-3.06 (m, 4H), 2.76-2.65 (m, 2H), 2.62-2.55 (m, 1H), 2.54 (s, 1H), 2.13-2.06 (m, 2H), 2.06-1.97 (m, 4H), 1.84 (t, 0.1=6.8 Hz, 2H), 1.72 (td, J=12.5, 4.1 Hz, 2H), 1.28 (d, J=12.9 Hz, 2H). LCMS: m/z 924.4 [M+1].

Example 9: Biochemical Studies

Cell Viability Assay

Figure 1B:
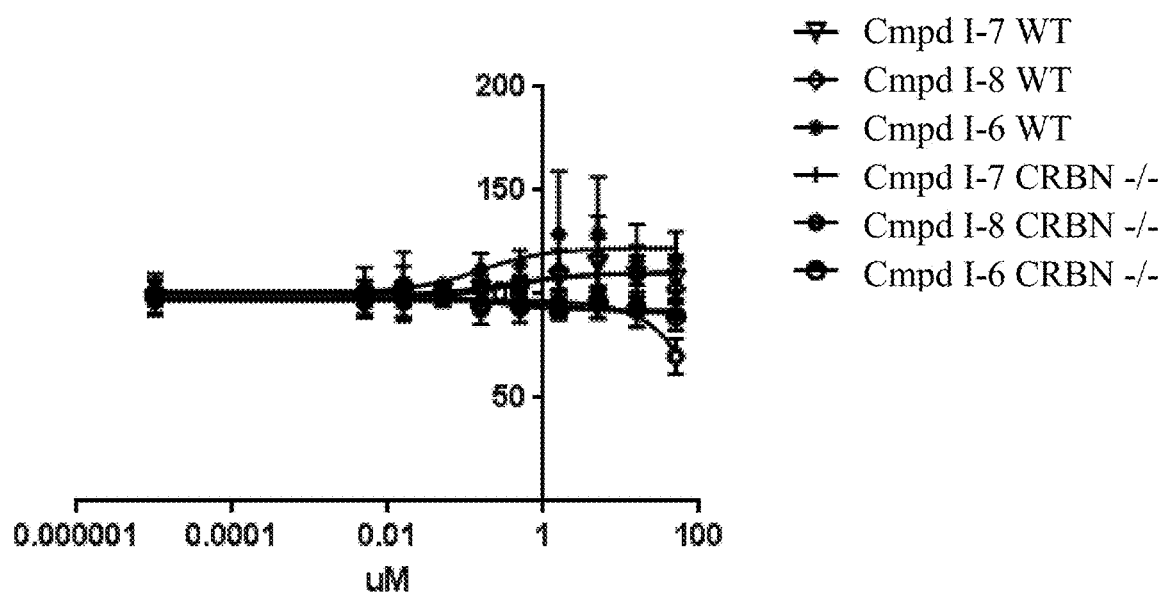
FIG. 1B is a graph showing anti-proliferative effects of Compound I-6, Compound I-7, and Compound I-8 in wild-type (WT) or cereblon knockout (CRBN−/−) cells at various concentrations. Antiproliferative effects were assessed 72 hours after treatment.

Molt4 wild-type or cereblon null cells were treated with a titration of a bifunctional compound of the invention (i.e., Compound I-1, Compound I-2, or Compound I-3) and allowed to grow for 72 hours. Cells were assayed using celltiter glo (Promega) to determine cell viability by measuring the amount of ATP present, which is an indicator of cell metabolic activity. Results are graphed as relative luminescent values. The results are shown in FIG. 1A and FIG. 1B.

Enzyme Degradation Assay

Figure 2:
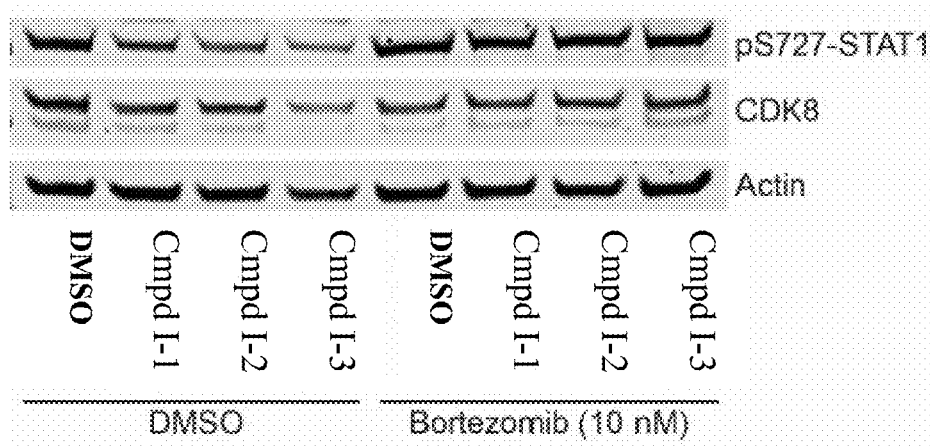
FIG. 2 is a western blot showing the levels of CDK8, pS727-STAT1, and actin in MC38 colorectal cancer cells treated with 1 μM Compound I-1, Compound I-2, Compound I-3, or DMSO, alone or in combination with 10 nM bortezomib for 6 hours. Compound I-3 efficiently degraded CDK8 and lowered the level of phosphorylation of the known CDK8 substrate Ser727-STAT1. Inhibiting the proteasome with bortezomib rescued both the degradation of CDK8 and the reduction in the level of pSer727-STAT1.
Figure 3A:
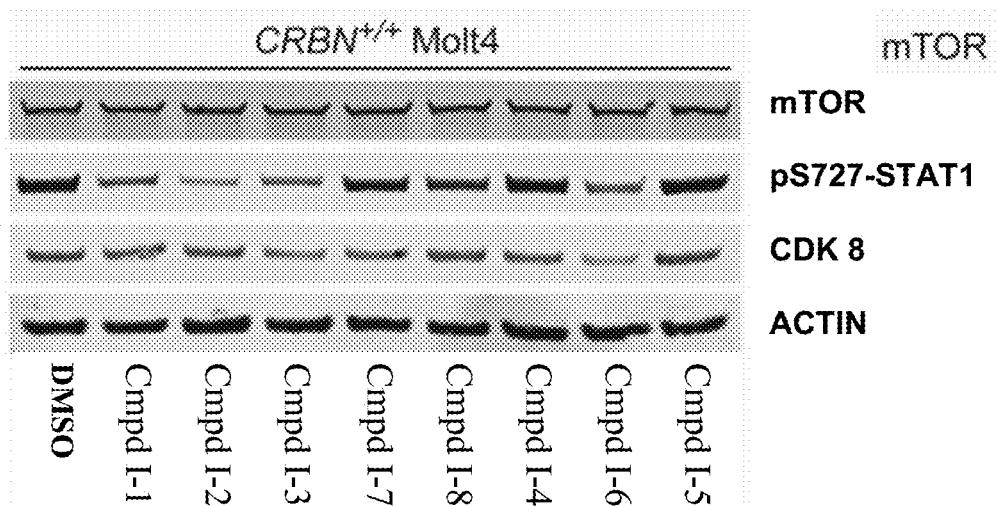
FIG. 3A and FIG. 3B are western blots showing the levels of mTOR, CDK8, pS727-STAT1, and actin in wild-type (WT) (FIG. 3A) or cereblon knockout (CRBN−/−) (FIG. 3B) Molt4 cells treated with DMSO or 1 μM Compound I-1, I-2, I-3, I-4, I-5, I-6, I-7, or I-8 for 6 hours. Compounds I-3 and I-6 efficiently degraded CDK8 and blocked phosphorylation of Ser727-STAT1 in WT Molt4 cells. CDK8 was not degraded in CRBN−/− Molt4 cells.
Figure 3B:
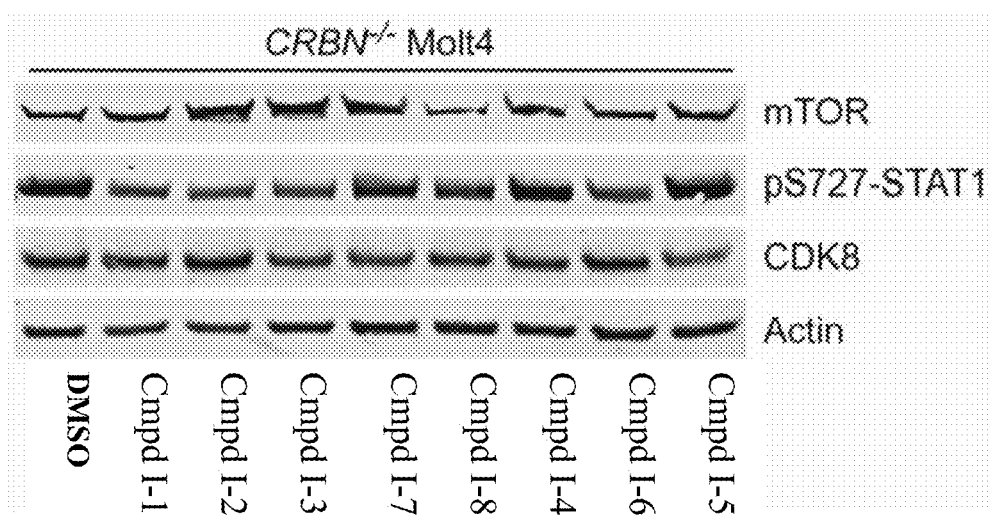
Figure 4A:
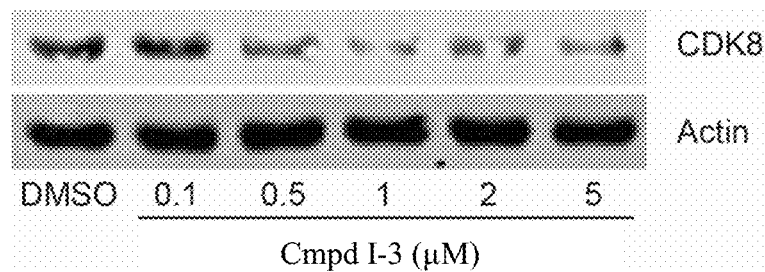
FIG. 4A is a western blot showing the levels of CDK8 and actin in cells treated with the indicated concentrations of Compound I-3 or DMSO.
Figure 4B:
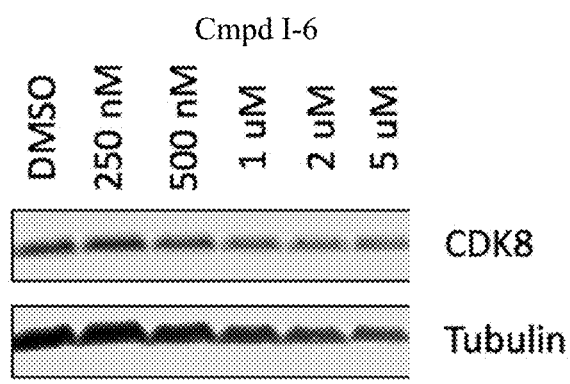
FIG. 4B is a western blot showing the levels of CDK8 and tubulin in Molt4 cells treated for 4 hours with the indicated concentrations of Compound I-6 or DMSO.
Figure 4C:
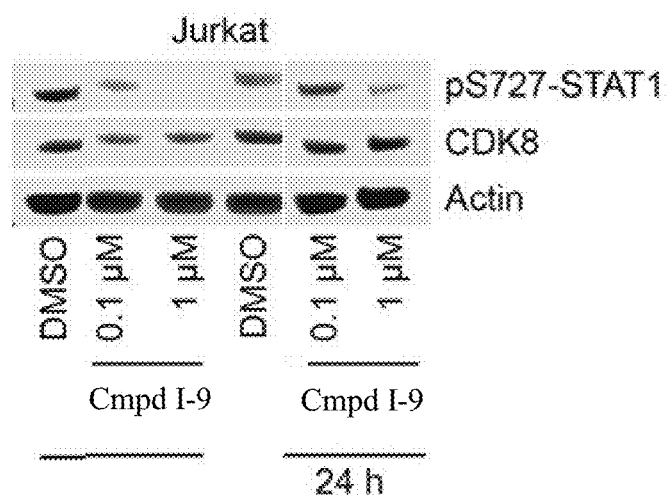
FIG. 4C is a western blot showing the levels of CDK8, pS727-STAT1, and actin in Jurkat cells treated with the indicated concentrations of Compound I-9 or DMSO.

The indicated cells were treated with vehicle control or the bifunctional compounds of the application, at a single or various concentrations, alone or in combination with bortezomib, an agent that blocks proteasomal degradation. After treatment, cells were washed with PBS and lysed in lysis buffer and then cleared by centrifugation. Protein concentrations were determined by BCA assay, and equal amounts of protein were loaded onto gels to perform Western blots. Gels were transferred to nitrocellulose, blocked with 5% milk in TBS-T, and probed for CDK8, mTOR, S727-STAT1, and Actin. Antibody binding was detected using near-infrared-dye-conjugated secondary antibodies. The results are shown in FIG. 2, FIG. 3A and FIG. 3B.

Western Blotting on CDK8 Cells were treated with the indicated compounds at the indicated concentrations for the indicated amount of time. Cells were then lysed in M-PER buffer (Thermo Scientific) containing protease/phosphatase inhibitor cocktail (Roche). Protein concentration was measured using a BCA assay (Pierce). Equivalent amounts of each samples were loaded on 4-12% Bis-Tris gels (Invitrogen), transferred to nitrocellulose membranes, and immunoblotted with antibodies against CDK8 and Actin (Cell Signaling). IRDye® 800-labeled goat anti-rabbit IgG and IRDye® 680-labeled goat anti-mouse IgG (LI-COR) secondary antibodies were purchased for LI-COR, and membranes were detected on an Odyssey detection system (LI-COR Biosciences). The results are shown in FIG. 2 and FIG. 4A-4C.

EQUIVALENTS

Those skilled in the art will recognize, or be able to ascertain using no more than routine experimentation, many equivalents to the specific embodiments and methods described herein. Such equivalents are intended to be encompassed by the scope of the present application.

All patents, patent applications, and literature references cited herein are hereby expressly incorporated by reference.

The invention claimed is:

1. A bifunctional compound of Formula X:

TL-L-D  (X), wherein:
the Targeting Ligand (TL) is of Formula TL-I:

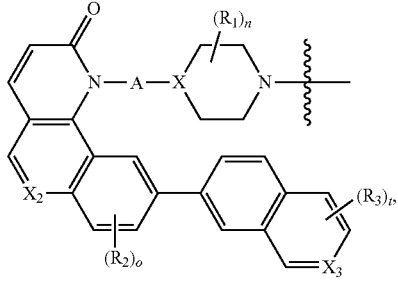

(TL-I)

wherein:
A is

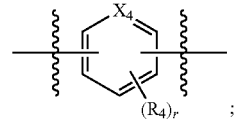

;

X is N or CH;
$X_2$ is N or CH;
$X_3$ is N or CH;
$X_4$ is N or CH;
each $R_1$ is independently $(C_1-C_4)$ alkyl or $(C_1-C_4)$ haloalkyl;
each $R_2$ is independently $(C_1-C_4)$ alkyl, $(C_1-C_4)$ haloalkyl, $(C_1-C_4)$ alkoxy, $(C_1-C_4)$ haloalkoxy, halogen, OH, or $NH_2$;
each $R_3$ is independently $(C_1-C_4)$ alkyl, $(C_1-C_4)$ haloalkyl, $(C_1-C_4)$ alkoxy, $(C_1-C_4)$ haloalkoxy, halogen, OH, or $NH_2$;
each $R_4$ is independently $(C_1-C_4)$ alkyl, $(C_1-C_4)$ haloalkyl, $(C_1-C_4)$ alkoxy, $(C_1-C_4)$ haloalkoxy, halogen, OH, or $NH_2$; and t, n, o, and r are each independently 0, 1, 2, or 3;
wherein the Targeting Ligand is bonded to the Linker via the

next to

the Linker (L) is a group that covalently binds to the Targeting Ligand and the Degron; and
the Degron (D) is of Formula D2:

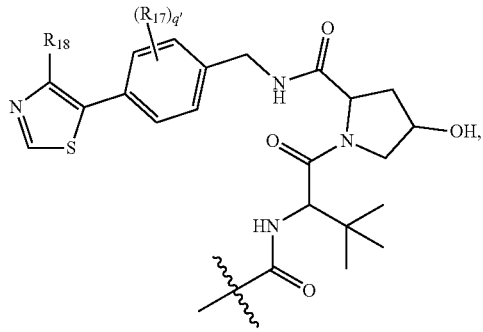

wherein:
each $R_{17}$ is independently ($C_1$-$C_3$) alkyl;
q' is 0, 1, 2, 3, or 4; and
$R_{18}$ is H or ($C_1$-$C_3$) alkyl,
wherein the Degron is covalently bonded to the Linker via the

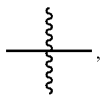

or a stereoisomer or pharmaceutically acceptable salt thereof.

2. The bifunctional compound of claim 1, wherein A is

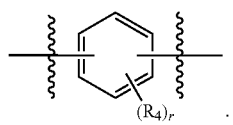

3. The bifunctional compound of claim 1, wherein X is N.
4. The bifunctional compound of claim 1, wherein $X_2$ is N.
5. The bifunctional compound of claim 1, wherein $X_3$ is N.
6. The bifunctional compound of claim 1, wherein t is 0.
7. The bifunctional compound of claim 1, wherein o is 0.

8. The bifunctional compound of claim 1, wherein n is 0.
9. The bifunctional compound of claim 1, wherein r is 1 and $R_4$ is ($C_1$-$C_4$) haloalkyl.
10. The bifunctional compound of claim 1, wherein the Targeting Ligand is of Formula TL-Ia, TL-Ib, TL-Ic, TL-Id, TL-Ie, or TL-If:

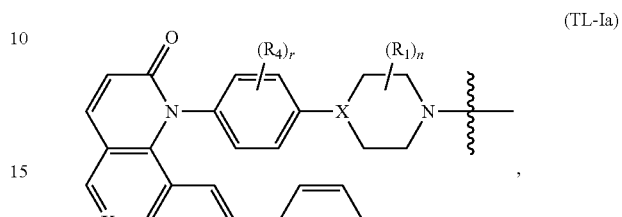
(TL-Ia)

(TL-Ib)

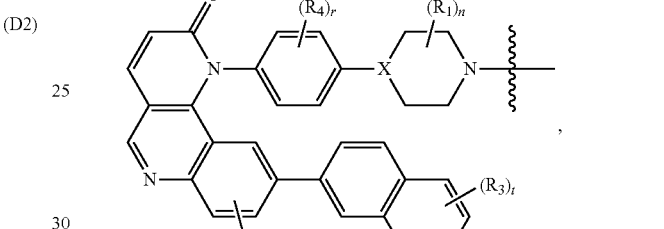
(TL-Ic)

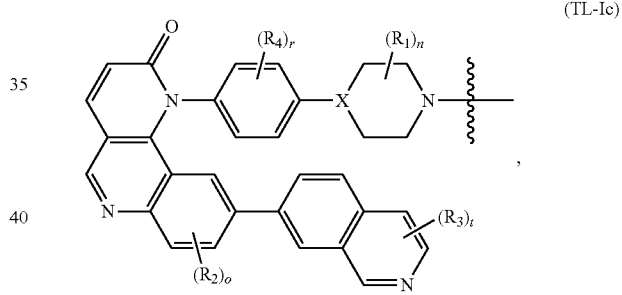
(TL-Id)

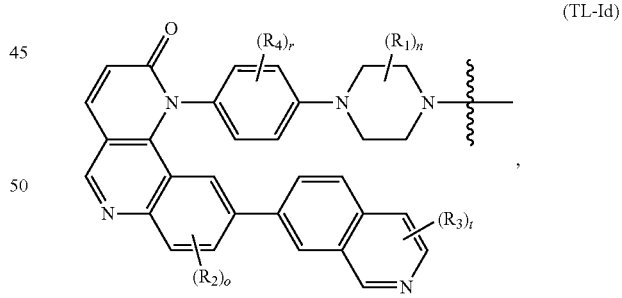

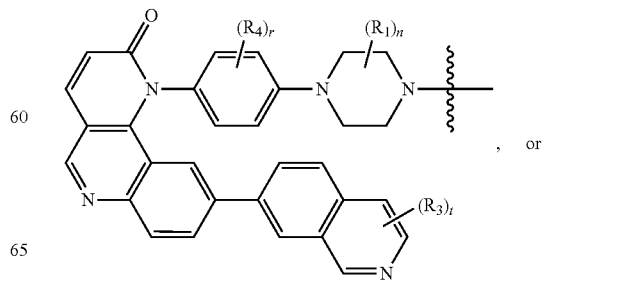
(TL-Ie)

, or

-continued (TL-1f)

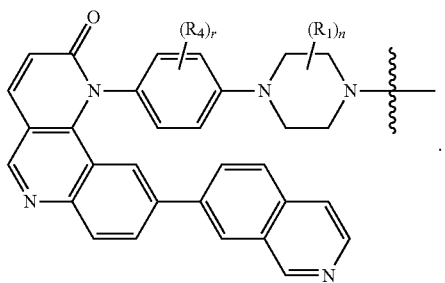

11. The bifunctional compound of claim 1, wherein the Linker is of Formula L0:

(L0)

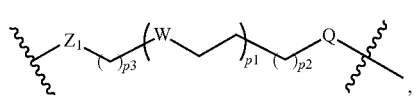

or a stereoisomer thereof, wherein
p1 is an integer selected from 0 to 12;
p2 is an integer selected from 0 to 12;
p3 is an integer selected from 1 to 6;
each W is independently absent, $CH_2$, O, S, NH, or $NR_{19}$;
$Z_1$ is absent, C(O), $(CH_2)_jC(O)NH$, $CH_2$, O, NH, or $NR_{19}$;
each $R_{19}$ is independently $C_1$-$C_3$ alkyl;
j is 1, 2, or 3; and
Q is absent or $NHC(O)CH_2$,
wherein the Linker is covalently bonded to the Degron via the

next to Q, and covalently bonded to the Targeting Ligand via the

next to $Z_1$.

12. The bifunctional compound of claim 11, wherein the Linker is selected from:

(L1)

(L2)

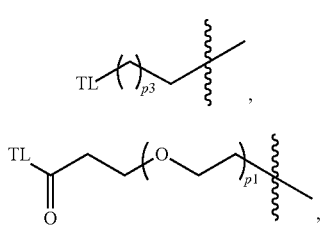

-continued (L3)

(L4)

(L5)

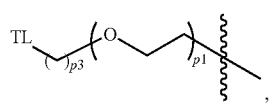

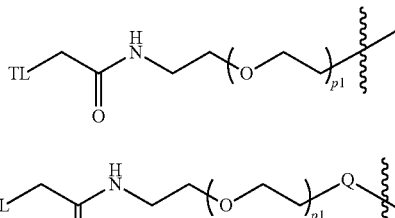

(L6)

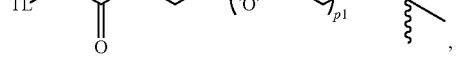, and (L7)

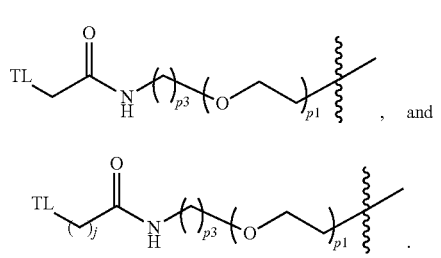.

13. The bifunctional compound of claim 1, wherein $R_{18}$ is methyl.

14. The bifunctional compound of claim 1, wherein the Degron is of Formula D2a or D2b:

(D2a)

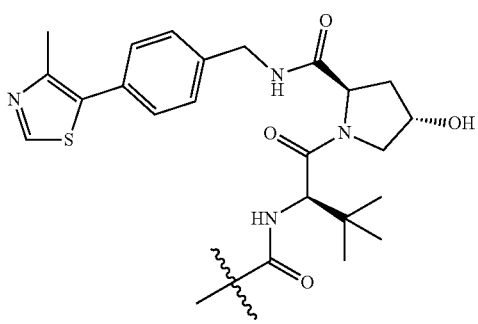

or (D2b)

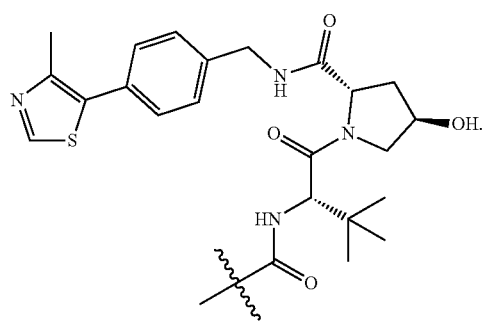.

15. A pharmaceutical composition comprising a therapeutically effective amount of the bifunctional compound of claim 1, or a stereoisomer or pharmaceutically acceptable salt thereof, and a pharmaceutically acceptable carrier.

16. A method of treating cancer, wherein the cancer is leukemia or lymphoma, comprising administering to a subject in need thereof an effective amount of the bifunctional compound or pharmaceutically acceptable salt or stereoisomer of claim 1.

* * * * *